US010519505B2

(12) United States Patent
Ostrer et al.

(10) Patent No.: US 10,519,505 B2
(45) Date of Patent: Dec. 31, 2019

(54) GENOMIC SIGNATURES OF METASTASIS IN PROSTATE CANCER

(75) Inventors: Harry Ostrer, New York, NY (US); Alexander Pearlman, New York, NY (US)

(73) Assignees: Harry Ostrer, New York, NY (US); Alexander Pearlman, New York, NY (US)

(*) Notice: Subject to any disclaimer, the term of this patent is extended or adjusted under 35 U.S.C. 154(b) by 0 days.

(21) Appl. No.: 14/114,057

(22) PCT Filed: Apr. 27, 2012

(86) PCT No.: PCT/US2012/035350
§ 371 (c)(1),
(2), (4) Date: Apr. 8, 2014

(87) PCT Pub. No.: WO2012/149245
PCT Pub. Date: Nov. 1, 2012

(65) Prior Publication Data
US 2014/0221229 A1 Aug. 7, 2014

Related U.S. Application Data

(60) Provisional application No. 61/479,914, filed on Apr. 28, 2011.

(51) Int. Cl.
C12Q 1/6886 (2018.01)
G16H 50/30 (2018.01)

(52) U.S. Cl.
CPC .......... *C12Q 1/6886* (2013.01); *G16H 50/30* (2018.01); *C12Q 2600/118* (2013.01); *C12Q 2600/156* (2013.01)

(58) Field of Classification Search
None
See application file for complete search history.

(56) References Cited

U.S. PATENT DOCUMENTS

| 7,482,123 | B2 | 1/2009 | Paris et al. | |
|---|---|---|---|---|
| 7,638,278 | B2 | 12/2009 | Pollack et al. | |
| 2003/0148327 | A1 | 8/2003 | Olek et al. | |
| 2007/0105133 | A1* | 5/2007 | Clarke et al. | 435/6 |
| 2007/0237770 | A1 | 10/2007 | Lai et al. | |
| 2009/0123439 | A1* | 5/2009 | Yun et al. | 424/93.21 |
| 2010/0131432 | A1* | 5/2010 | Kennedy et al. | 705/500 |

FOREIGN PATENT DOCUMENTS

| EP | 2 034 030 A2 | 3/2009 |
|---|---|---|
| EP | 2 272 982 A1 | 1/2011 |
| WO | 2006/052823 A2 | 5/2006 |

OTHER PUBLICATIONS

OR Saramaki, KP Parkka, RL Vessella, T Visakorpi. Genetic aberrations in prostate caner by microarray analysis. Int J Cancer 2006, vol. 119, p. 1322-1329.*
BCO1 Gene, GeneCards Human Gene Database 2016, http://www.genecards.org/cgi-bin/carddisp.pl?gene=BCO1, p. 1-13.*
MSC Gene, GeneCards Human Gene Database 2016, http://www.genecards.org/cgi-bin/carddisp.pl?gene=MSC, p. 1-15.*
XKR9 Gene, GeneCards Human Gene Database 2016, http://www.genecards.org/cgi-bin/carddisp.pl?gene=XKR9, p. 1-11.*
TRPA1 Gene, GeneCards Human Gene Database 2016, http://www.genecards.org/cgi-bin/carddisp.pl?gene=TRPA1, p. 1-16.*
EYA1 Gene, GeneCards Human Gene Database 2016, http://www.genecards.org/cgi-bin/carddisp.pl?gene=EYA1, p. 1-15.*
LACTB2 Gene, GeneCards Human Gene Database 2016, http://www.genecards.org/cgi-bin/carddisp.pl?gene=LACTB2, p. 1-14.*
KCNB2 Gene, GeneCards Human Gene Database 2016, http://www.genecards.org/cgi-bin/carddisp.pl?gene=KCNB2, p. 1-15.*
Michael J Heller. DNA Microarray Technology: devices, systems and applications. Annu Rev Biomed Eng 2002, vol. 4, p. 129-53.*
Liu, W. et al., "Comprehensive assessment of DNA copy number alterations in human prostate cancers using Affymetrix 100K SNP mapping array" Genes Chromosomes & Cancer (Aug. 8, 2006) pp. 1018-1032, vol. 45, No. 11.
Gorlov, I.P. et al., "Prioritizing genes associated with prostate cancer development" BMC Cancer, Biomed. Central (Nov. 2, 2010) pp. 599, vol. 10, No. 1.
Troutman, S.M. et al., "Prostate cancer genomic signature offers prognostic value" Cancer Biology & Therapy (Dec. 1, 2010) pp. 1079-1080, vol. 10, No. 11.
Pavelic, S.K. et al., "Metastasis: new perspectives on an old problem" Molecular Cancer (Feb. 22, 2011) pp. 22, vol. 10, No. 1.
Supplementary European Search Report dated Oct. 15, 2014 issued in European Application No. EP 12777398.4.
Barlett, J. et al., "Mammostrat® as a tool to stratisfy breast cancer patients at risk of recurrence during endocrine therapy" Breast Cancer Research (2010) pp. 1-11, vol. 12, No. 4:R47.
Barrett, T. et al., "NCBI GEO: archive for function genomics data sets—10 years on" Nucleic Acids Res. (2011) pp. D1005-D1010, vol. 39.
Beroukhim, R. et al., "The landscape of somatic copy-number alteration across human cancers" Nature (Feb. 18, 2010) pp. 899-905, vol. 463, No. 7283.

(Continued)

*Primary Examiner* — Olivia M. Wise
(74) *Attorney, Agent, or Firm* — Scully Scott Murphy & Presser, P.C.

(57) ABSTRACT

A method of determining the risk of metastasis of prostate cancer in a human subject who has or had prostate cancer is disclosed herein. The method is based on detecting in a prostate sample from the subject the number of copies per cell of genes and/or genomic regions of a metastatic gene signature set disclosed herein, and determining alternations in the number of copies per cell of the genes and/or genomic regions in the signature set, as compared to the number of copies per cell in non-cancer cells, thereby determining the risk of prostate cancer metastasis.

6 Claims, 7 Drawing Sheets

(56) References Cited

OTHER PUBLICATIONS

Boorjian, S.A. et al., "Long-Term Outcome After Radical Prostatectomy for Patients with Lymph Node Positive Prostate Cancer in the Prostate Specific Antigen Era" Journal of Urology (Sep. 2007) pp. 864-871, vol. 178, No. 3 Pt 1: discussion 70-1.

Bogaerts, J. et al., "Gene signature evaluation as prognostic tool: challenges in the design of the MINDACT trial" Nat Clin Pract Oncol (Oct. 2006) pp. 540-551, vol. 3, No. 10.

Castro, P. et al., "Genomic Profiling of Prostate Cancers from African American Men" Neoplasia (Mar. 2009) pp. 305-312, vol. 11, No. 3.

Celebiler, A. et al., "Predicting invasive phenotype with CDH1, CDH13, CD44, and TIMP3 gene expression in primary breast Cancer" Cancer Sci (Dec. 2009) pp. 2341-2345, vol. 100, No. 12.

Ekhterae, D. et al., "Bcl-2 decreases voltage-gated K1 channel activity and enhances survival in vascular smooth muscle cells" American Journal of Physiol Cell Physiol (2001) pp. C157-C165, vol. 281, No. 1.

Fan, X. et al., "Impact of system L amino acid transporter 1 (LAT1) on proliferation of human ovarian cancer cells: A possible target for combination therapy with anti-proliferative aminopeptidase inhibitors" Biochem Pharmacol (2010) pp. 811-818, vol. 80, No. 6.

Jemal, A. et al., "Cancer Statistics, 2009" CA Cancer J. Clin. (2009) pp. 225-249, vol. 59, No. 4.

Imai, H. et al, "L-Type amino acid transporter 1 expression is a prognostic marker in patients with surgically resented stage 1 non-small cell lung cancer" Histopathology (2009) pp. 804-813, vol. 54, No. 7.

Kaira, K. et al., "L-Type amino acid transporter 1 and CD98 expression in primary and metastiatic sites of human neoplasms" Cancer Science (Dec. 2008) pp. 2380-2386, vol. 99, No. 12.

Kaji, M. et al., "Properties of L-Type Amino Acid Transporter 1 in Epidermal Ovarian Cancer" International Journal of Gynecol Cancer (Apr. 2010) pp. 329-336, vol. 20, No. 3.

Kim, C.S. et al., "BCH, an inhibitor of system L amino acid transporters, induces apoptosis in cancer cells" Biol Pharm Bull (2008) pp. 1096-1100, vol. 31, No. 6.

Klotz, L. et al., "Clinical Results of Long-Term Follow-Up of a Large, Active Surveillance Cohort With Localized Prostate Cancer" Journal of Clinical Oncology (Jan. 2010) pp. 126-131, vol. 28, No. 1.

Kobayashi, K. et al., "Enhanced Tumor Growth Elicited by L-Type Amino Acid Transporter 1 in Human Malignant Glioma Cells" Neurosurgery (Feb. 2008) pp. 493-503, vol. 62, No. 2, discussion 4.

Korn, J. et al., "Integrated genotype calling and association analysis of SNPs, common copy number polymorphisms and rare CNVs" Nat Genet (Oct. 2008) pp. 1253-1260, vol. 40, No. 10.

Laniado, M. et al., "Voltage-Gated K+ Channel Activity in Human Prostate Cancer Call Lines of Markedly Different Metastatic Potential: Distinguishing Characteristics of PC-3 and LNCaP Cells" Prostate (2001) pp. 262-274, vol. 46, No. 4.

Lapointe, J. et al., "Gennomic Profiling Reveals Alternative Genetic Pathways of Prostate Tumorigenesis" Cancer Res (2007) pp. 8504-8510, vol. 67, No. 18.

Liu, W. et al., "Copy number analysis indicates monoclonal origin of lethal metastatic prostate cancer" Nat Med (May 2009) pp. 559-565, vol. 15, No. 5.

Lu, Y. et al., "A Gene Expression Signature Predicts Survival of Patients with Stage I Non-Small Cell Lung Cancer" PLoS Med (Dec. 2006) pp. 2229-2243, vol. 3, No. 12:e467.

Michel, V. et al., "The solute carrier 44A1 is a mitochondrial protein andmediates choline transport" Faseb (2009) pp. 2749-2758, vol. J23, No. 8.

Nakagawa, T. et al., "A Tissue Biomarker Panel Predicting Systemic Progression after PSA Recurrence Post-Definitive Prostate Cancer Therapy" PLoS One (May 2008) pp. 1-14, vol. 3, No. 5:e2318.

Nicklin, P. et al., "Bidirectional Transport of Amino Acids Regulates mTOR and Autophagy" Cell (Feb. 2009) pp. 521-534, vol. 136, No. 3.

Oda, K. et al, "L-Type amino acid transporter 1 inhibitors inhibit tumor cell growth" Cancer Science (Jan. 2010) pp. 173-179, vol. 101, No. 1.

Ohori, M. et al., "Radical prostatectomy for carcinoma of the prostate" Mod Pathol. (2004) pp. 349-359, vol. 17, No. 3.

Parkinson, H. et al., "ArrayExpress update—an archive of microarray and high-throughput sequencing-based functional genomics experiments" Nucleic Acids Res (2011) pp. D1002-D1004, vol. 39.

Pinkel, D. et al., "Fluorescence in situ hybridization with human chromosome-specific libraries: Detection of trisomy 21 and translocations of chromosome 4" Proc. Natl. Acad. Sci. USA (Dec. 1988) pp. 9138-9142, vol. 85.

Ring, B. et al., "A novel five-antibody immunehistochemical test for subclassification of lung carcinoma" Mod Pathol (2009) pp. 1032-1043, vol. 22, No. 8.

Ring, B. et al., "Novel Prognostic Immunohistochemical Biomarker Panel for Estrogen Receptor-Positive Breast Cancer" Journal of Clinical Oncology (Jul. 2006) pp. 3039-3047, vol. 24, No. 19.

Sakata, T. et al., "L-type amino-acid transporter 1 as a novel biomarker for high-grade malignancy in prostate cancer" Pathol Int. (2009) pp. 7-18, vol. 59, No. 1.

Shelton, L. et al., "Glutamine targeting inhibits systemic metastasis in the VM-M3 murine tumor model" International Journal of Cancer (2010) pp. 2478-2485, vol. 127, No. 10.

Sun, J. et al., "DNA Copy Number Alterations in Prostate Cancers: A Combined Analysis of Published CGH Studies" Prostate (2007) pp. 692-700, vol. 67, No. 7.

Tanaka, H. et al., "Monoclonal antibody targeting of N-cadherin inhibits prostate cancer growth, metastasis and castration resistance" Nat Med (Dec. 2010) pp. 1414-1420, vol. 16, No. 12.

Taylor, B. et al., "Integrative Genomic Profiling of Human Prostate Cancer" Cancer Cell (Jul. 2010) pp. 11-22, vol. 18, No. 1.

Vanaja, D.K. et al., "Hypermethylation of Genes for Diagnosis and Risk Stratification of Prostate Cancer" Cancer Invest (2009) pp. 549-560, vol. 27, No. 5.

Yamauchi, K. et al, System L amino acid transporter inhibitor enhances anti-tumor activity of cisplatin in a head and neck squamous cell carcinoma cell line Cancer Letter (2009) pp. 95-101, vol. 276, No. 1.

Yilmaz, M. et al., "Mechanisms of Motility in Metastasizing Cells" Mol Cancer Res (2010) pp. 629-642, vol. 8, No. 5.

Zhang, L. et al., "Potassium channels and proliferation and migration of breast cancer cells" Acta Physiologica Sinica (Feb. 2009) pp. 15-20, vol. 6, No. 1.

Ahn, Jiyoung et al., "Prostate Cancer Predisposition Loci and Risk of Metastatic Disease and Prostate Cancer Recurrence", Clinical Cancer Research (Mar. 1, 2011), vol. 17, No. 5, pp. 1075-1081.

International Search Report dated Nov. 28, 2012 issued in PCT/US2012/035350.

Japanese Office Action dated Dec. 20, 2016 issued in Japanese Patent Application No. 2014-508576.

* cited by examiner

GENOMIC SIGNATURES OF METASTASIS IN PROSTATE CANCER

CROSS-REFERENCE TO RELATED APPLICATION

This application claims the benefit of priority of U.S. Provisional Application 61/479,914, filed Apr. 28, 2011, the entire contents of which are incorporated herein by reference.

STATEMENT REGARDING FEDERALLY SPONSORED RESEARCH OR DEVELOPMENT

This invention was made with government support under Grant No. CA158431 awarded by the National Institutes of Health. The government has certain rights in the invention.

FIELD OF THE DISCLOSURE

This disclosure relates to metastatic gene signatures. More particularly, this disclosure has identified copy number alterations (CNAs) around genes that are over-represented in metastases, which serve as the basis for predicting whether a primary tumor will metastasize.

BACKGROUND ART

Prostate cancer is a common public health problem. In 2010, this disease was diagnosed in an estimated 217,730 men (28% of all male cancers) and resulted in 32,050 deaths (11% of male cancer deaths) (Jemal et al., *CA Cancer J Clin* 59(4):225-49 (2009)). If left untreated, the majority of prostate cancers remain asymptomatic and indolent for decades (Klotz et al., *Journal of Clinical Oncology* (2010) 28:126-31). If treated with radical prostatectomy or radiation therapy, the risk of metastasis is reduced, but erectile dysfunction, urinary incontinence and rectal bleeding may occur, affecting the patient's quality of life. Because it is currently difficult to determine accurately which patients will develop metastatic disease, physicians treat patients with mid-to-late stage local disease aggressively, even when such treatment may not be required. Clinical parameters, such as serum concentration of prostate specific antigen (PSA), extension beyond surgical margins, invasion of seminal vesicles, extension beyond the capsule, Gleason score, prostate weight, race and year of surgery, are employed in existing nomograms for prediction of local recurrences (Ohori et al., *Mod Pathol* 17(3): 349-359 (2004)), but local recurrence and, therefore, these parameters have limited utility for predicting progression of the disease to distant sites (Nakagawa et al., *PLoS One* 3(5):e2318 (2008)). Development of a robust risk model that accurately predicts the potential of a local prostate cancer to metastasize would justify aggressive treatment in high-risk cases and improve the quality of life for men with indolent disease.

SUMMARY OF THE DISCLOSURE

This disclosure is directed to a method of determining the risk of metastasis of prostate cancer in a human subject who has or had prostate cancer. The method is premised in identification of metastatic signature genes and genomic regions whose copy number alterations are overrepresented in metastases.

In one embodiment, a metastatic gene signature set includes at least the top 80 genes and genomic regions shown in Table 6. In another embodiment, a metastatic gene signature set includes at least the top 40 genes and genomic regions shown in Table 6. In still another embodiment, a metastatic gene signature set includes at least the top 20 genes and genomic regions shown in Table 6. In yet another embodiment, a metastatic gene signature set includes at least the top 12 genes and genomic regions shown in Table 6.

In a specific embodiment, the method disclosed herein includes determining in a prostate sample from the subject the number of copies per cell of at least 12 genes and/or genomic regions of a metastatic gene signature set which consists of the top 20 genes and gene regions listed in Table 6; determining alternations in the number of copies per cell for each of the at least 12 genes and/or genomic regions as compared to the number of copies per cell in non-cancer cells; and determining the risk of prostate cancer metastasis based on the copy number alternations (CNAs) determined.

In one embodiment, the at least 12 genes and/or genomic regions being analyzed are the top 12 genes and genomic regions, namely, the PPP3CC genomic region, the SLCO5A1 genomic region, the SLC7A5 genomic region, the SLC7A2 genomic region, the CRISPLD2 genomic region, the CDH13 gene, the CDH8 gene, the CDH2 gene, the ASAH1 genomic region, the KCNB2 genomic region, the KCNH4 genomic region, and the CTD8 gene.

In another embodiment, the at least 12 genes and/or genomic regions being analyzed include all of the top 20 genes and genomic regions listed in Table 6, namely, the PPP3CC genomic region, the SLCO5A1 genomic region, the SLC7A5 genomic region, the SLC7A2 genomic region, the CRISPLD2 genomic region, the CDH13 gene, the CDH8 gene, the CDH2 gene, the ASAH1 genomic region, the KCNB2 genomic region, the KCNH4 genomic region, the CTD8 gene, the JPH1 genomic region, the MEST genomic region, the NCALD genomic region, the COL19A1 gene, the MAP3K7 genomic region, the YWHAG gene, the NOL4 genomic region, and the ENOX1 gene.

According to the method disclosed herein, an increase in the copy number per cell for any of the SLCO5A1 genomic region, the KCNB2 genomic region, the KCNH4 genomic region, the JPH1 genomic region, the NCALD genomic region, or the YWHAG gene, correlates with an increased risk of prostate cancer metastasis; and a decrease in the copy number per cell for any of the PPP3CC genomic region, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, or the ENOX1 gene, correlates with an increased risk of prostate cancer metastasis.

The copy number of a gene or genomic region can be determined using a nucleic acid probe that hybridizes to the gene or genomic region in the genomic DNA present in the sample. Hybridization can be performed in an array format, for example.

The risk of metastasis can be determined based on calculating a metastatic potential score:

$$M(SM) = \sum_{i}^{n} Zadjust_i * Dir_{sig}(i) * Dir_{samp}(i)$$

wherein the logistic adjusted Z-scores (Zadjust) for each of the genes of the metastatic signature set are set forth in Table 6 and wherein if the CNAs of the signature and the sample are in the same direction, the coefficient (Dir) will be 1; if they are in opposite directions, the coefficient will be –1; and if no alternation in copy number is detected for a gene, the coefficient for that gene=0; and comparing the metastatic potential score to a control value, wherein an increase in the score correlates with an increased risk of metastasis.

Further disclosed herein are diagnostic kits for performing the method of determining the risk of metastasis of prostate cancer. The kits can include nucleic acid probes that bind to one or more metastatic signature genes and genomic regions disclosed herein, and other assay reagents. The nucleic acid probes can be provided on a solid support such as a microarray slide. The kits can also include other materials such as instructions or protocols for performing the method.

DETAILED DESCRIPTION

Figure 1:
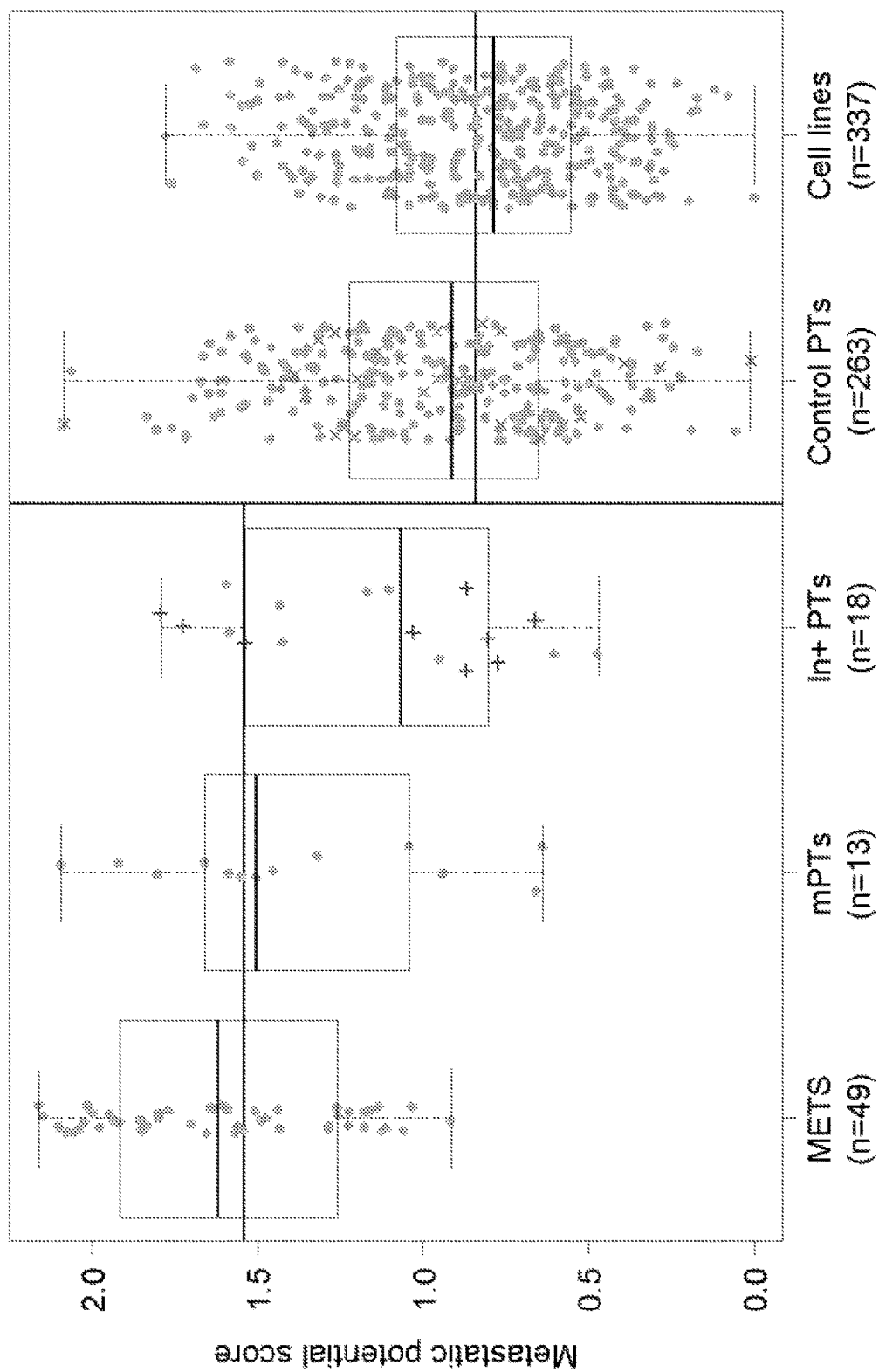
FIG. 1. Boxplot showing the metastatic potential scores for all samples involved in the analysis. All high-risk tumors are shown in the left three boxes (metastases, primary tumors that progressed to metastasis, and lymph node positive primary tumors), whereas unknown control primary tumors and the publically available cell line data are shown in the right boxes. The "+" symbols in the lymph node positive box represent those samples from the MSK dataset and indicate that there is no difference between the two lymph node positive cohorts. The "x" symbols in the control primary tumors plot represent selected low-risk primary tumors (individuals with no biochemical recurrence (PSA) for at least 80 months).

This disclosure provides a risk model that reliably predicts those tumors that are likely to metastasize, while minimizing the false positive rate and increasing the specificity of treatment decisions.

The risk model has been developed through the identification of copy number alterations (CNAs) around genes that were over-represented in metastases and primary tumors that later progressed to metastases. These CNAs are predictive of whether a primary tumor will metastasize. Cross-validation analysis has revealed a predictive accuracy of 80.5% and log rank analysis of the metastatic potential score has been shown to be significantly related to the endpoint of metastasis-free survival (p=0.014). The validation cases were comprised of bona fide mPTs (13 primary tumors that later developed into distant metastasis), whereas the validation controls were derived from a random sample of tumors (25% of the control MSK cohort) with unknown outcome. Neither of these cases or controls was used to train the model. In contrast to other reported risk models, the risk model disclosed herein based on the study of CNAs predicts distant metastasis progression as the clinical endpoint without the use of intermediate endpoints (such as biochemical markers of progression). The hierarchy of the genes and genomic regions that contribute to the prediction of metastatic potential has also been determined.

Accordingly, disclosed herein is a method for determining the risk of metastasis of prostate cancer in a human subject who has or had prostate cancer. This method is based on determining in a prostate sample from the subject, copy number alterations (CNAs) of genes and genomic regions of a metastatic gene signature set, and correlating the CNAs with a risk of prostate cancer metastasis.

Metastatic Gene Signature

Metastatic gene signatures have been developed by the present inventors from studies of the genomic landscape of copy number alterations in 294 primary prostate tumors and 49 prostate metastases from 5 independent cohorts, as described in more detail in the examples hereinbelow. 368 copy number alterations have been identified around genes that are over-represented in metastases and are predictive of whether a primary tumor will metastasize. Cross-validation analysis has revealed a prediction accuracy of 80.5%.

Accordingly, in one embodiment, this disclosure provides a metastatic gene signature set which includes the 368 genes identified herein, set forth in Table 6.

As displayed in Table 6, the 368 genes include a number of "clumps", each clump identified by a "Clump Index Number". A "clump", as used herein, refers to a group of genes that are adjacent to one another on the chromosome, and copy number alterations are detected for the genomic region which includes this group of genes in connection with prostate cancer metastasis. A multi-member clump may include both drivers (genes that cause or more directly associate with metastasis) and passengers (genes that indirectly associate with metastasis because of its close proximity of a metastasis driver gene).

The term "genomic region" is used herein interchangeably with the term "clump", and is typically used herein in conjunction with the name of a member gene within the genomic region or clump. For example, the PP3CC gene listed in the first row of Table 6 belongs to Clump Index 26, which also includes the genes KIAA1967, BIN3, SORBS3, PDLIM2, RHOBTB2, SLC39A14, EGR3, and C8orf58. Therefore, Clump Index 26 is also referred to herein as "the PP3CC genomic region".

While many of the 368 genes belong to clumps, some of the genes do not belong to any clump and copy number alterations have been identified specifically around each of these genes in connection with metastasis of prostate cancer. For example, as shown in Table 6 (with "NA" in the Clump Index column), CDH13, CDH8, CDH2 CTD8, COL19A1, YWHAG, and ENOX1, among many others, are genes which do not belong to any clump.

In other embodiments, this disclosure provides smaller metastatic gene signature sets which include at least 80, at least 40, at least 20, or at least 12, non-overlapping genes and/or genomic regions listed in Table 6.

By "non-overlapping" it is meant that the genes selected to constitute a smaller signature set do not belong to the same genomic region or clump.

As described in more detail in the examples hereinbelow, the metastatic potential score derived from the complete set of 368 genes resulted in a predictive accuracy of AUC=81%. The hierarchy of the genes that contribute to this prediction has been determined, as shown in Table 6, based on a procedure that sought to identify genes that maximize the prediction accuracy (AUC=81%) and also maximize the regression coefficient between the metastatic potential scores from the 368 genes versus any iteration of the randomly sampled subset of genes.

Accordingly, in one embodiment, a metastatic gene signature set includes at least the top 80 genes and genomic regions shown in Table 6.

In another embodiment, a metastatic gene signature set includes at least the top 40 genes and genomic regions shown in Table 6.

In still another embodiment, a metastatic gene signature set includes at least the top 20 genes and genomic regions shown in Table 6.

In yet another embodiment, a metastatic gene signature set includes at least the top 12 genes and genomic regions shown in Table 6.

Determination of Copy Number Alterations (CNAs)

A copy number alteration is a variation in the number of copies of a gene or genomic region present in the genome of a cell. A normal diploid cell typically has two copies of each chromosome and the genes contained therein. Copy number alterations may increase the number of copies, or decrease the number of copies.

The direction of copy number alteration for each of the 368 metastatic signature genes associated with metastasis is identified in Table 6 as −1 or 1, representing deletions and amplifications, respectively. For example, for the PP3CC genomic region (Clump Index 26), identified as "−1" in Table 6, deletions of this genomic region are overrepresented in metastatic prostate cancer or primary prostate cancers that later progressed to metastases, and are therefore indicative of a higher risk of metastasis of prostate cancer. Other genes and genomic regions whose deletions are predictive of a higher risk of metastasis of prostate cancer include, for example, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, and the ENOX1 gene. On the other hand, for the SLCO5A1 genomic region (Clump Index 33), identified as "1" in Table 6, amplifications of this genomic region are overrepresented in metastatic prostate cancer or primary prostate cancers that later progressed to metastases, and are therefore indicative of a higher risk of metastasis of prostate cancer. Other genes and genomic regions whose amplifications are indicative of a higher risk of metastasis of prostate cancer include, for example, the KCNB2 genomic region, the KCNH4 genomic region, the JPH1 genomic region, the NCALD genomic region, and the YWHAG gene.

To determine whether there is any copy number alteration for a given gene or genomic region, a prostate sample is obtained from a subject of interest. A prostate sample refers to a cell or tissue sample taken from the prostate of a subject of interest which sample contains genomic DNA to be analyzed for CNAs. Methods of procuring cell and tissue samples are well known to those skilled in the art, including, for example, tissue sections, needle biopsy, surgical biopsy, and the like. For a cancer patient, cells and tissue can be obtained from a tumor. A cell or tissue sample can be processed to extract, purify or partially purify, or enrich or amplify the nucleic acids in the sample for further analysis.

Nucleic acid probes are designed based on the genes and genomic regions of a metastatic signature gene set which permit detection and quantification of CNAs in the genes and genomic regions.

In one embodiment, the probes are composed of a collection of nucleic acids that specifically hybridize to the full set of 368 genes of the metastatic signature gene set.

In another embodiment, the probes are composed of a collection of nucleic acids that specifically hybridize to the top 80 genes and genomic regions shown in Table 6.

In still another embodiment, the probes are composed of a collection of nucleic acids that specifically hybridize to the top 40 genes and genomic regions shown in Table 6.

In yet another embodiment, the probes are composed of a collection of nucleic acids that specifically hybridize to the top 20 genes and genomic regions shown in Table 6.

In a further embodiment, the probes are composed of a collection of nucleic acids that specifically hybridize to the top 12 genes and genomic regions shown in Table 6.

By "specifically hybridize" it is meant that a nucleic acid probe binds preferentially to a target gene or genomic region under stringent conditions, and to a lesser extent or not at all to other genes or genomic regions.

"Stringent conditions" in the context of nucleic acid hybridization are known in the art, e.g., as described in Sambrook, *Molecular Cloning: A Laboratory Manual* ($2^{nd}$ ed.) vol. 1-3, Cold Spring Harbor Laboratory, Cold Spring Harbor Press, New York (1989). Generally, highly stringent hybridization and wash conditions are selected to be about 5° C. lower than the thermal melting point for a specific sequence at a defined ionic strength and pH. An example of highly stringent hybridization conditions is 42° C. in standard hybridization solutions. An example of highly stringent wash conditions include 0.2×SSC at 65° C. for 15 minutes. An example of medium stringent wash conditions is 1×SSC at 45° C. for 15 minutes. An example of a low stringency wash is 4×-6×SSC at room temperature to 40° C. for 15 minutes.

Nucleic acid probes for purposes of this invention should be at least 15 nucleotides in length to permit specific hybridization to a target gene or genomic region, and can be 50, 100, 200, 400, 600, 800, 1000, or more nucleotides in length, or of a length ranging between any of the two above-listed values. A nucleic acid probe designed to specifically hybridize to a target gene can include the full length sequence or a fragment of the gene. A nucleic acid probe designed to specifically hybridize to a specific target genomic region can include at least a fragment of the genomic region, e.g., at least the full length sequence or a fragment of a gene (any gene) within the genomic region. Alternatively, a nucleic acid probe shares at least 80%, 85%, 90%, 95%, 98%, 99% or greater sequence identity with the target gene to permit specific hybridization.

The hybridized nucleic acids can be detected by detecting one or more labels attached to the sample or probe nucleic acids. The labels can be incorporated by a variety of methods known in the art, and include detectable labels such as magnetic beads, a fluorescent compound (e.g., Texas red, rhodamine, green fluorescent protein and the like), radio isotope, enzymes, colorimetric labels (e.g., colloidal gold particles). In other embodiments, the sample or probe nucleic acids can be conjugated with one member of a binding pair, and the other member of the binding pair is conjugated with a detectable label. Binding pairs suitable for use herein include biotin and avidin, and hapten and a hapten-specific antibody.

A number of techniques for analyzing chromosomal alterations are well known in the art. For example, fluorescence in-situ hybridization (FISH) can be used to study copy numbers of individual genetic loci or regions on a chromosome. See, e.g., Pinkel et al., Proc. Natl. Acad. Sci. USA 85: 9138-9142 (1988). Comparative genomic hybridization (CGH) can also be used to detect copy number alterations of chromosomal regions. See, e.g., U.S. Pat. No. 7,638,278.

In some embodiments, hybridization is performed on a solid support. For example, probes that specifically hybridize to signature genes and genomic regions can be spotted or immobilized on a surface, e.g., in an array format, and subsequently samples containing genomic DNA are added to the array to permit specific hybridization.

Immobilization of nucleic acid probes on various solid surfaces and at desired densities (e.g., high densities with each probe concentrated in a small area) can be achieved by using methods and techniques known in the art. See, e.g., U.S. Pat. No. 7,482,123 B2. Examples of solid surfaces include nitrocellulose, nylon, glass, quartz, silicones, polyformaldehyde, cellulose, cellulose acetate; and plastics such as polyethylene, polypropylene, polystyrene, and the like; gelatins, agarose and silicates, among others. High density immobilization of nucleic acid probes are used for high complexity comparative hybridizations which will reduce the total amount of sample nucleic acids required for binding to each immobilized probe.

In some embodiments, the arrays of nucleic acid probes can be hybridized with one population of samples, or can be used with two populations of samples (one test sample and one reference sample). For example, in a comparative genomic hybridization assay, a first collection of nucleic acids (e.g., sample from a possible tumor) is labeled with a first label, while a second collection of nucleic acids (e.g., control from a healthy cell or tissue) is labeled with a second label. The ratio of hybridization of the nucleic acids is determined by the ratio of the two labels binding to each member in the array. Where there are genomic deletions or amplifications, differences in the ratio of the signals from the two labels will be detected and provide a measure of the copy number.

Determination of Risk

Once copy number alterations for each of a metastatic signature gene set have been determined, the risk for metastasis can be correlated with the copy number alterations detected. An increase in the copy number per cell of the sample for one or more of the genes or genomic regions of a metastatic signature gene set disclosed herein, whose amplifications have been associated with metastatic prostate cancer, will indicate a higher risk of metastasis as compared to a control (e.g., a sample obtained from a healthy individual) in which no increase in the copy number occurs. On the other hand, a decrease in the sample in the copy number for one or more of the genes or genomic regions of a metastatic signature gene set disclosed herein, whose deletions have been associated with metastatic prostate cancer, will indicate a higher risk of metastasis as compared to a control in which no decrease in the copy number is observed.

For example, for a metastatic signature gene set composed of the top 20 genes and genomic regions listed in Table 6, an increase in the copy number per cell of the sample for all of the SLCO5A1 genomic region, the KCNB2 genomic region, the KCNH4 genomic region, the JPH1 genomic region, the NCALD genomic region, and the YWHAG gene, and a decrease in the sample in the copy number per cell of the sample for all of the PPP3CC genomic region, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, and the ENOX1 gene, correlate with an increased risk of prostate cancer metastasis. However, it is not necessary for all the genes and genomic regions within a signature set to change in the same direction as set forth in Table 6 in order to have a reasonably reliable prediction of the risk. That is, an increased risk can be predicted based on an increase in the copy number per cell of the sample for one or more, preferably a plurality of, the SLCO5A1 genomic region, the KCNB2 genomic region, the KCNH4 genomic region, the JPH1 genomic region, the NCALD genomic region, and the YWHAG gene, and/or a decrease in the sample in the copy number per cell of the sample for one or more, preferably a plurality of, the PPP3CC genomic region, the SLC7A5 genomic region, the SLC7A2 genomic region, the CRISPLD2 genomic region, the CDH13 gene, the CDH8 gene, the CDH2 gene, the ASAH1 genomic region, the CTD8 gene, the MEST genomic region, the COL19A1 gene, the MAP3K7 genomic region, the NOL4 genomic region, or the ENOX1 gene. By "plurality" it is meant at least 10, 11, 12, 13, 14, 15, 16, 17, 18, 19 or 20 of the top 20 genes and gene regions listed in Table 6.

This disclosure also provides a quantitative measure of the risk based on the copy number alterations of a signature gene set disclosed herein. More specifically, the risk of metastasis has been found to correlate with a metastatic potential score calculated based on the formula:

$$M(SM) = \sum_{i}^{n} Zadjust_i * Dir_{sig}(i) * Dir_{samp}(i)$$

That is, for a particular gene or genomic region, if the CNA of the signature and the sample are in the same direction (amplified or deleted), the coefficient will be 1, the logistic adjusted Z-score (Zadjust) for this gene or genomic region will be added; if in opposing directions, the coefficient will be −1, the logistic adjusted Z-score (Zadjust) for the gene or genomic region will be substracted; and if Dirsamp(i)=0, then the entire term will not count towards the score. Thus, essentially, the logistic adjusted Z-scores from genes (i . . . n) that match the metastasis signature are added, whereas from genes that mismatch the signature are subtracted. The logistic adjusted Z-scores (Zadjust) for each of the 368 genes of the full metastatic signature set are found in Table 6.

The calculated metastatic potential score is compared to a reference distribution of samples (the metastatic potential score determined from a population of men with prostate cancer with metastasis-free survival clinical outcome information, also called herein "the reference metastatic potential score"). Such reference distributions can be predetermined or calculated side-by-side in the same experiment as the sample being investigated. In many of the embodiments, the reference metastatic potential score equals to or is approximately 1.0. Therefore, an increase in the metastatic potential score of a test subject as compared to the control score from the reference distributions is correlated with an increased risk of metastasis of prostate cancer. According to this disclosure, a one-point increase in the metastatic potential score corresponds to an odds ratio of 6.3 for progression to metastasis (p=0.01). In some embodiments, an increase in the metastatic potential score as compared to a reference score by at least about 0.5, 0.53, 0.56, 0.58, 0.6, 0.65, 0.7 or greater, is considered to represent a significantly high risk of metastasis.

The disclosed method for predicting the likelihood of distant metastases represents a significant advancement in the diagnosis and treatment of prostate cancer. This predictor may be important for correctly categorizing men at the time of diagnosis and can lead to a choice of therapy that would maximize their chances of survival and minimize adverse side effects if aggressive treatment can be avoided. Thus, both treatment outcomes and quality of life could be improved. In addition, because the proposed tool, tumor genomic analysis, is comprehensive for identifying the genetic changes that are associated with pathogenesis and metastases, there is a greater likelihood of selecting a sufficient number of markers that are both sensitive and specific predictors. Furthermore, because these genomic alterations are themselves susceptible to manipulation with drugs, radiation or other therapies, they could provide a basis for assessing intermediate endpoints, such as androgen sensitivity and response to radiation. Ultimately, copy number alterations could guide the development of individually tailored therapies, including for cancers other than prostate.

Diagnostic Kits

Further disclosed herein are diagnostic kits for performing the methods described herein. The kits can include any and all reagents such as nucleic acid probes that bind to one or more metastatic signature genes described above, and other assay reagents. The nucleic acid probes can be provided on a solid support such as a microarray slide. The kits can also include other materials such as instructions or protocols for performing the method, which can be provided in an electronic version, e.g., on a compact disk or the like.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1

This Example describes the methods and sample sources utilized for developing a predictive metastasis model.

Predictive Biomarkers

The method chosen for developing the predictive metastasis model was the analysis of copy number alterations (CNAs) in prostate cancers. These cancers have been known to harbor multiple genomic imbalances that result from CNAs (Beroukhim et al., *Nature* 463(7283):899-905 (2010); Sun et al., *Prostate* 67(7):692-700 (2007)). High-resolution measurements of CNAs have informative value—in some cases providing direct evidence for alterations in the quantity of normal, mutant or hybrid-fusion transcripts and proteins in the cancer cells. The resulting RNA transcripts and proteins may impact the fitness of the cell and provide the mechanisms necessary for travel, invasion and growth. From the multiple CNAs identified in tumors, CNA-based gene signatures were developed to predict the likelihood of a primary tumor progressing to metastasis.

Samples, Cohorts and Data

Four publically available prostate cancer cohorts and a fifth cohort reported here (GSE27105) were studied, as summarized in Table 1: 1) 294 primary tumors and matched normal tissue samples from NYU School of Medicine (NYU n=29), Baylor College of Medicine (Baylor n=20) (Castro et al., *Neoplasia* 11(3):305-12 (2009)), Memorial Sloan-Kettering Cancer Center (MSK n=181) (Taylor et al., *Cancer Cell* 18(1):11-22 (2010)), and Stanford University (SU n=64 (single normal tissue used to reference each tumor)) (LaPointe et al., *Cancer Res* 67(18):8504-10 (2007)); 2) 49 metastatic tumors and matched normal samples from Johns Hopkins School of Medicine (Hopkins n=13) (Liu et al., *Nat Med* 15(5):559-65 (2009)) and MSK (n=36) (Taylor et al., supra). Normal prostate and tumor tissues (NYU) were obtained from the Cooperative Prostate Cancer Tissue Resource (Table 2). Array data from the four publically available cohorts (Castro et al., supra; Taylor et al., supra; LaPointe et al., supra; Liu et al., supra) were downloaded from Gene Expression Omnibus (Barrett et al., *Nucleic Acids Res* 39 (Database issue): D1005-10 (2011)) (GSE12702, GSE14996, GSE6469, GSE21035). A public cell lines cohort of various tumor origins was obtained from the ArrayExpress database (Parkinson et al., *Nucleic Acids Res* 39 (Database issue): D1002-4) (E-MTAB-38) to determine if the gene signature and predictive model developed herein could be applicable to other cancers.

Sample Processing (NYU Cohort)

Genomic DNA (gDNA) was extracted using a Gentra DNA extraction kit (Qiagen). Purified gDNA was hydrated in reduced TE buffer (10 mM Tris, 0.1 mM EDTA, pH 8.0). The gDNA concentration was measured using the Nano-Drop™ 2000 spectrophotometer at optical density (OD) wavelength of 260 nm. Protein and organic contamination were measured at OD 280 nm and 230 nm, respectively. Samples that passed quality control thresholds were then run on a 1% agarose gel to assess the integrity of the gDNA. 500 ng of gDNA samples were run on the Affymetrix Human SNP Array 6.0 at the Rockefeller University Genomics Resource Center using standard operating procedures. Signal intensity data (.cel files) were processed using the Birdseed v2.0 software (Korn et al., *Nat Genet* 40(10):1253-60 (2008)).

Study Design

The case samples in this study were either metastatic tumors (METS) or primary tumors from men treated with radical prostatectomy that later progressed to form distant metastasis (mPTs). METS and mPTs are clearly discernable phenotypes that can be reliably classified as cases. The control samples were defined as primary tumors that had not progressed to form distant metastases following radical prostatectomy. Given that radical prostatectomy cures both indolent primary tumors (iPTs) that would not metastasize and primary tumors that would otherwise progress to form metastasis, if left untreated, the control primary tumors would actually represent a mix of iPTs and unrealized mPTs. Assuming a randomly sampled cohort, it is expected that approximately 30% of the control group of primary tumors would be unrealized mPTs. The methods developed herein required only the prior information of whether a sample was derived from a metastasis and were designed to be robust to the confounder of mixed phenotypes.

Metastasis Prediction Model Statistics

A weighted Z-score algorithm was developed to calculate a metastatic potential score (MPS) as described in Example 2, with a higher score indicating a greater likelihood of metastasis. The predictive power of the instant models was evaluated through cross-validation testing. Two prediction models were trained using a combination of four cohorts. The first model was trained using 49 primary tumors of unknown clinical outcome from NYU (n=29) and Baylor (n=20) and a metastasis cohort from Hopkins (n=13). The second model was trained using 75% of the MSK cohort of primary tumors of unknown outcome (n=126) along with a set of metastatic tumors (n=36). The gene signatures and MPS scores derived from these 2 models were combined to fit a logistic regression model and used to predict bona fide mPTs (primary tumors that later developed into distant metastasis) and a random sample of 25% control tumors from MSK cohort not used to train either model. Prediction accuracy was measured by the area under the receiver operating characteristic curve and Kaplan-Meier metastasis-free survival.

Example 2

This Example describes the analytical pipeline for developing a metastatic potential clinical risk model.

An analytical pipeline was developed using the R-statistical softwarel comprised of four main steps:

In step 1, copy number amplification and deletion events for each tumor genome were called. A tumor genome's signal intensity profile was referenced (subtracted) from its matched normal genome intensity profile resulting in a copy number profile for each tumor. Each sample's copy number profile was represented numerically as −1, 0 or 1 (deletion, no event, or amplification) for each genomic position assayed by the array. A summary metastasis profile (indexing high frequency events) was also created where −1 and 1 represent deletions and amplifications, respectively, observed in greater than 25% of the metastasis cohort.

In step 2, a bootstrap clustering method was employed to develop an initial grouping for the unknown primary tumors. The summary copy number profile for the metastasis samples was combined with the individual profiles from the unknown primary tumors and processed using hierarchical clustering (binary distance metric and complete clustering method). For each bootstrap iteration, a subset of primary tumors were sampled with replacement and scored 1 if they were in the same cluster as the metastasis profile, and 0 if they were in the other cluster. Using the results from 20,000 iterations of the clustering, a similarity index was generated for each sample, representing the number of times it fell in a cluster with the metastasis profile. A sample with a high score was considered to be more metastatic (mPT), while lower scoring tumors were more indolent (iPT). The similarity scores distributed throughout the possible range of values (0 to 1), allowing the formation of distinct groups of tumors with significant contrast between high and low metastatic distance.

In step 3, these mPT and iPT contrast groups were used to assess quantitative copy number differences on a probe basis. For each probe on the array, an enrichment score, E(x), was calculated, which represented the relative amount of amplifications versus deletions, observed in each subgroup (metastasis, mPT and iPT).

$$E(x) = \frac{(\#Amp - \#Del)}{\# \text{Samples}}$$

Next, the relative enrichment was modeled by contrasting the metastasis and mPT copy number alterations with those observed in the iPT group.

$$SM = e^{[E(METS) + q*E(mPT) - E(iPT)]}$$

The first two enrichment terms being summed were designed to assign a higher score when the METS and mPT samples had more amplifications than deletions. Greater amplification enrichment in the METS and mPTs resulted in higher scores. The third term was higher when the iPT samples exhibit the opposite effect (enrichment for deletions over amplifications). The middle term was multiplied by a data-driven coefficient, q, representing the average contribution of mPT on a probe basis. For example, probes that were amplified in all metastases and mPTs, but deleted in all iPTs would yield the highest possible score. Likewise, probes that were deleted in all metastasis and mPT samples, but amplified in all iPT samples, would also reach this maximum possible score. The probe scores were then aggregated by gene and a Z-score was calculated to assess each gene's score compared to the rest of the genome.

In the event that there are multiple Z-scores for each gene (see Table 6), corresponding to the various cohorts used to generate the 3 signatures. Therefore, each individual will have 3 different MPS's. The final MPS (shown in Table 6) is calculated by combining the 3 MPS s for each signature using a variation of the rank method described below.

The Z-adjust transforms each gene's Z-score derived from the above three steps to fit a logistic distribution through the following standard function:

$$Z_{adj} = \left( \frac{Z_i}{1 + e^{\frac{Z_{min} - Z_i}{2}}} - \frac{Z_i}{2} \right)$$

The purpose of this transformation is to minimize the effect of any individual gene's Z-score on the overall MPS (makes the score robust to outliers).

Finally, in step 4, to predict whether a local prostate tumor had the capability to form distant metastasis, a weighted-Z scoring risk model was developed based on a signature of the top set of CNAs overlapping genomic regions as determined by the significance of their selection model Z-scores. The significant genes (Z≥1.7) were used from step 3 as a cutoff point. The metastatic prediction risk model score was defined as the following:

$$M(SM) = \sum_{i}^{n} Zadjust_i * Dir_{sig}(i) * Dir_{samp}(i)$$

For each tumor profile, logistic adjusted Z-scores (Zadjust) from genes (i . . . n) that match the metastasis signature were added, whereas from genes that mismatch the signature were subtracted. As the direction component of the risk model score (Dir) reflects, if the CNAs of the signature and the sample are in the same direction, the coefficient will be 1; if they are in opposing directions, the coefficient will be −1; and if Dirsamp(i)=0, then the entire term will not count towards the score. For example, if a gene i, that is typically amplified in metastases and mPTs is also amplified in the unknown profile, that Z-score is added, whereas if gene i in the profile is deleted, as expected in iPTs, the Z-score is subtracted. Neutral genes that are neither amplified nor deleted in the unknown profile are not scored in this model.

Example 3

This Example describes the results achieved by the predictive metastasis model developed as described in Examples 1-2.

Metastatic Potential Score Distributions

Significant differences in the metastatic potential score were observed for the metastasis (p=1.03E-18) and mPT (p=0.005) groups, compared to the control primary tumors (FIG. 1 and Table 3). The metastatic potential score in the lymph node positive primary tumors (derived from the MSK (n=9) and SU (n=9) cohorts) did not differ significantly from the control tumor group ($P_{MSK}$=0.23, $P_{su}$=0.19, $P_{Combined}$=0.08), which reflected the marginal ability of this clinical parameter to predict distant metastasis (BOORJIAN et al., Journal of Urology 178(3 Pt 1): 864-70; discussion 70-1 (2007)). Consistent with our assumption that the control cohorts contained a fraction of mPTs, their metastatic potential score overlapped the range of the cases. Furthermore, control primary tumors that did not recur biochemically (as measured by PSA) after 80 months of follow-up, (represented by Xs in FIG. 1) were not correlated with the metastatic potential score. To determine whether other cancer types exhibited a similar metastatic landscape of CNAs to that observed in prostate cancer, the metastatic potential scores for 337 cancer cell lines were calculated. An overall distribution that overlapped with low-risk prostate primary tumors was observed (FIG. 1). However, 22 of the 337 cell lines emerged above the 75th percentile of the prostate primary tumors and metastases, ranked by MPS. These cell lines originated from tumors of the lung (n=10), breast (n=3), colon (n=2) and melanoma (n=2). Other singletons in this group of 22 cell lines originated from thyroid, rectum, pharynx, pancreas and kidney (Table 4).

Cross-Validation and Survival Analysis

Figure 2:
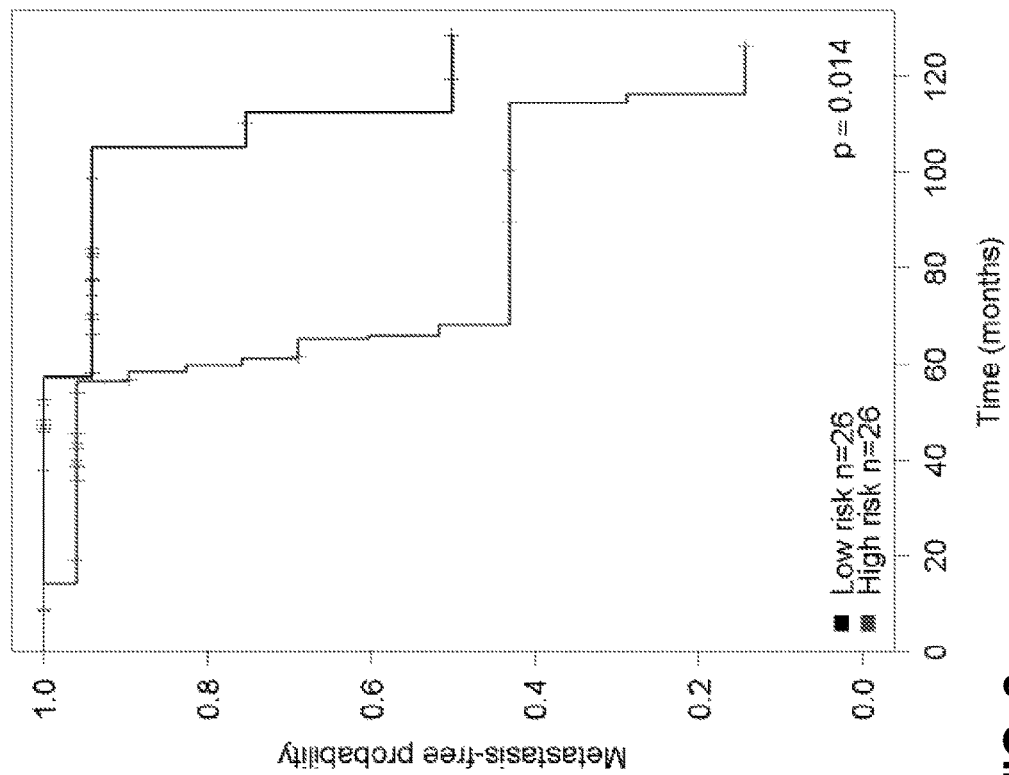
FIG. 2. Left graph, ROC-curve for prediction of primary tumors that progressed to metastasis using the metastatic potential score. The model used to make this prediction was run using a random 75% of samples from the data, whereas the prediction was run using the remaining 25% (13 known mPTs and 39 control primary tumors). The random model is indicated by the diagonal line (AUC=0.5). The crosshair indicates the cut point used to separate the data for survival analysis (shown in the right graph). Right graph, Kaplan-Meier survival curve showing metastasis-free probability. The data were split in half by metastatic potential score and progression status and follow-up time were assessed. Log rank test (p-value) compares the high-risk and low-risk sample groups.
Figure 2:
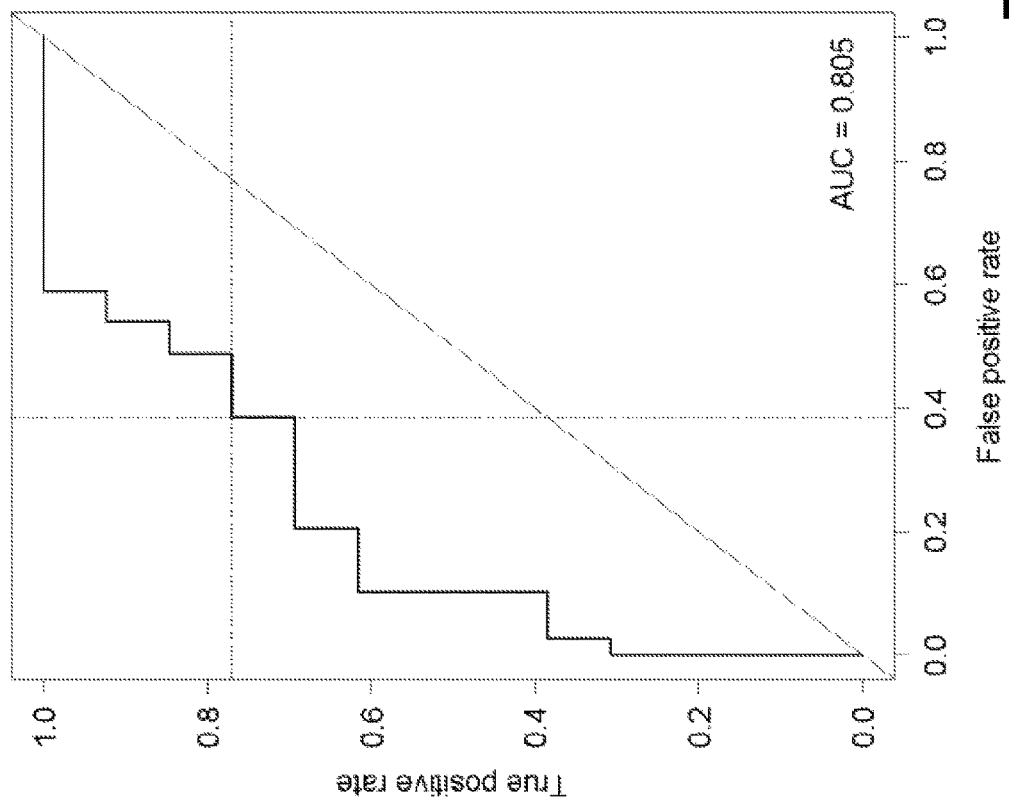

A cross-validation analysis predicting a subset of primary tumors (n=52) not used to train the model (n=13 mPTs and n=39 control primary tumors) resulted in an accuracy of 80.5% as measured by the area under the receiver operating characteristic curve (ROC-AUC) (FIG. 2, left graph). Considering that control primary tumors were a mixture of treated mPTs and iPTs, the quality of fit was believed to be an underestimate. Applying the instant prediction to a Kaplan-Meier analysis with the clinical endpoint of metastasis-free survival (FIG. 2, right graph) resulted in a significant separation (p=0.014) of the low-risk half of the cohort (based on the metastatic potential score) compared to the high-risk half. A one-point increase in the metastatic potential score corresponded to an odds ratio of 6.3 for progression to metastasis (p=0.01).

Biomarker Functional Significance

Many of the top ranking metastasis genes identified through the analysis have molecular functions related to alteration of nuclear and extra-cellular matrix structure and metabolic modification that enhance processes characteristic of metastasis, such as motility, invasion, and escape from anoikis A heat map of the CNA events of signature genes for all prostate tumors is suggestive of a path toward the different high frequency amplification versus deletion events that contrast the high-risk and low-risk tumors. The mid-risk region with its relative paucity of genomic events may represent the starting point of two alternative pathways of subsequent copy number alteration, one leading to metastasis and the other to an indolent state. The locking in of these 'anti-metastasis' events in indolent tumors may explain why they fail to metastasize despite extended periods of watchful waiting.

Many of the genes within these amplified or deleted regions from which the predictive signature was derived have been shown previously to play a role in prostate cancer metastasis. One of the top predictor genes, the solute carrier family SLC7A5 gene deleted on chromosome 16q24.2, encodes a neutral amino acid transporter protein (LAT1) that has been implicated in multiple cancers (prostate (Sakata et al., Pathol Int 59(1):7-18 (2009)), breast (Kaira et al., Cancer Science 99(12):2380-6 (2008)), ovarian (Kaji et al., International Journal of Gynecol Cancer 20(3):329-36 (2010)), lung (Imai et al., Histopathology 54(7):804-13 (2009)) and brain (Kobayashi et al., Neurosurgery 62(2): 493-503; discussion -4 (2008))) and has been shown to have utility as a diagnostic (Bartlett et al., Breast Cancer Research 12(4): R47 (2010); Ring et al., Mod Pathol 22(8): 1032-43 (2009); Ring et al., Journal of Clinical Oncology 24(19):3039-47 (2006)) and drug target in cell line (Fan et al., Biochem Pharmacol 80(6):811-8 (2010); Yamauchi et al., Cancer Letter 276(1):95-101 (2009); Kim et al., Biol Pharm Bull 31(6):1096-100 (2008)) and pre-clinical animal models (Oda et al., Cancer Science 101(1):173-9 (2010)). The normal function of LAT1 is to regulate cellular amino acid concentrations—L-glutamine (efflux) and L-leucine (influx). Reduced activity of LAT1 results in increased concentrations of L-glutamine which has been shown to constitutively fuel mTOR activity (Nicklin et al., Cell 136 (3):521-34 (2009)) and targeting of glutamine utilization through the use of a glutamine analog, dramatically reduced tumor growth and metastasis in cellular and in vivo mouse models (Shelton et al., International Journal of Cancer 127(10):2478-85). Five other solute carrier superfamily members (SLC7A2, SLC9A9, SLC26A7, SLC39A14, and SLCO5A1) were predictive of metastatic potential in the models disclosed herein. A ninth SLC gene, SLC44A1, encoding a choline transporter (Michel et al., Faseb J 23(8):2749-58 (2009)), was identified as part a of a 17-gene expression signature, comparing prostate primary tumors of men treated with radical prostatectomy that metastasized versus men that recurred biochemically, but did not metastasize (Nakagawa et al., supra).

A second set of signature genes includes 6 Cadherin family members encoding calcium dependent cell adhesion glycoproteins (CDH2, CDH8, CDH13, CDH15, CDH17 and PCDH9). Many of the Cadherin family proteins have putative functions associated with metastasis progression (Yilmaz et al., Mol Cancer Res 8(5):629-42, 2010) and have been included in diagnostic panels (Celebiler et al., Cancer Sci 100(12):2341-5 (2009); Lu et al., PLoS Med 3(12): e467 (2006)). A recent study of monoclonal antibody treatment targeting CDH2 inhibited prostate cancer growth and metastasis in androgen independent prostate cancer xenograft models (Tanaka et al., Nat Med (2010) 16:1414-20).

A third set of 6 genes predicted to contribute to metastatic potential were potassium channels KCNB2, KCNQ3, KCNAB1, KCTD8, KCTD9 and KCNH4. Three other potassium channels reside in the highly amplified region between 8q13 and 8q24 (KCNS2, KCNV1 and KCNK9) that did not rank high in our analysis, but may have weak or modifier effects. High levels of cytoplasmic potassium ion concentration are maintained by BCL-2, a putative oncogene, through the inhibition of potassium channel transcription. These high levels were shown to inhibit a necessary precursor to the hallmark mitochondrial apoptotic cascade of membrane disruption and ensuing release of cytochrome C, caspase, and nuclease degradation of cellular components (Ekhterae et al., *American Journal of Physiol Cell Physiol* 2001; 281(1): C157-65 (2001)). Furthermore, another study has shown that the hyper-methylation status of potassium channel KCNMA1 (10q22.3) has predictive value for prostate cancer recurrence (Vanaja et al., *Cancer Invest* 27(5): 549-60 (2009)). The activity of voltage-gated potassium channels in prostate cancer cell lines LNCaP (low metastatic potential) and PC3 (high metastatic potential), were observed to be markedly different (Laniado et al., *Prostate* 46(4):262-74 (2001)). Mounting evidence has also been observed in the involvement of potassium channels and the migration of breast cancer cells (Zhang et al., *Sheng Li Xue Bao* 61(1):15-20 (2009)).

The complete set of metastasis signature genes used in the prediction model (n=368, Table 6) represent various subsets of functions, revealing a unique profile necessary for each tumor to progress to metastasis.

Example 4

Ranking Metastasis Genes on the Basis of Predictability

Figure 3:
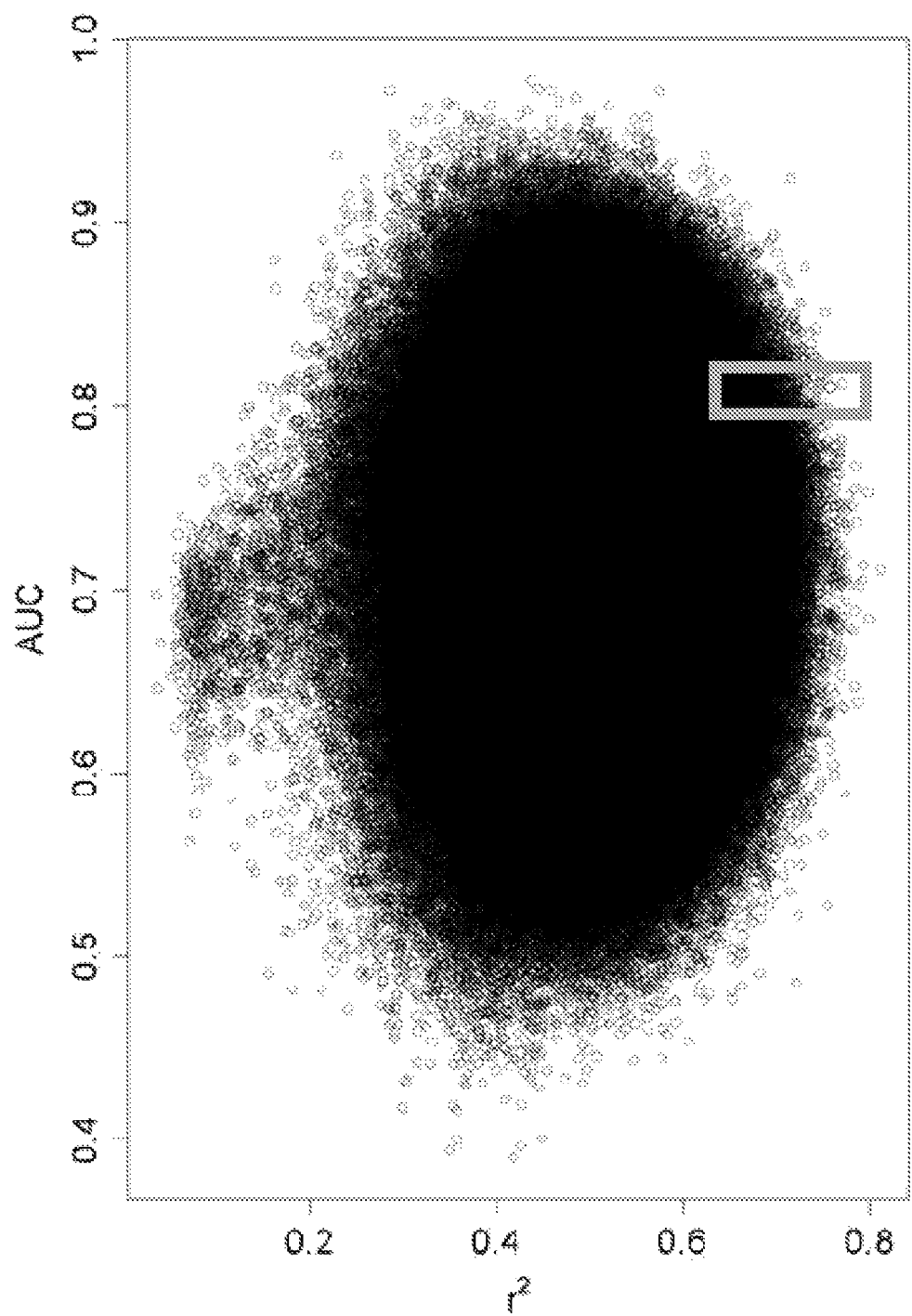
FIG. 3. Simulation of a subset of genes were sampled (n=20) and the genes that were over represented in the region where the AUC and r2 were maximized (box) were ranked by their frequency. This simulation was also performed for n=40, 50, 80, and 100 genes.

The metastatic potential score as derived from the complete set of 368 metastasis genes resulted in a predictive accuracy of AUC=81% in the cohort described in Examples 1-3. To determine the hierarchy of the genes that contribute to this prediction, several simulations (K) were performed by randomly sampling subsets genes (n) from the 368 genes, where n=20, 40, 50, 80, 100. This procedure sought to identify those genes that maximize the prediction accuracy (AUC=81%) while also maximizing the regression coefficient between the MPS scores from the 368 genes versus any random iteration of the randomly sampled subset of genes. For example a random subset of 20 genes that achieves a prediction accuracy=81% and an $r^2$=1.0 compared to the MPS derived from the 368 gene signature would achieve the theoretical best performance (FIG. 3).

Once gene rankings for the 5 simulations were determined, ranks G positions across K analyses were evaluated using a non-parametric ranking method (Breitling et al., *FEBS Lett* 573: 83-92, (2004)):

$$R(G) = \sum_{i=1}^{k} \log\left(\frac{1}{G_k}\right)$$

This method was selected as an improvement to a simple average of the ranks of each G across the k analyses because it gives more emphasis to having a high rank in any one of the analyses, regardless of rank in the others. This model of rank integration gives more weight, for example, to a gene ranked #1 and #100 in two different analyses than to a gene ranked #100 in each.

Figure 4:
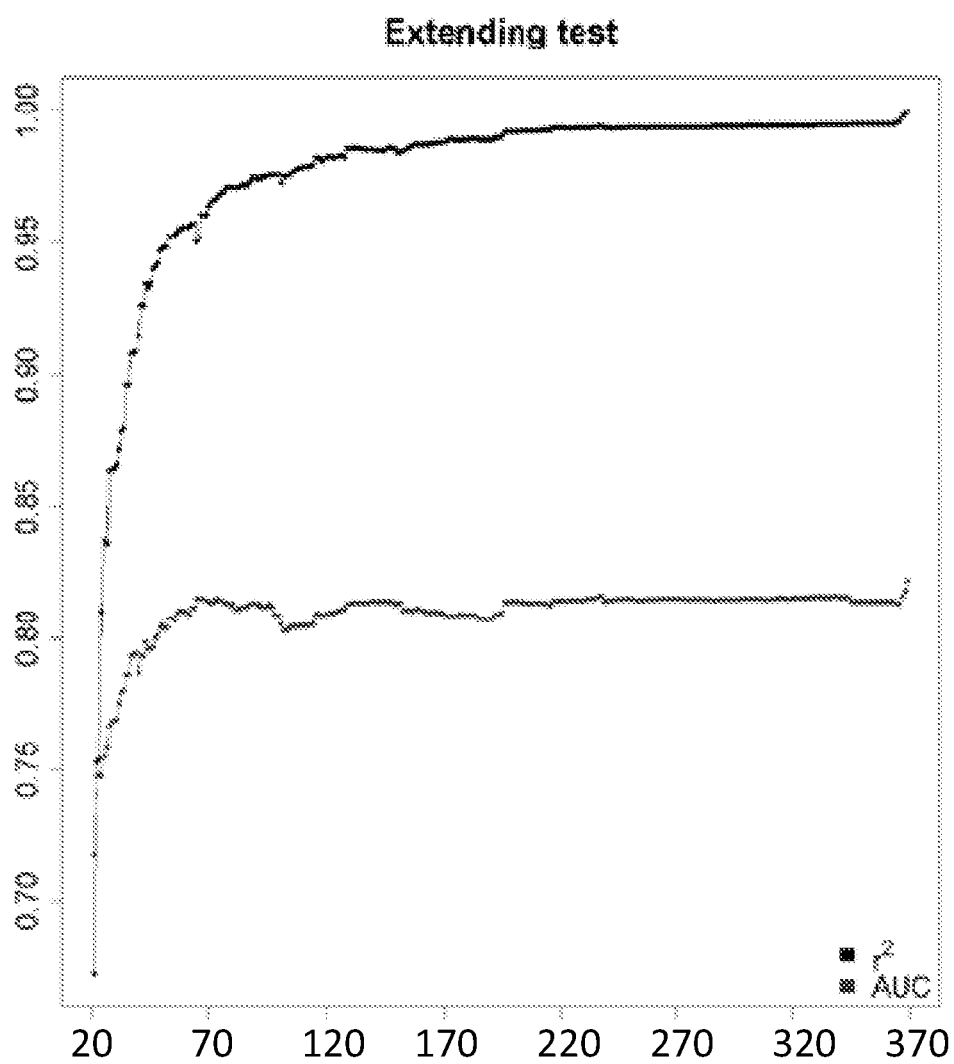
FIG. 4. Extending window-AUC (red), extending window-r2 (black) based on the sorted hierarchy of genes.

To evaluate the performance of this method, the composite ranked hierarchy of genes was assessed using an extending window. Starting with a minimum of 12 genes, and adding one gene every iteration, an AUC and r2 were calculated. The results in FIG. 4 show that the AUC plateaus at ~80 genes, achieving the optimal AUC ~0.81 and r2>0.95. Specifically, Table 5 shows the results for the top 12, 20, 40, 80 and 100 genes.

The ranking of the 368 genes is shown in Table 6.

Example 5

Reporting Prediction to Patients

Figure 5:
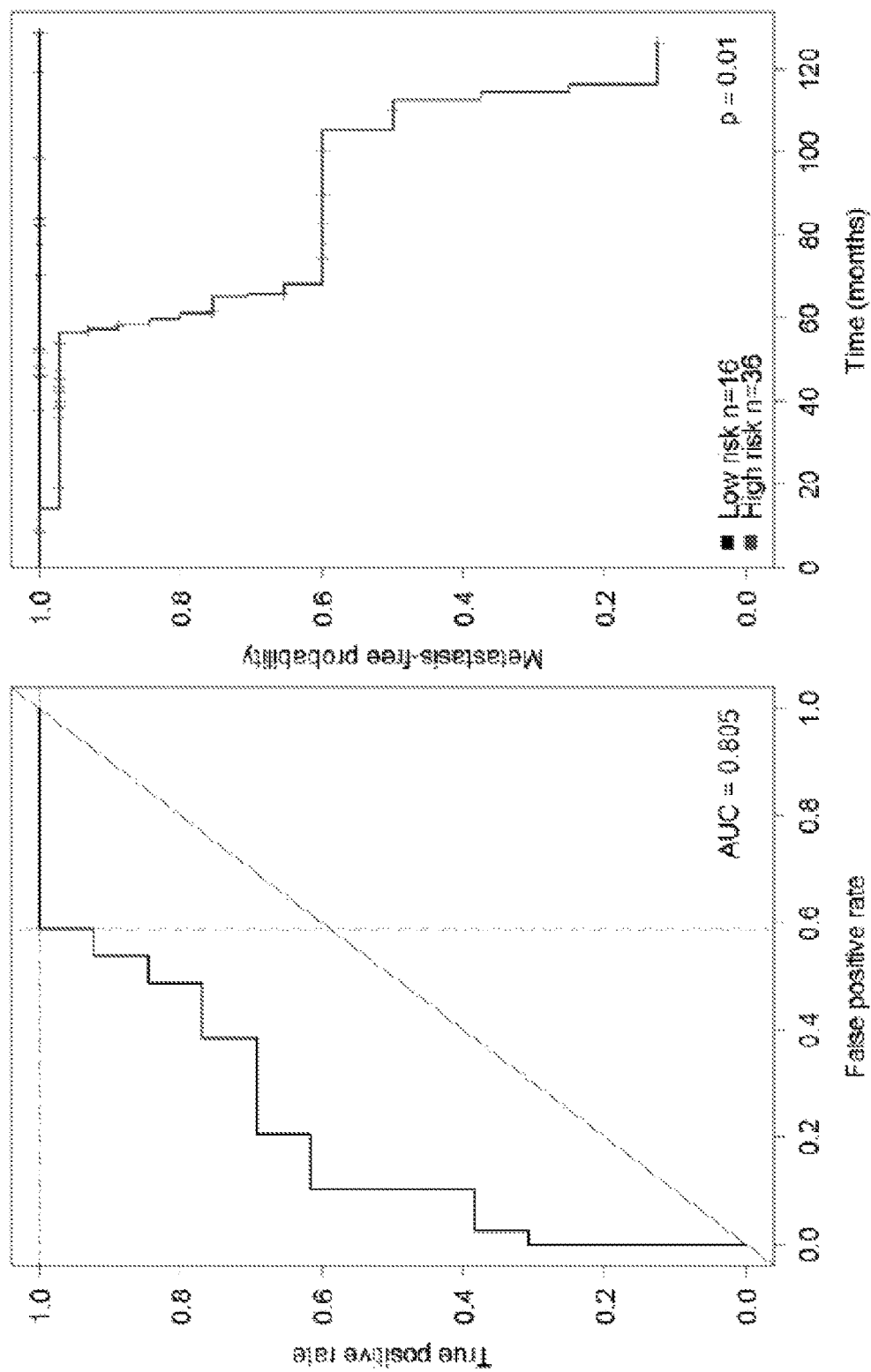
FIG. 5. ROC curve (left panel). Kaplan-Meier depiction of Cox proportional hazards model (right panel).

The prostate cancer metastatic potential score, assessed through a Cox proportional hazards ratio model provides the basis for determining metastasis-free probability. In FIG. 5 (left panel, ROC curve), a conservative threshold that maximizes our sensitivity (at 100% or 1.0 on the Y-axis of the ROC curve) was chosen to identify all true positives (i.e. men that will progress to metastasis). Within this high-risk group there is a false positive rate of 59% (men who would not otherwise have developed metastasis), which will result in some men with low-risk prostate cancer to be treated aggressively. However, currently 100% of the men are treated aggressively, so the conservative threshold herein would enable 31% of them to be spared aggressive treatment.

Applying this conservative threshold to a Kaplan-Meier analysis of a Cox proportional hazards model (FIG. 5, right panel) results in low risk and high risk probabilities of metastasis free survival at various time intervals. Therefore, for this model, a man with a low risk designation will have a very low (<5%) chance to develop metastasis in 10 years. While the high risk designation results in a 40% chance of progressing to metastasis in 60 months and a>90% chance of progressing to metastasis in 10 years.

As a comparison, the FDA approved breast cancer gene expression signature diagnostic "MammaPrint" uses similar Cox proportional hazards analysis to develop their risk reporting strategy (Bogarts et al., *Nat Clin Pract Oncol* 3:540-51, 2006). Currently, the FDA low risk assignment has a 10% chance of progressing to metastatic disease in 10 years, while the high risk assignment has a 29% chance of progressing in 10 years.

Example 6

Validation with Duke Cohort

To assess the validity of our metastasis signature and metastatic potential score (MPS) prediction model, the inventors collected a retrospective cohort of primary prostate cancer tumor and matched normal tissues from thirty men treated with radical prostatectomy at Duke University Medical Center (Duke cohort). The cancer tissue was obtained from archived formalin fixed paraffin embedded (ffpe) blocks. Each block was processed by pathologist by obtaining a 5 micron H&E stained sections and evaluated for tumor content. The genomic DNA (gDNA) was extracted using a Qiagen ffpe gDNA column extraction kit. The material was sent to Affymetrix Service Center in Santa Clara, Calif. and run on the Oncoscan™ V2 SNP array developed specifically for gDNA samples extracted from ffpe archived tissue. The array has approximately 300 thousand probes (see Table 7), most of which overlapped with the gene signature developed previously with other array platforms.

The Duke cohort was made up of primary tumors that metastasized following radical prostatectomy (mPTs, n=13), a group of high risk tumors that didn't develop distant metastases (hiPTs, n=8), and, a group of low risk tumors that didn't develop distant metastases (iPTs, n=7). The high risk designation of the hiPT/iPT groups was assigned based on whether the patient experienced biochemical recurrence and received adjuvant radiation and/or hormone therapy after surgery.

Figure 6:
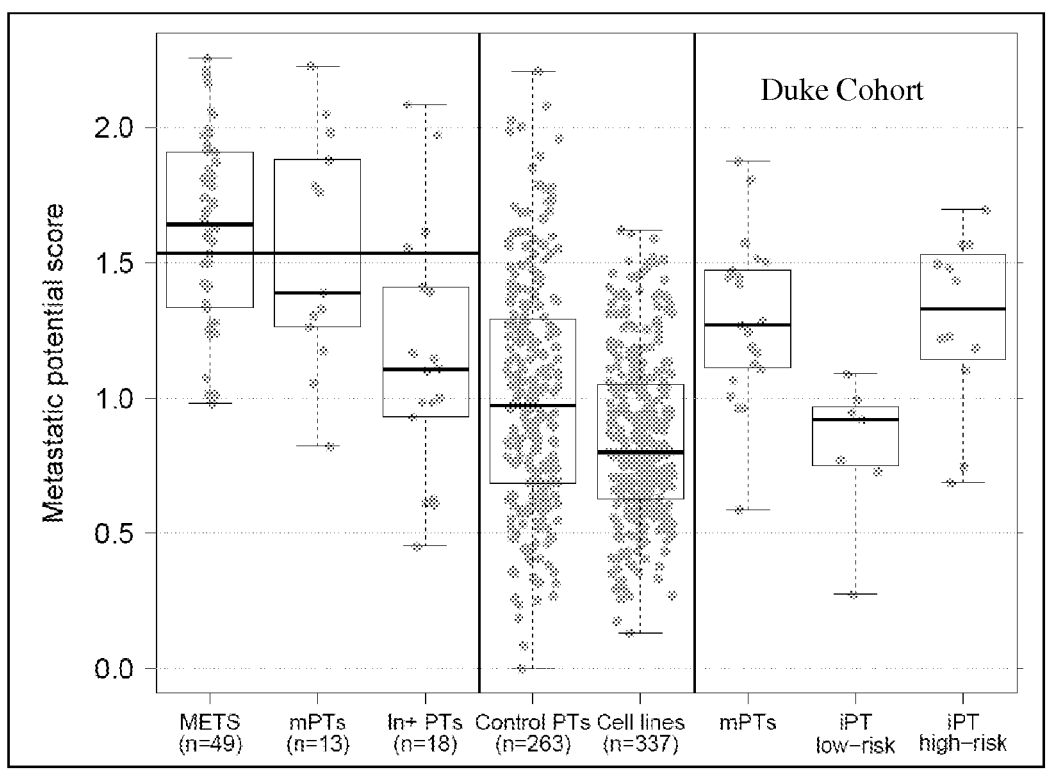
FIG. 6. Boxplots of MPS score (Y-axis) of primary tumor samples from the Duke cohort validation study (right panel) shown relative to previously studied cohorts (left and middle panels).
Figure 7:
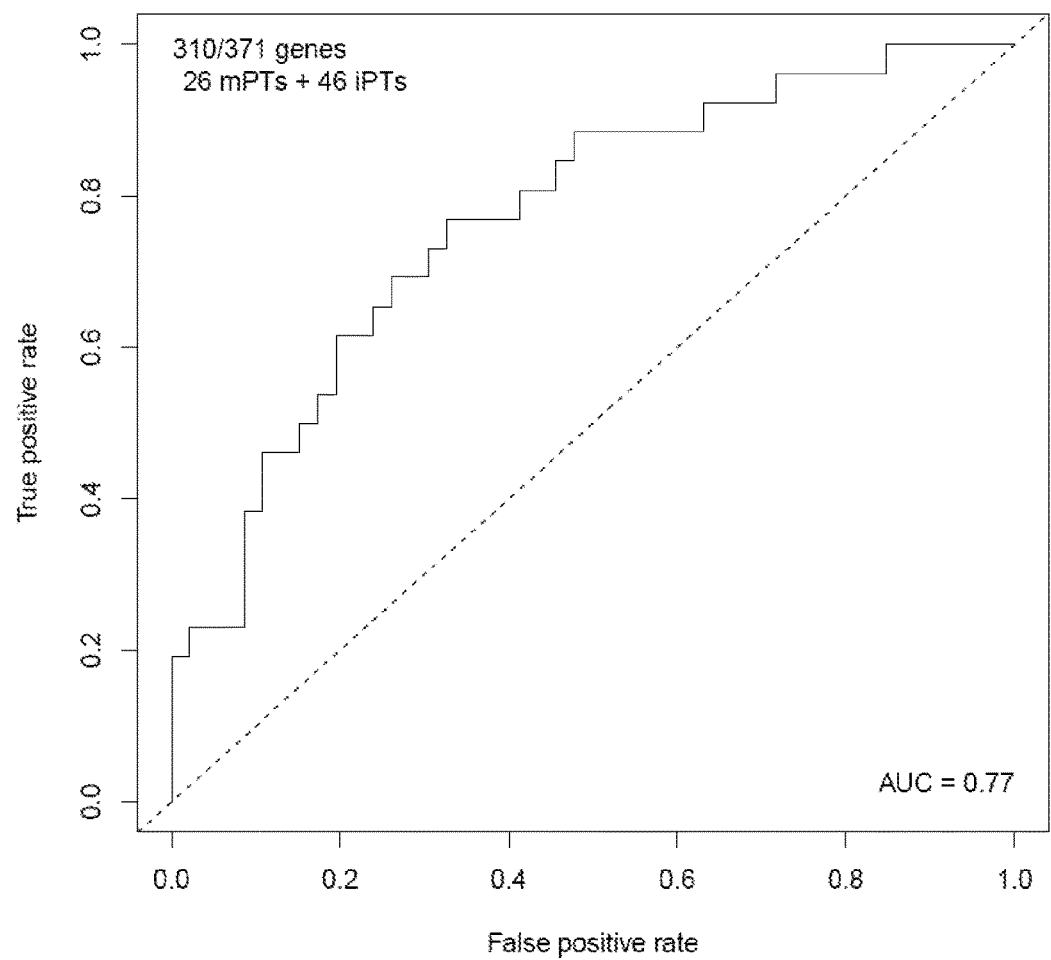
FIG. 7. Pooled ROC-AUC analysis of MSK and Duke validation samples.

The MPS score was calculated for the Duke cohort (FIG. 6) and shown to distribute as expected for mPTs, iPTs and hiPTs. The receiver operating characteristics-area under the curve analysis (ROC-AUC) applied only to the Duke cohort mPTs and iPTs resulted in an accuracy of 0.91. The Duke cohort mPTs and iPTs were pooled with the msk validation set (previously described), resulted in a 0.77 accuracy as measured by the ROC-AUC (FIG. 7).

TABLE 1

Prostate cancer cohorts

| Cohort | Cases (n) | Controls (n) | Pathological Stage | GEO-Accession | Array CGH Platform |
|---|---|---|---|---|---|
| NYU Langone Medical Center | 0 | 29 | T2C-T4 | GSE27105* | Affy V6 |
| Johns Hopkins School of Medicine | METS (13) | 0 | METS | GSE14996 | Affy V6 |
| Baylor College of Medicine | 0 | 20 | T2C-T4 | GSE12702 | Affy 500K |
| Memorial Sloan-Kettering Cancer Center | mPTs(13)/METS (36)/LN-METS (9) | 159 | T2C-T4/METS | GSE21035 | Agilent 244A |
| Stanford University | LN-METS (9) | 55 | T2C-T4/METS | GSE6469 | custom cDNA |
| | 80 | 263 | | | |
| | Total tumors | 343 | | | |

TABLE 2

NYU cohort sample information

| compositeID | Race | tumor_type | Stage | Gleason (primary) | Gleason (secondary) | Age at prostatectomy (years) |
|---|---|---|---|---|---|---|
| CA_1 | CA | primary | T2c | 3 | 3 | 70 |
| CA_2 | CA | primary | T4 | 3 | 3 | 59 |
| AA_3 | AA | primary | T2c | 3 | 4 | 76 |
| CA_4 | CA | primary | T2c | 3 | 3 | 58 |
| CA_5 | CA | primary | T4 | 3 | 3 | 73 |
| CA_6 | CA | primary | T3a | 3 | 4 | 67 |
| CA_7 | CA | primary | T4 | 4 | 3 | 68 |
| CA_8 | CA | primary | T2c | 3 | 3 | 64 |
| CA_9 | CA | primary | T3a | 4 | 4 | 72 |
| CA_10 | CA | primary | T2b | 3 | 3 | 69 |
| CA_11 | CA | primary | T2c | 3 | 4 | 60 |
| CA_12 | CA | primary | T2c | 3 | 3 | 63 |
| CA_13 | CA | primary | T3a | 4 | 4 | 58 |
| CA_14 | CA | primary | T2c | 4 | 4 | 64 |
| CA_16 | CA | primary | T2c | 3 | 3 | 65 |
| CA_17 | CA | primary | T3b | 3 | 4 | 67 |
| CA_18 | CA | primary | T3a | 3 | 3 | 68 |
| CA_19 | CA | primary | T3a | 4 | 3 | 68 |
| CA_20 | CA | primary | T2a | 4 | 4 | 56 |
| AA_21 | AA | primary | T2b | 3 | 3 | 62 |
| AA_22 | AA | primary | T2b | 3 | 5 | 53 |
| AA_23 | AA | primary | T3a | 4 | 5 | 47 |
| AA_24 | AA | primary | T3b | 3 | 4 | 53 |
| AA_25 | AA | primary | T2b | 3 | 4 | 58 |
| CA_26 | CA | primary | T4 | 3 | 4 | 64 |
| AA_27 | AA | primary | T2b | 3 | 3 | 64 |
| AA_28 | AA | primary | T2b | 3 | 3 | 62 |
| AA_29 | AA | primary | T2b | 3 | 3 | 67 |
| CA_30 | CA | primary | T2b | 3 | 4 | 45 |

TABLE 3

Prostate tumor metastatic potential score

| sampleID | MPS | cohort | subgroup |
|---|---|---|---|
| M_3 | 1.70 | Hopkins | METS |
| M_16 | 1.18 | Hopkins | METS |
| M_17 | 1.14 | Hopkins | METS |
| M_19 | 1.26 | Hopkins | METS |
| M_21 | 1.51 | Hopkins | METS |
| M_22 | 1.54 | Hopkins | METS |
| M_24 | 1.26 | Hopkins | METS |
| M_28 | 1.92 | Hopkins | METS |
| M_30 | 1.18 | Hopkins | METS |
| M_31 | 1.85 | Hopkins | METS |
| M_32 | 1.85 | Hopkins | METS |
| M_33 | 1.29 | Hopkins | METS |
| M_34 | 1.49 | Hopkins | METS |
| CA_1 | 0.80 | NYU | PT Control |
| CA_2 | 0.48 | NYU | PT Control |
| AA_3 | 1.61 | NYU | PT Control |
| CA_4 | 1.54 | NYU | PT Control |
| CA_5 | 0.65 | NYU | PT Control |
| CA_6 | 1.38 | NYU | PT Control |
| CA_7 | 1.39 | NYU | PT Control |
| CA_8 | 0.72 | NYU | PT Control |
| CA_9 | 1.49 | NYU | PT Control |
| CA_10 | 0.77 | NYU | PT Control |
| CA_11 | 0.75 | NYU | PT Control |
| CA_12 | 0.90 | NYU | PT Control |
| CA_13 | 0.58 | NYU | PT Control |
| CA_14 | 0.89 | NYU | PT Control |
| CA_16 | 0.67 | NYU | PT Control |
| CA_17 | 0.86 | NYU | PT Control |
| CA_18 | 0.76 | NYU | PT Control |
| CA_19 | 1.30 | NYU | PT Control |
| CA_20 | 0.19 | NYU | PT Control |
| AA_21 | 0.25 | NYU | PT Control |
| AA_22 | 1.53 | NYU | PT Control |

TABLE 3-continued

Prostate tumor metastatic potential score

| sampleID | MPS | cohort | subgroup |
|---|---|---|---|
| AA_23 | 0.29 | NYU | PT Control |
| AA_24 | 1.30 | NYU | PT Control |
| AA_25 | 0.91 | NYU | PT Control |
| CA_26 | 0.56 | NYU | PT Control |
| AA_27 | 0.83 | NYU | PT Control |
| AA_28 | 0.50 | NYU | PT Control |
| AA_29 | 0.52 | NYU | PT Control |
| CA_30 | 1.31 | NYU | PT Control |
| AAN_24 | 0.90 | Baylor | PT Control |
| AAN_25 | 1.42 | Baylor | PT Control |
| AAN_27 | 0.87 | Baylor | PT Control |
| AAN_31 | 1.25 | Baylor | PT Control |
| AAN_45 | 1.30 | Baylor | PT Control |
| AAN_52 | 0.47 | Baylor | PT Control |
| AAN_58 | 1.18 | Baylor | PT Control |
| AAN_60 | 0.97 | Baylor | PT Control |
| AAN_75 | 0.50 | Baylor | PT Control |
| AAN_110 | 0.53 | Baylor | PT Control |
| AAN_115 | 0.43 | Baylor | PT Control |
| AAN_122 | 1.05 | Baylor | PT Control |
| AAN_128 | 1.36 | Baylor | PT Control |
| AAN_137 | 0.17 | Baylor | PT Control |
| AAN_138 | 0.87 | Baylor | PT Control |
| AAN_240 | 1.24 | Baylor | PT Control |
| AAN_154 | 1.15 | Baylor | PT Control |
| AAN_167 | 1.31 | Baylor | PT Control |
| AAN_80 | 1.01 | Baylor | PT Control |
| AAN_96 | 1.15 | Baylor | PT Control |
| GSM525575 | 1.67 | MSK | PT Control |
| GSM525576 | 1.83 | MSK | PT Control |
| GSM525577 | 0.87 | MSK | In+ |
| GSM525578 | 1.27 | MSK | PT Control |
| GSM525579 | 1.39 | MSK | PT Control |
| GSM525580 | 1.20 | MSK | PT Control |
| GSM525581 | 0.01 | MSK | PT Control |
| GSM525582 | 0.76 | MSK | PT Control |
| GSM525583 | 0.65 | MSK | PT Control |
| GSM525584 | 1.76 | MSK | PT Control |
| GSM525585 | 0.65 | MSK | PT Control |
| GSM525586 | 0.52 | MSK | PT Control |
| GSM525587 | 0.83 | MSK | PT Control |
| GSM525588 | 1.14 | MSK | PT Control |
| GSM525589 | 0.79 | MSK | PT Control |
| GSM525590 | 1.07 | MSK | PT Control |
| GSM525591 | 0.58 | MSK | PT Control |
| GSM525592 | 1.36 | MSK | PT Control |
| GSM525593 | 1.23 | MSK | PT Control |
| GSM525594 | 1.30 | MSK | PT Control |
| GSM525595 | 1.46 | MSK | PT Control |
| GSM525596 | 0.78 | MSK | PT Control |
| GSM525597 | 1.34 | MSK | PT Control |
| GSM525598 | 0.82 | MSK | PT Control |
| GSM525599 | 0.76 | MSK | PT Control |
| GSM525600 | 1.54 | MSK | PT Control |
| GSM525601 | 0.76 | MSK | PT Control |
| GSM525602 | 1.80 | MSK | mPT |
| GSM525603 | 1.11 | MSK | PT Control |
| GSM525604 | 0.82 | MSK | PT Control |
| GSM525605 | 1.04 | MSK | mPT |
| GSM525606 | 2.09 | MSK | mPT |
| GSM525607 | 1.01 | MSK | PT Control |
| GSM525608 | 0.98 | MSK | PT Control |
| GSM525609 | 1.19 | MSK | PT Control |
| GSM525610 | 1.32 | MSK | PT Control |
| GSM525611 | 1.36 | MSK | PT Control |
| GSM525612 | 1.24 | MSK | PT Control |
| GSM525613 | 1.07 | MSK | PT Control |
| GSM525614 | 1.21 | MSK | PT Control |
| GSM525615 | 0.33 | MSK | PT Control |
| GSM525616 | 1.59 | MSK | mPT |
| GSM525617 | 1.15 | MSK | PT Control |
| GSM525618 | 1.79 | MSK | In+ |
| GSM525619 | 1.46 | MSK | mPT |
| GSM525620 | 1.16 | MSK | PT Control |
| GSM525621 | 0.77 | MSK | PT Control |
| GSM525622 | 1.70 | MSK | PT Control |
| GSM525623 | 0.96 | MSK | PT Control |
| GSM525624 | 0.36 | MSK | PT Control |
| GSM525625 | 1.22 | MSK | PT Control |
| GSM525626 | 2.08 | MSK | PT Control |
| GSM525627 | 0.71 | MSK | PT Control |
| GSM525628 | 0.64 | MSK | mPT |
| GSM525629 | 1.54 | MSK | In+ |
| GSM525630 | 0.57 | MSK | PT Control |
| GSM525631 | 1.27 | MSK | PT Control |
| GSM525632 | 0.37 | MSK | PT Control |
| GSM525633 | 1.01 | MSK | PT Control |
| GSM525634 | 1.32 | MSK | mPT |
| GSM525635 | 0.63 | MSK | PT Control |
| GSM525636 | 0.31 | MSK | PT Control |
| GSM525637 | 1.39 | MSK | PT Control |
| GSM525638 | 1.18 | MSK | PT Control |
| GSM525639 | 0.54 | MSK | PT Control |
| GSM525640 | 1.08 | MSK | PT Control |
| GSM525641 | 0.28 | MSK | PT Control |
| GSM525642 | 1.55 | MSK | PT Control |
| GSM525643 | 1.14 | MSK | PT Control |
| GSM525644 | 1.08 | MSK | PT Control |
| GSM525645 | 0.58 | MSK | PT Control |
| GSM525646 | 0.95 | MSK | PT Control |
| GSM525647 | 1.55 | MSK | mPT |
| GSM525648 | 1.00 | MSK | PT Control |
| GSM525649 | 0.70 | MSK | PT Control |
| GSM525650 | 0.96 | MSK | PT Control |
| GSM525651 | 0.98 | MSK | PT Control |
| GSM525652 | 0.89 | MSK | PT Control |
| GSM525653 | 0.66 | MSK | In+ |
| GSM525654 | 1.62 | MSK | PT Control |
| GSM525655 | 1.05 | MSK | PT Control |
| GSM525656 | 0.27 | MSK | PT Control |
| GSM525657 | 0.80 | MSK | In+ |
| GSM525658 | 0.67 | MSK | PT Control |
| GSM525659 | 0.92 | MSK | PT Control |
| GSM525660 | 0.53 | MSK | PT Control |
| GSM525661 | 1.72 | MSK | PT Control |
| GSM525662 | 0.57 | MSK | PT Control |
| GSM525663 | 0.59 | MSK | PT Control |
| GSM525664 | 0.06 | MSK | PT Control |
| GSM525665 | 0.28 | MSK | PT Control |
| GSM525666 | 1.50 | MSK | mPT |
| GSM525667 | 0.46 | MSK | PT Control |
| GSM525668 | 1.38 | MSK | PT Control |
| GSM525669 | 0.81 | MSK | PT Control |
| GSM525670 | 0.55 | MSK | PT Control |
| GSM525671 | 0.57 | MSK | PT Control |
| GSM525672 | 0.77 | MSK | In+ |
| GSM525673 | 1.81 | MSK | PT Control |
| GSM525674 | 0.65 | MSK | PT Control |
| GSM525675 | 1.01 | MSK | PT Control |
| GSM525676 | 0.37 | MSK | PT Control |
| GSM525677 | 0.90 | MSK | PT Control |
| GSM525678 | 1.61 | MSK | PT Control |
| GSM525679 | 0.47 | MSK | PT Control |
| GSM525680 | 0.89 | MSK | PT Control |
| GSM525681 | 0.89 | MSK | PT Control |
| GSM525682 | 0.48 | MSK | PT Control |
| GSM525683 | 0.49 | MSK | PT Control |
| GSM525684 | 0.32 | MSK | PT Control |
| GSM525685 | 0.72 | MSK | PT Control |
| GSM525686 | 1.20 | MSK | PT Control |
| GSM525687 | 0.66 | MSK | PT Control |
| GSM525688 | 1.72 | MSK | PT Control |
| GSM525689 | 0.86 | MSK | PT Control |
| GSM525690 | 1.22 | MSK | PT Control |
| GSM525691 | 1.42 | MSK | PT Control |
| GSM525692 | 0.22 | MSK | PT Control |
| GSM525693 | 1.61 | MSK | PT Control |
| GSM525694 | 0.67 | MSK | PT Control |
| GSM525695 | 0.42 | MSK | PT Control |
| GSM525696 | 0.37 | MSK | PT Control |
| GSM525697 | 0.90 | MSK | PT Control |
| GSM525698 | 0.25 | MSK | PT Control |

TABLE 3-continued

Prostate tumor metastatic potential score

| sampleID | MPS | cohort | subgroup |
|---|---|---|---|
| GSM525699 | 1.20 | MSK | PT Control |
| GSM525700 | 0.57 | MSK | PT Control |
| GSM525701 | 1.43 | MSK | PT Control |
| GSM525702 | 1.16 | MSK | PT Control |
| GSM525703 | 1.20 | MSK | PT Control |
| GSM525704 | 0.94 | MSK | mPT |
| GSM525705 | 1.11 | MSK | PT Control |
| GSM525706 | 0.84 | MSK | PT Control |
| GSM525707 | 1.52 | MSK | PT Control |
| GSM525708 | 0.71 | MSK | PT Control |
| GSM525709 | 1.55 | MSK | PT Control |
| GSM525710 | 1.47 | MSK | PT Control |
| GSM525711 | 1.07 | MSK | PT Control |
| GSM525712 | 1.28 | MSK | PT Control |
| GSM525713 | 0.87 | MSK | In+ |
| GSM525714 | 1.92 | MSK | mPT |
| GSM525715 | 0.45 | MSK | PT Control |
| GSM525716 | 0.32 | MSK | PT Control |
| GSM525717 | 1.11 | MSK | PT Control |
| GSM525718 | 0.70 | MSK | PT Control |
| GSM525719 | 0.66 | MSK | PT Control |
| GSM525720 | 0.70 | MSK | PT Control |
| GSM525721 | 0.59 | MSK | PT Control |
| GSM525722 | 0.84 | MSK | PT Control |
| GSM525723 | 1.66 | MSK | PT Control |
| GSM525724 | 1.46 | MSK | PT Control |
| GSM525725 | 0.91 | MSK | PT Control |
| GSM525726 | 0.59 | MSK | PT Control |
| GSM525727 | 1.03 | MSK | In+ |
| GSM525728 | 1.22 | MSK | PT Control |
| GSM525729 | 1.48 | MSK | PT Control |
| GSM525730 | 1.54 | MSK | PT Control |
| GSM525731 | 1.15 | MSK | PT Control |
| GSM525732 | 1.32 | MSK | PT Control |
| GSM525733 | 0.66 | MSK | mPT |
| GSM525734 | 0.66 | MSK | PT Control |
| GSM525735 | 1.51 | MSK | PT Control |
| GSM525736 | 1.12 | MSK | PT Control |
| GSM525737 | 1.12 | MSK | PT Control |
| GSM525738 | 1.06 | MSK | PT Control |
| GSM525739 | 1.19 | MSK | PT Control |
| GSM525740 | 0.80 | MSK | PT Control |
| GSM525741 | 1.20 | MSK | PT Control |
| GSM525742 | 1.35 | MSK | PT Control |
| GSM525743 | 0.81 | MSK | PT Control |
| GSM525744 | 1.80 | MSK | PT Control |
| GSM525745 | 1.33 | MSK | PT Control |
| GSM525746 | 1.26 | MSK | PT Control |
| GSM525747 | 1.63 | MSK | PT Control |
| GSM525748 | 1.05 | MSK | PT Control |
| GSM525749 | 0.42 | MSK | PT Control |
| GSM525750 | 1.24 | MSK | PT Control |
| GSM525751 | 1.53 | MSK | PT Control |
| GSM525752 | 0.93 | MSK | PT Control |
| GSM525753 | 1.73 | MSK | In+ |
| GSMS25754 | 1.65 | MSK | mPT |
| GSM525755 | 2.06 | MSK | PT Control |
| GSM525756 | 1.77 | MSK | METS |
| GSM525757 | 1.11 | MSK | METS |
| GSM525758 | 1.45 | MSK | METS |
| GSM525759 | 1.56 | MSK | METS |
| GSM525760 | 1.95 | MSK | METS |
| GSM525761 | 1.03 | MSK | METS |
| GSM525762 | 1.61 | MSK | METS |
| GSM525763 | 2.08 | MSK | METS |
| GSM525764 | 2.05 | MSK | METS |
| GSM525765 | 2.00 | MSK | METS |
| GSM525766 | 1.29 | MSK | METS |
| GSM525767 | 2.04 | MSK | METS |
| GSM525768 | 2.01 | MSK | METS |
| GSM525769 | 2.02 | MSK | METS |
| GSM525770 | 1.83 | MSK | METS |
| GSM525771 | 2.15 | MSK | METS |
| GSM525772 | 1.57 | MSK | METS |
| GSM525773 | 1.44 | MSK | METS |
| GSM525774 | 1.63 | MSK | METS |
| GSM525775 | 1.16 | MSK | METS |
| GSM525776 | 1.80 | MSK | METS |
| GSM525777 | 1.22 | MSK | METS |
| GSM525778 | 1.47 | MSK | METS |
| GSM525779 | 1.59 | MSK | METS |
| GSM525780 | 1.64 | MSK | METS |
| GSM525781 | 1.23 | MSK | METS |
| GSM525782 | 1.94 | MSK | METS |
| GSM525783 | 1.80 | MSK | METS |
| GSM525784 | 0.91 | MSK | METS |
| GSM525785 | 1.98 | MSK | METS |
| GSM525786 | 1.84 | MSK | METS |
| GSM525787 | 2.10 | MSK | METS |
| GSM525788 | 1.65 | MSK | METS |
| GSM525789 | 1.05 | MSK | METS |
| GSM525790 | 2.16 | MSK | METS |
| GSM525791 | 1.85 | MSK | METS |
| GSM525792 | 1.12 | MSK | METS |
| PT130 | 1.35 | SU | PT Control |
| PL133 | 0.95 | SU | In+ |
| PT138 | 0.64 | SU | PT Control |
| PT171 | 1.15 | SU | PT Control |
| PT173 | 0.89 | SU | PT Control |
| PT174 | 1.16 | SU | PT Control |
| PT175 | 0.72 | SU | PT Control |
| PT177 | 0.60 | SU | PT Control |
| PT180 | 0.67 | SU | PT Control |
| PT181 | 0.93 | SU | PT Control |
| PT305 | 1.46 | SU | PT Control |
| PT311 | 0.94 | SU | PT Control |
| PT309 | 1.10 | SU | PT Control |
| PT312 | 0.61 | SU | PT Control |
| PT313 | 0.54 | SU | PT Control |
| PT310 | 0.65 | SU | PT Control |
| PT100 | 1.07 | SU | PT Control |
| PT148 | 0.39 | SU | PT Control |
| PT32 | 0.81 | SU | PT Control |
| PT37 | 0.68 | SU | PT Control |
| PT314 | 1.07 | SU | PT Control |
| PT319 | 1.12 | SU | PT Control |
| PT317 | 1.04 | SU | PT Control |
| PT316 | 1.58 | SU | PT Control |
| PT315 | 1.65 | SU | PT Control |
| PT250 | 1.12 | SU | PT Control |
| PT265 | 0.76 | SU | PT Control |
| PT83 | 0.54 | SU | PT Control |
| PT87 | 0.88 | SU | PT Control |
| PT318 | 0.44 | SU | PT Control |
| PT96 | 1.17 | SU | PT Control |
| PT102 | 0.77 | SU | PT Control |
| PL114 | 0.60 | SU | In+ |
| PL115 | 1.11 | SU | In+ |
| PT116 | 1.43 | SU | In+ |
| PT215 | 0.38 | SU | PT Control |
| PT205 | 0.92 | SU | PT Control |
| PT335 | 1.17 | SU | PT Control |
| PT92 | 0.72 | SU | PT Control |
| PT168 | 1.41 | SU | PT Control |
| PT111 | 0.87 | SU | PT Control |
| PT112 | 0.63 | SU | PT Control |
| PT224 | 0.99 | SU | PT Control |
| PT229 | 0.68 | SU | PT Control |
| PT233 | 0.53 | SU | PT Control |
| PT19 | 1.10 | SU | PT Control |
| PT05 | 0.70 | SU | PT Control |
| PT07 | 0.59 | SU | PT Control |
| PT14 | 0.68 | SU | PT Control |
| PT103 | 0.83 | SU | PT Control |
| PT187 | 0.67 | SU | PT Control |
| PT190 | 0.82 | SU | PT Control |
| PT191 | 1.29 | SU | PT Control |
| PT195 | 0.79 | SU | PT Control |
| PT126 | 0.22 | SU | PT Control |
| PT255 | 0.75 | SU | PT Control |
| PT28 | 0.85 | SU | PT Control |
| PT21 | 0.50 | SU | PT Control |

TABLE 3-continued

Prostate tumor metastatic potential score

| sampleID | MPS | cohort | subgroup |
|---|---|---|---|
| PL27 | 1.43 | SU | In+ |
| PL118 | 0.47 | SU | In+ |
| PL122 | 1.59 | SU | In+ |
| PL129 | 1.17 | SU | In+ |
| PL194 | 1.59 | SU | In+ |
| PT41 | 0.98 | SU | PT Control |

TABLE 4

Cell line metastatic potential score

| sampleID | MPS | Cat. No. | Origin |
|---|---|---|---|
| SS493134 | 1.78 | CCL-121 | Lung |
| SS493087 | 1.76 | HTB-22 | Lung |
| SS356931 | 1.69 | CCL-155 | Thyroid gland |
| SS356919 | 1.66 | HTB-131 | Rectum |
| SS364381 | 1.59 | CRL-1420 | Pancreas |
| SS493086 | 1.58 | HTB-77 | Lung |
| SS285144 | 1.58 | CRL-5806 | Lung |
| SS493106 | 1.55 | CRL-2505 | Lung |
| SS493131 | 1.54 | ACC 298 | Lung |
| SS320522 | 1.52 | HTB-76 | Colon |
| SS493080 | 1.52 | CRL-2289 | Lung |
| SS320536 | 1.50 | CCL-225 | Pharynx |
| SS320523 | 1.50 | HTB-64 | Colon |
| SS285160 | 1.49 | CRL-1933 | Lung |
| SS356911 | 1.44 | HTB-79 | Skin |
| SS285181 | 1.43 | CCL-138 | Skin |
| SS285143 | 1.42 | HTB-112 | Lung |
| SS493083 | 1.42 | CRL-8083 | Lung |
| SS320542 | 1.42 | CRL-1718 | Breast |
| SS285215 | 1.40 | CRL-2064 | Breast |
| SS320532 | 1.40 | HTB-32 | Kidney |
| SS364371 | 1.39 | CRL-2270 | Breast |
| SS356924 | 1.38 | CRL-7898 | Thyroid gland |
| SS320538 | 1.37 | HTB-31 | Breast |
| SS285163 | 1.37 | CCL-119 | Prostate |
| SS356942 | 1.37 | CRL-2062 | Breast |
| SS320553 | 1.35 | HB-8064 | Breast |
| SS320530 | 1.35 | TIB-161 | Colon |
| SS285179 | 1.35 | CRL-5868 | Bladder |
| SS493073 | 1.35 | CRL-1619 | Lung |
| SS493091 | 1.34 | CRL-10741 | Lung |
| SS493075 | 1.34 | CRL-9446 | Esophagus |
| SS356925 | 1.33 | CRL-2049 | Hematopoietic and Lymphatic System |
| SS320539 | 1.33 | HB-8065 | Breast |
| SS285138 | 1.31 | HTB-1 | Lung |
| SS285072 | 1.31 | CRL-1976 | Hematopoietic and Lymphatic System |
| SS421708 | 1.30 | CRL-5819 | Hematopoietic and Lymphatic System |
| SS493081 | 1.30 | CRL-1594 | Lung |
| SS285115 | 1.30 | CRL-2273 | Pancreas |
| SS285137 | 1.29 | CRL-7920 | Lung |
| SS364370 | 1.28 | CRL-2105 | Breast |
| SS320541 | 1.27 | HTB-144 | Breast |
| SS285109 | 1.27 | CRL-2274 | Liver |
| SS320537 | 1.26 | HTB-173 | Breast |
| SS285142 | 1.26 | CRL-1595 | Lung |
| SS320524 | 1.26 | CCL-224 | Colon |
| SS285161 | 1.26 | CRL-2258 | Lung |
| SS285098 | 1.25 | HTB-36 | Pharynx |
| SS493097 | 1.25 | CRL-1977 | Lung |
| SS285102 | 1.23 | CRL-1598 | Cervix Uteri |
| SS356922 | 1.23 | CRL-2220 | Pancreas |
| SS285082 | 1.22 | CCL-85 | Kidney |
| SS364375 | 1.22 | CRL-9607 | Hematopoietic and Lymphatic System |
| SS493102 | 1.21 | CRL-10423 | Lung |
| SS364369 | 1.21 | CRL-1427 | Breast |
| SS320544 | 1.21 | CRL-5892 | Breast |
| SS285172 | 1.20 | CRL-2500 | Hematopoietic and Lymphatic System |
| SS285151 | 1.20 | HTB-46 | Lung |
| SS493137 | 1.20 | CCL-220.1 | Lung |
| SS421690 | 1.19 | CRL-1978 | Hematopoietic and Lymphatic System |
| SS285085 | 1.18 | CRL-1543 | Ovary |
| SS285194 | 1.18 | CCL-243 | Liver |
| SS493088 | 1.18 | CRL-5804 | Lung |
| SS285186 | 1.18 | CRL-2230 | Skin |
| SS493112 | 1.17 | HTB-47 | Lung |
| SS285080 | 1.17 | HTB-185 | Cervix Uteri |
| SS285202 | 1.17 | CRL-1440 | Cervix Uteri |
| SS356916 | 1.16 | CRL-2119 | Liver |
| SS493096 | 1.16 | CRL-1545 | Esophagus |
| SS493095 | 1.16 | CRL-8294 | Esophagus |
| SS493143 | 1.14 | CRL-5915 | Colon |
| SS285120 | 1.13 | CRL-2231 | Bladder |
| SS285100 | 1.11 | HTB-55 | Lung |
| SS421716 | 1.11 | HTB-187 | Hematopoietic and Lymphatic System |
| SS493079 | 1.11 | CRL-11351 | Lung |
| SS493089 | 1.11 | CRL-1997 | Lung |
| S5285141 | 1.10 | CRL-1622 | Lung |
| SS285154 | 1.10 | CRL-1582 | Lung |
| SS285192 | 1.10 | CRL-2277 | Liver |
| SS247746 | 1.10 | HTB-75 | Breast |
| SS285092 | 1.10 | CCL-213 | Colon |
| SS320540 | 1.09 | CRL-2324 | Breast |
| SS247731 | 1.09 | CRL-2260 | Breast |
| SS351242 | 1.08 | CRL-5922 | Bladder |
| SS285113 | 1.08 | CRL-5808 | Skin |
| SS356907 | 1.08 | HTB-175 | Bladder |
| SS285209 | 1.07 | HTB-69 | Colon |
| SS285164 | 1.06 | CRL-1647 | Lung |
| SS285170 | 1.06 | CRL-7763 | Ovary |
| SS285214 | 1.06 | HTB-172 | Breast |
| SS351246 | 1.05 | CRL-11609 | Colon |
| SS285118 | 1.05 | CRL-2137 | Cervix Uteri |
| SS356933 | 1.05 | HTB-94 | Bladder |
| SS356928 | 1.04 | TIB-202 | Thyroid gland |
| SS285162 | 1.04 | CRL-5985 | Rectum |
| SS285101 | 1.04 | CRL-11732 | Lung |
| SS285190 | 1.04 | CRL-2149 | Hematopoietic and Lymphatic System |
| SS285087 | 1.03 | CRL-2172 | Pancreas |
| SS493104 | 1.03 | CRL-1803 | Lung |
| SS493099 | 1.03 | CRL-5928 | Lung |
| SS285205 | 1.02 | HTB-182 | Lung |
| SS285090 | 1.01 | HTB-161 | Skin |
| SS285066 | 1.00 | HTB-3 | Kidney |
| SS493136 | 1.00 | CRL-2142 | Lung |
| SS285067 | 1.00 | HTB-91 | Skin |
| SS320511 | 1.00 | TIB-196 | Skin |
| SS493119 | 1.00 | CRL-5929 | Lung |
| SS351247 | 0.99 | CRL-5810 | Central Nervous System |
| SS493092 | 0.99 | HTB-62 | Lung |
| SS421718 | 0.98 | CRL-8033-1 | Hematopoietic and Lymphatic System |
| SS285153 | 0.98 | CRL-10302 | Brain |
| SS493074 | 0.98 | CRL-5931 | Lung |
| SS493072 | 0.98 | CRL-5811 | Lung |
| SS285227 | 0.98 | CRL-7724 | Uterus |
| SS356906 | 0.97 | HTB-114 | Bladder |
| SS285193 | 0.97 | CRL-2169 | Liver |
| SS285158 | 0.97 | CRL-1897 | Lung |
| SS493113 | 0.96 | CRL-5826 | Lung |
| SS364374 | 0.94 | HTB-178 | Breast |
| SS421700 | 0.94 | CCL-86 | Hematopoietic and Lymphatic System |
| SS285216 | 0.94 | CRL-2195 | Bladder |
| SS285079 | 0.93 | CRL-2235 | Cervix Uteri |
| SS493108 | 0.93 | HTB-92 | Lung |
| SS493123 | 0.93 | CRL-1902 | Lung |
| SS285149 | 0.93 | CRL-5800 | Lung |
| SS285212 | 0.92 | CRL-5833 | Thyroid gland |
| SS364367 | 0.92 | CCL-136 | Stomach |
| SS493082 | 0.92 | HTB-35 | Lung |
| SS285145 | 0.91 | CRL-2237 | Lung |
| SS356909 | 0.91 | HTB-59 | Breast |
| SS285204 | 0.91 | CRL-1749 | Connective Tissue |
| SS364377 | 0.91 | CRL-5813 | Hematopoietic and Lymphatic System |
| SS285106 | 0.91 | HTB-166 | Breast |
| SS421720 | 0.90 | CRL-2233 | Hematopoietic and Lymphatic System |
| SS285083 | 0.90 | HTB-117 | Kidney |
| SS421696 | 0.90 | HTB-169 | Hematopoietic and Lymphatic System |

TABLE 4-continued

Cell line metastatic potential score

| sampleID | MPS | Cat. No. | Origin |
|---|---|---|---|
| SS285139 | 0.90 | CRL-2128 | Lung |
| SS285086 | 0.89 | HTB-183 | Ovary |
| SS356927 | 0.89 | HTB-88 | Ovary |
| SS285116 | 0.89 | CRL-2238 | Pancreas |
| SS364365 | 0.88 | HTB-118 | Breast |
| SS285127 | 0.88 | CCL-75 | Skin |
| SS356918 | 0.87 | HTB-119 | Central Nervous System |
| SS285075 | 0.87 | CRL-2261 | Prostate |
| SS493078 | 0.87 | HTB-67 | Lung |
| SS493107 | 0.86 | CRL-2234 | Lung |
| SS285104 | 0.85 | HTB-93 | Ovary |
| SS285200 | 0.85 | CRL-1675 | Pancreas |
| SS285071 | 0.84 | CRL-5807 | Skin |
| SS285207 | 0.84 | CRL-1671 | Vulva |
| SS285129 | 0.84 | CBL-2262 | Central Nervous System |
| SS356917 | 0.84 | CCL-237 | Central Nervous System |
| SS320514 | 0.84 | HTB-18 | Hematopoietic and Lymphatic System |
| SS285173 | 0.83 | CCL-233 | Muscle |
| SS493098 | 0.83 | TIB-153 | Lung |
| SS493109 | 0.83 | CRL-2343 | Lung |
| SS285187 | 0.82 | CRL-1974 | Central Nervous System |
| SS493084 | 0.81 | CRL-2314 | Esophagus |
| SS285111 | 0.81 | CRL-1621 | Hematopoietic and Lymphatic System |
| SS421722 | 0.81 | CCL-230 | Hematopoietic and Lymphatic System |
| SS285169 | 0.81 | CCL-98 | Ovary |
| SS421717 | 0.80 | TIB-223 | Hematopoietic and Lymphatic System |
| SS285195 | 0.79 | CRL-8644 | Liver |
| SS421689 | 0.79 | ACC 3 | Hematopoietic and Lymphatic System |
| SS285213 | 0.79 | HTB-53 | Hematopoietic and Lymphatic System |
| SS421692 | 0.79 | CCL-244 | Hematopoietic and Lymphatic System |
| SS364380 | 0.79 | CCL-238 | Prostate |
| SS493077 | 0.79 | HTB-25 | Lung |
| SS285108 | 0.79 | CCL-231 | Uterus |
| SS285150 | 0.78 | HTB-43 | Lung |
| SS285196 | 0.78 | CCL-218 | Liver |
| SS356915 | 0.78 | CRL-2320 | Pancreas |
| SS285123 | 0.77 | CRL-1611 | Hematopoietic and Lymphatic System |
| SS493085 | 0.77 | HTB-44 | Lung |
| SS247758 | 0.77 | CRL-2321 | Lung |
| SS421711 | 0.77 | CCL-113 | Hematopoietic and Lymphatic System |
| SS285185 | 0.77 | CRL-2331 | Skin |
| SS356910 | 0.76 | CRL-2336 | Pancreas |
| SS493071 | 0.76 | TIB-180 | Lung |
| SS351252 | 0.76 | CRL-1620 | Colon |
| SS356921 | 0.76 | CRL-2338 | Central Nervous System |
| SS351245 | 0.76 | HTB-48 | Colon |
| SS364373 | 0.76 | ACC325 | Bladder |
| SS247736 | 0.76 | CL-188 | Hematopoietic and Lymphatic System |
| SS285197 | 0.76 | TIB-190 | Hematopoietic and Lymphatic System |
| SS421685 | 0.76 | CRL-2061 | Hematopoietic and Lymphatic System |
| SS493125 | 0.75 | CCL-227 | Lung |
| SS285094 | 0.75 | HTB-103 | Central Nervous System |
| SS351239 | 0.75 | CRL-1739 | Stomach |
| SS285133 | 0.75 | HTB-16 | Hematopoietic and Lymphatic System |
| SS351251 | 0.74 | CCL-228 | Brain |
| SS493135 | 0.74 | CRL-5974 | Lung |
| SS493094 | 0.73 | CRL-9591 | Lung |
| SS351250 | 0.73 | HTB-9 | Stomach |
| SS364372 | 0.73 | CCL-251 | Bladder |
| SS285225 | 0.73 | CRL-2158 | Uterus |
| SS285131 | 0.73 | CCL-235 | Bone |
| SS351249 | 0.73 | CCL-252 | Muscle |
| SS351235 | 0.72 | CBL-2020 | Kidney |
| SS285088 | 0.72 | HTB-13 | Central Nervous System |
| SS493093 | 0.71 | ACC 7 | Lung |
| SS285199 | 0.71 | CRL-1473 | Bone |
| SS285226 | 0.71 | HTB-12 | Lung |
| SS356914 | 0.71 | CRL-2315 | Uterus |
| SS285177 | 0.71 | CRL-1472 | Prostate |
| SS364368 | 0.70 | CCL-234 | Hematopoietic and Lymphatic System |
| SS285119 | 0.70 | ACC 448 | Hematopoietic and Lymphatic System |
| SS493103 | 0.70 | CRL-5971 | Lung |
| SS285203 | 0.70 | ACC 29 | Bladder |
| SS421693 | 0.70 | HTB-19 | Hematopoietic and Lymphatic System |
| SS493116 | 0.70 | HTB-148 | Lung |
| SS364379 | 0.70 | ACC 413 | Central Nervous System |
| SS285206 | 0.69 | 93121055 | Vulva |
| SS285176 | 0.69 | HTB-80 | Uterus |
| SS247725 | 0.68 | CRL-2268 | Connective Tissue |
| SS421705 | 0.68 | CRL-1579 | Hematopoietic and Lymphatic System |
| SS285099 | 0.68 | CRL-1441 | Lung |
| SS320512 | 0.67 | HTB-82 | Lung |
| SS351253 | 0.66 | HTB-113 | Hematopoietic and Lymphatic System |
| SS421702 | 0.66 | ACC 279 | Hematopoietic and Lymphatic System |
| SS493070 | 0.66 | ACC 20 | Lung |
| SS285065 | 0.66 | HTB-111 | Prostate |
| SS285068 | 0.66 | ACC 135 | Skin |
| SS320507 | 0.65 | CRL-1682 | Lung |
| SS421699 | 0.65 | ACC 198 | Hematopoietic and Lymphatic System |
| SS285148 | 0.64 | CRL-2236 | Lung |
| SS493100 | 0.64 | ACC 360 | Lung |
| SS351241 | 0.64 | ACC 15 | Stomach |
| SS356926 | 0.63 | ACC 403 | Hematopoietic and Lymphatic System |
| SS285219 | 0.63 | ACC 365 | Skin |
| SS421709 | 0.63 | CRL-2265 | Hematopoietic and Lymphatic System |
| SS285218 | 0.63 | ACC 215 | Lung |
| SS285146 | 0.62 | CRL-5973 | Lung |
| SS285175 | 0.62 | ACC 131 | Hematopoietic and Lymphatic System |
| SS421687 | 0.61 | ACC 87 | Hematopoietic and Lymphatic System |
| SS320509 | 0.61 | ACC 277 | Hematopoietic and Lymphatic System |
| SS356940 | 0.61 | ACC 231 | Hematopoietic and Lymphatic System |
| SS285211 | 0.61 | ACC 143 | Hematopoietic and Lymphatic System |
| SS285217 | 0.61 | ACC 427 | Eye |
| SS356941 | 0.61 | CRL-2340 | Hematopoietic and Lymphatic System |
| SS285208 | 0.60 | ACC 361 | Synovial Membrane |
| SS285159 | 0.60 | ACC 317 | Lung |
| SS421724 | 0.60 | ACC 48 | Colon |
| SS421712 | 0.59 | ACC 414 | Hematopoietic and Lymphatic System |
| SS421719 | 0.59 | ACC 382 | Hematopoietic and Lymphatic System |
| SS356912 | 0.59 | CRL-1552 | Uterus |
| SS356932 | 0.59 | CRL-2625 | Hematopoietic and Lymphatic System |
| SS364376 | 0.58 | ACC 548 | Kidney |
| SS421695 | 0.58 | ACC 128 | Hematopoietic and Lymphatic System |
| SS285105 | 0.57 | ACC 18 | Kidney |
| SS421703 | 0.57 | ACC 47 | Hematopoietic and Lymphatic System |
| SS356929 | 0.56 | ACC 399 | Central Nervous System |
| SS493114 | 0.56 | ACC 378 | Lung |
| SS285174 | 0.55 | ACC 346 | Bone |
| SS421713 | 0.55 | CRL-1484 | Hematopoietic and Lymphatic System |
| SS285155 | 0.54 | CCL-87 | Lung |
| SS364366 | 0.54 | CRL-2392 | Hematopoietic and Lymphatic System |
| SS285183 | 0.54 | CRL-2631 | Cervix Uteri |
| SS320525 | 0.54 | ACC 526 | Colon |
| SS285074 | 0.54 | CCL-248 | Hematopoietic and Lymphatic System |
| SS421691 | 0.54 | CCL-246 | Hematopoietic and Lymphatic System |
| SS285126 | 0.53 | CRL-7779 | Uterus |
| SS421706 | 0.53 | ACC 354 | Hematopoietic and Lymphatic System |
| SS421707 | 0.52 | ACC 572 | Hematopoietic and Lymphatic System |
| SS285130 | 0.51 | ACC 576 | Uterus |
| SS285167 | 0.51 | ACC 546 | Lung |
| SS285112 | 0.51 | HTB-60 | Hematopoietic and Lymphatic System |
| SS351237 | 0.51 | ACC 497 | Hematopoietic and Lymphatic System |
| SS285171 | 0.50 | CRL-2630 | Hematopoietic and Lymphatic System |
| SS285091 | 0.50 | CRL-1432 | Brain |
| SS421694 | 0.49 | CRL-2740 | Hematopoietic and Lymphatic System |
| SS285191 | 0.49 | ACC 197 | Uterus |
| SS285124 | 0.49 | ACC 571 | Hematopoietic and Lymphatic System |
| SS285073 | 0.49 | ACC 577 | Hematopoietic and Lymphatic System |
| SS493090 | 0.48 | HTB-61 | Lung |
| SS421704 | 0.47 | ACC 139 | Hematopoietic and Lymphatic System |
| SS493121 | 0.46 | CRL-8119 | Lung |
| SS285089 | 0.45 | CRL-2632 | Hematopoietic and Lymphatic System |
| SS285198 | 0.45 | CRL-2021 | Hematopoietic and Lymphatic System |
| SS421710 | 0.44 | CRL-1648 | Hematopoietic and Lymphatic System |
| SS285070 | 0.44 | CRL-8119 | Muscle |
| SS285077 | 0.44 | CRL-1649 | Cervix Uteri |
| SS285189 | 0.44 | ACC 584 | Central Nervous System |
| SS285103 | 0.43 | CCL-214 | Hematopoietic and Lymphatic System |
| SS320508 | 0.43 | CRL-5818 | Kidney |
| SS493139 | 0.43 | CRL-5920 | Bone |
| SS364378 | 0.43 | HTB-58 | Hematopoietic and Lymphatic System |
| SS285165 | 0.43 | CRL-5906 | Lung |

TABLE 4-continued

Cell line metastatic potential score

| sampleID | MPS | Cat. No. | Origin |
|---|---|---|---|
| SS356908 | 0.42 | 92031919 | Stomach |
| SS351238 | 0.42 | CRL-5883 | Colon |
| SS285093 | 0.42 | 96071721 | Colon |
| SS285097 | 0.42 | CRL-5896 | Hematopoietic and Lymphatic System |
| SS421714 | 0.42 | CRL-5983 | Hematopoietic and Lymphatic System |
| SS285210 | 0.42 | CRL-5881 | Connective and Soft Tissue |
| SS356934 | 0.42 | CRL-2578 | Brain |
| SS320548 | 0.41 | HTB-56 | Hematopoietic and Lymphatic System |
| SS320520 | 0.40 | 96070808 | Hematopoietic and Lymphatic System |
| SS421715 | 0.40 | ACC 351 | Hematopoietic and Lymphatic System |
| SS285132 | 0.40 | CRL-5879 | Hematopoietic and Lymphatic System |
| SS285114 | 0.40 | CCL-256 | Sarcoma |
| SS421701 | 0.40 | CRL-5889 | Hematopoietic and Lymphatic System |
| SS285095 | 0.40 | CRL-5899 | Brain |
| SS285184 | 0.40 | CRL-5893 | Vulva |
| SS285117 | 0.38 | CRL-5841 | Hematopoietic and Lymphatic System |
| SS351244 | 0.38 | HTB-171 | Colon |
| SS285147 | 0.37 | CRL-5942 | Lung |
| SS285096 | 0.36 | CRL-5844 | Hematopoietic and Lymphatic System |
| SS247756 | 0.36 | CRL-5855 | Ovary |
| SS320533 | 0.36 | CRL-5885 | Placenta |
| SS285122 | 0.36 | 96062201 | Placenta |
| SS421697 | 0.35 | HTB-174 | Hematopoietic and Lymphatic System |
| SS320531 | 0.35 | CRL-5835 | Brain |
| SS285220 | 0.34 | CRL-5888 | Eye |
| SS421686 | 0.33 | CRL-5831 | Hematopoietic and Lymphatic System |
| SS421723 | 0.33 | CRL-5878 | Hematopoietic and Lymphatic System |
| SS356935 | 0.32 | CRL-5877 | Muscle |
| SS320545 | 0.31 | 95062830 | Hematopoietic and Lymphatic System |
| SS285084 | 0.31 | CRL-5816 | Lung |
| SS320513 | 0.31 | CRL-5853 | Colon |
| SS285078 | 0.31 | CRL-2170 | Liver |
| SS493110 | 0.31 | 96020324 | Lung |
| SS421688 | 0.30 | CRL-5914 | Hematopoietic and Lymphatic System |
| SS356923 | 0.30 | 92031917 | Kidney |
| SS421721 | 0.30 | CRL-5865 | Hematopoietic and Lymphatic System |
| SS285188 | 0.29 | CRL-5895 | Brain |
| SS285182 | 0.27 | CRL-5909 | Lung |
| SS285107 | 0.26 | HTB-54 | Colon |
| SS285121 | 0.25 | CRL-5908 | Placenta |
| SS351243 | 0.24 | CRL-2066 | Colon |
| SS320550 | 0.23 | CRL-5838 | Hematopoietic and Lymphatic System |
| SS351236 | 0.20 | CRL-2098 | Colon |
| SS247755 | 0.19 | CRL-5884 | Pancreas |
| SS285081 | 0.17 | CRL-5872 | Prostate |
| SS285128 | 0.17 | CRL-5871 | Hematopoietic and Lymphatic System |
| SS285125 | 0.12 | 92031918 | Sarcoma |
| SS285201 | 0.08 | CRL-5911 | Connective Tissue |
| SS285110 | 0.00 | CRL-5935 | Liver |

TABLE 5

Model predictions achieved with a range of genes.

| Genes | r2 | auc |
|---|---|---|
| top12 | 0.69 | 0.77 |
| top20 | 0.78 | 0.81 |
| top40 | 0.89 | 0.85 |
| top80 | 0.94 | 0.82 |
| top100 | 0.94 | 0.82 |

| Final-RANK | gene | index | NYU-Z | NYU-dir | NYU-count | MSKs1-Z | MSKs1-dir | MSKs1-count | MSKs2-Z | MSKs2-dir | MSKs2-count | logrank-n52random | logrank-n271random | logrank-composite | gene-Chr | gene-Cytoband |
|---|---|---|---|---|---|---|---|---|---|---|---|---|---|---|---|---|
| 1 | PPP3CC | 129 | 3.1 | −1 | 958 | 2.6 | −1 | 965 | NA | NA | NA | 48 | 41 | 45 | 8 | p21.3 |
| 2 | SLCO5A1 | 167 | 4.9 | 1 | 1000 | 4.2 | 1 | 982 | NA | NA | NA | 31 | 13 | 19 | 8 | q13.3 |
| 3 | SLC7A5 | 312 | 1.7 | −1 | 508 | 3 | −1 | 980 | NA | NA | NA | 43 | 37 | 40 | 16 | q24.2 |
| 4 | SLC7A2 | 110 | 4.1 | −1 | 1000 | NA | NA | NA | NA | NA | NA | 44 | 43 | 44 | 8 | p22 |
| 5 | CRISPLD2 | 299 | 2.5 | −1 | 735 | 2.9 | −1 | 939 | NA | NA | NA | 54 | 67 | 61 | 16 | q24.1 |
| 6 | CDH13 | 288 | 8 | 1 | 984 | 2.9 | −1 | 767 | NA | NA | NA | 46 | 86 | 63 | 16 | q23.3 |
| 7 | CDH8 | 265 | NA | NA | NA | NA | NA | NA | 3.7344 | −1 | 989 | 15 | 10 | 11 | 16 | q21 |
| 8 | CDH2 | 349 | 7.1 | −1 | 1000 | NA | NA | NA | 3.4466 | −1 | 987 | 16 | 15 | 17 | 18 | q12.1 |
| 9 | ASAH1 | 114 | 6.8 | 1 | 1000 | NA | NA | NA | NA | NA | NA | 105 | 64 | 80 | 8 | p22 |
| 10 | KCNB2 | 175 | NA | NA | NA | NA | NA | NA | 3.7501 | 1 | 983 | 59 | 74 | 66 | 8 | q13.3 |
| 11 | KCNH4 | 343 | NA | NA | NA | NA | NA | NA | 2.8192 | −1 | 921 | 1 | 1 | 1 | 17 | q21.2 |
| 12 | KCTD8 | 21 | NA | NA | NA | NA | NA | NA | NA | NA | NA | 30 | 24 | 29 | 4 | p13 |
| 13 | JPH1 | 179 | 6 | 1 | 1000 | NA | NA | NA | 3.2232 | −1 | 940 | 29 | 35 | 31 | 8 | q21.11 |
| 14 | MEST | 88 | NA | NA | NA | NA | NA | NA | NA | NA | NA | 32 | 32 | 32 | 7 | q32.2 |
| 15 | NCALD | 207 | 5.5 | 1 | 1000 | 2.9 | 1 | 953 | 3.4333 | −1 | 936 | 13 | 12 | 13 | 8 | q22.3 |
| 16 | COL19A1 | 39 | NA | NA | NA | NA | NA | NA | 3.1873 | −1 | 929 | 27 | 20 | 21.5 | 6 | q13 |
| 17 | MAP3K7 | 43 | NA | NA | NA | NA | NA | NA | 2.7386 | −1 | 951 | 47 | 54 | 49 | 6 | q15 |
| 18 | YWHAG | 67 | NA | NA | NA | NA | NA | NA | 3.9113 | 1 | 993 | 40 | 62 | 47 | 7 | q11.23 |
| 19 | NOL4 | 350 | NA | NA | NA | NA | NA | NA | 5.6235 | 1 | 1000 | 4 | 2 | 2 | 18 | q12.1 |
| 20 | ENOX1 | 247 | NA | NA | NA | NA | NA | NA | 4.6280 | 1 | 971 | 2 | 8 | 4 | 13 | q14.11 |
| 21 | CSMD1 | 94 | NA | NA | NA | NA | NA | NA | 3.5107 | −1 | 861 | 7 | 6 | 6 | 8 | p23.2 |
| 22 | SGCZ | 107 | 4.7 | −1 | 926 | NA | NA | NA | 4.6945 | −1 | 999 | 9 | 5 | 7 | 8 | p22 |
| 23 | PDE10A | 54 | NA | NA | NA | NA | NA | NA | 4.5416 | 1 | 962 | 8 | 7 | 8 | 6 | q27 |
| 24 | HTR2A | 252 | NA | NA | NA | NA | NA | NA | 3.2974 | −1 | 966 | 5 | 19 | 9 | 13 | q21.32 |
| 25 | HIP1 | 250 | NA | NA | NA | NA | NA | NA | 4.4416 | −1 | 1000 | 10 | 11 | 10 | 13 | q14.2 |
| 26 | DCC | 63 | NA | NA | NA | NA | NA | NA | 3.3032 | 1 | 1000 | 11 | 14 | 12 | 7 | q11.23 |
| 27 | CC2D1A | 354 | NA | NA | NA | NA | NA | NA | 6.6211 | 1 | 1000 | 18 | 9 | 14 | 18 | q22.2 |
| 28 | PTK2B | 352 | NA | NA | NA | NA | NA | NA | 3.9705 | 1 | 996 | 12 | 17 | 15 | 18 | q21.2 |
| 29 | BCMO1 | 357 | 7 | −1 | 1000 | NA | NA | NA | NA | NA | NA | 17 | 18 | 18 | 19 | p13.12 |
| 30 | GRID2 | 152 | 2.9 | −1 | 284 | 3.6 | −1 | 957 | NA | NA | NA | 20 | 27 | 21.5 | 8 | p21.2 |
| 31 | DIAPH3 | 238 | NA | NA | NA | 1.9 | 1 | 533 | 2.8909 | 1 | 973 | 26 | 21 | 23 | 16 | q23.2 |
| 32 | MACROD1 | 24 | NA | NA | NA | NA | NA | NA | 5.1103 | 1 | 983 | 25 | 22 | 24 | 11 | q13.1 |
| 33 | PILRB | 251 | NA | NA | NA | NA | NA | NA | 3.2653 | 1 | 982 | 22 | 26 | 25 | 4 | q22.1 |
| 34 | MEIS2 | 69 | NA | NA | NA | NA | NA | NA | 2.9352 | 1 | 996 | 24 | 29 | 27 | 13 | q21.2 |
| 35 | MSRA | 259 | NA | NA | NA | NA | NA | NA | 3.9428 | −1 | 999 | 28 | 25 | 28 | 7 | q22.1 |
| 36 | DPYD | 98 | 5.1 | −1 | 999 | NA | NA | NA | NA | NA | NA | 19 | 39 | 30 | 15 | q14 |
| 37 | ANKRD11 | 4 | NA | NA | NA | NA | NA | NA | 2.8861 | −1 | 847 | 34 | 31 | 33 | 8 | p23.1 |
| 38 | NRXN1 | 329 | 3 | −1 | 948 | 3.7 | −1 | 988 | NA | NA | NA | 33 | 34 | 34 | 1 | p21.3 |
| 39 | ADCY8 | 6 | NA | NA | NA | NA | NA | NA | 3.2327 | −1 | 840 | 37 | 33 | 35 | 16 | q24.3 |
| 40 | TRDN | 225 | 3.1 | 1 | 980 | 5.4 | 1 | 1000 | NA | NA | NA | 39 | 38 | 38 | 2 | p16.3 |
| 41 | STAU2 | 49 | NA | NA | NA | NA | NA | NA | 3.0342 | −1 | 898 | 52 | 30 | 39 | 8 | q22.31 |
| 42 | SF1 | 177 | 4.6 | −1 | 1000 | NA | NA | NA | NA | NA | NA | 38 | 44 | 41 | 6 | q22.11 |
| 43 | CLIP2 | 240 | NA | NA | NA | NA | NA | NA | 2.4710 | 1 | 886 | 45 | 42 | 43 | 8 | q21.11 |
| 44 | CLDN3 | 62 | NA | NA | NA | NA | NA | NA | 3.0945 | 1 | 998 | 55 | 46 | 48 | 11 | q13.1 |
| 45 | ZSWIM4 | 58 | NA | NA | NA | NA | NA | NA | 2.6179 | 1 | 984 | 57 | 47 | 50 | 7 | q11.23 |
| 46 | GLRB | 355 | NA | NA | NA | NA | NA | NA | 2.8120 | 1 | 975 | 51 | 53 | 51 | 7 | q11.23 |
| 47 | DCHS2 | 26 | NA | NA | NA | NA | NA | NA | 2.6600 | 1 | 963 | 60 | 51 | 57 | 19 | p13.13 |
| 48 | | 25 | NA | NA | NA | NA | NA | NA | 2.7883 | −1 | 954 | 64 | 48 | 58 | 4 | q32.1 |
| 49 | | | | | | | | | | | | 68 | 60 | 64 | 4 | q32.1 |

| | | | | | | | | | | | | | |
|---|---|---|---|---|---|---|---|---|---|---|---|---|---|
| 50 | TRPS1 | 217 | 2.9 | 1 | 814 | 2.7 | 1 | 751 | NA | 1 | NA | 63 | 65 | 65 | 8 | q23.3 |
| 51 | MDGA2 | 258 | NA | NA | NA | NA | NA | NA | 2.8345 | -1 | 823 | 69 | 66 | 68 | 14 | q21.3 |
| 52 | CNBD1 | 193 | 3.8 | 1 | 999 | 3.8 | 1 | 940 | NA | 1 | NA | 67 | 70 | 69 | 8 | q21.3 |
| 53 | STAG3 | 68 | NA | NA | NA | NA | NA | NA | 2.4187 | 1 | 967 | 78 | 68 | 71 | 7 | q22.1 |
| 54 | GATA4 | 102 | 3.2 | -1 | 979 | 2.6 | -1 | NA | NA | NA | NA | 72 | 77 | 72 | 8 | p23.1 |
| 55 | VPS13B | 202 | 3.9 | 1 | 999 | NA | NA | NA | NA | NA | NA | 85 | 69 | 74 | 8 | q22.2 |
| 56 | DOCK5 | 144 | 5.4 | -1 | 1000 | NA | NA | NA | NA | NA | NA | 82 | 78 | 76 | 8 | p21.2 |
| 57 | ZHX2 | 218 | NA | NA | NA | 2.6 | 1 | 771 | 2.7472 | 1 | 760 | 66 | 80 | 78 | 8 | q24.13 |
| 58 | ARHGEF5 | 90 | 3.4 | 1 | 991 | NA | NA | NA | NA | NA | NA | 75 | 102 | 81 | 7 | q35 |
| 59 | SDC2 | 198 | NA | NA | NA | 2.8 | 1 | 842 | NA | NA | NA | 93 | 90 | 82 | 8 | q22.1 |
| 60 | MYLK | 10 | NA | NA | NA | NA | NA | NA | 2.4806 | -1 | 794 | 80 | 75 | 83 | 3 | q21.1 |
| 61 | LPHN3 | 23 | NA | NA | NA | NA | NA | NA | 2.3144 | 1 | 904 | 99 | 92 | 85 | 4 | q13.1 |
| 62 | MOSPD3 | 78 | NA | NA | NA | 2.9 | -1 | NA | 2.7616 | 1 | 884 | 90 | 82 | 86 | 7 | q22.1 |
| 63 | GYS2 | 244 | NA | NA | NA | NA | NA | NA | NA | NA | NA | 99 | 83 | 92 | 12 | p12.1 |
| 64 | GAS8 | 336 | NA | NA | NA | 3.7 | -1 | 999 | NA | NA | NA | 84 | 103 | 95 | 16 | q24.3 |
| 65 | RAB9A | 362 | NA | NA | NA | 2.7 | -1 | 870 | 2.4806 | -1 | NA | 98 | 97 | 97 | 23 | p22.2 |
| 66 | POLR3D | 127 | NA | NA | NA | NA | NA | 955 | NA | NA | NA | 91 | 109 | 98 | 8 | p21.3 |
| 67 | PSD3 | 116 | 7.3 | -1 | 1000 | 6.3 | 1 | 996 | NA | NA | NA | 97 | 104 | 100 | 8 | p22 |
| 68 | ZFPM2 | 213 | 4.2 | 1 | 991 | 2.4 | 1 | 858 | 2.2584 | -1 | 839 | 149 | 71 | 101 | 8 | q23.1 |
| 69 | ATP6V1C1 | 209 | NA | NA | NA | NA | NA | NA | NA | NA | NA | 114 | 93 | 102 | 8 | q22.3 |
| 70 | MEF2C | 36 | NA | NA | NA | NA | NA | NA | NA | NA | NA | 109 | 98 | 103 | 5 | q14.3 |
| 71 | PKIA | 185 | 3.3 | 1 | 999 | NA | NA | NA | 2.3049 | 1 | 863 | 115 | 99 | 104 | 8 | q21.12 |
| 72 | ADAMTS18 | 276 | 3.5 | -1 | 902 | NA | NA | NA | 2.3972 | 1 | 920 | 100 | 114 | 105 | 16 | q23.1 |
| 73 | STYXL1 | 65 | NA | NA | NA | NA | NA | NA | NA | NA | NA | 104 | 110 | 106 | 7 | q11.23 |
| 74 | EPM2A | 51 | NA | NA | NA | 2.6 | 1 | 755 | NA | NA | NA | 113 | 105 | 108 | 6 | q24.3 |
| 75 | LEPREL1 | 19 | NA | NA | NA | NA | NA | NA | 2.2755 | 1 | 876 | 106 | 119 | 110 | 3 | q28 |
| 76 | GABRA2 | 22 | NA | NA | NA | 2.4 | 1 | 824 | 1.7131 | 1 | 514 | 119 | 107 | 111 | 4 | p12 |
| 77 | RCOR2 | 237 | NA | NA | NA | 2.2 | -1 | 733 | NA | NA | NA | 108 | 120 | 114 | 11 | q13.1 |
| 78 | MFHAS1 | 95 | 3.3 | -1 | 956 | NA | NA | NA | NA | NA | NA | 121 | 108 | 115 | 8 | p23.1 |
| 79 | SCARA5 | 156 | 3.3 | -1 | 925 | 2.3 | -1 | 856 | NA | NA | NA | 130 | 101 | 116 | 8 | p21.1 |
| 80 | CCDC25 | 155 | 4.4 | -1 | 995 | NA | NA | NA | NA | NA | NA | 132 | 100 | 117 | 8 | p21.1 |
| 81 | FAM38A | 323 | NA | NA | NA | 2.7 | -1 | 885 | 2.2407 | -1 | 641 | 110 | 130 | 119 | 16 | q24.3 |
| 82 | CTSB | 104 | 2.8 | -1 | 941 | 2.3 | 1 | 654 | 2.1943 | -1 | 833 | 111 | 136 | 122 | 8 | p23.1 |
| 83 | PTK2 | 235 | NA | NA | NA | 1.7 | -1 | 508 | NA | NA | NA | 107 | 144 | 123 | 8 | q24.3 |
| 84 | SPIRE2 | 331 | NA | NA | NA | NA | NA | NA | 2.2139 | 1 | 748 | 124 | 128 | 124 | 16 | q24.3 |
| 85 | C13orf23 | 246 | NA | NA | NA | NA | NA | NA | 2.3508 | 1 | 884 | 141 | 113 | 125 | 13 | q13.3 |
| 86 | BOD1L | 20 | NA | NA | NA | 1.8 | -1 | 567 | NA | NA | NA | 129 | 127 | 126 | 4 | p15.33 |
| 87 | FAM160B2 | 120 | 2.5 | -1 | 899 | NA | NA | NA | NA | NA | NA | 127 | 133 | 129 | 8 | p21.3 |
| 88 | NUS1 | 48 | NA | NA | NA | NA | NA | NA | 2.2269 | 1 | 859 | 123 | 139 | 130 | 6 | q22.2 |
| 89 | MTHFSD | 309 | NA | NA | NA | 2.4 | -1 | 824 | NA | NA | NA | 112 | 153 | 131 | 16 | q24.1 |
| 90 | UBR5 | 208 | NA | NA | NA | 2.2 | 1 | 733 | NA | NA | NA | 122 | 155 | 135.5 | 8 | q22.3 |
| 91 | GALNS | 325 | NA | NA | NA | 2.3 | -1 | 856 | NA | NA | NA | 131 | 147 | 137 | 16 | q24.3 |
| 92 | FSTL5 | 28 | NA | NA | NA | NA | NA | NA | 2.2407 | -1 | NA | 138 | 143 | 140 | 4 | q32.2 |
| 93 | SIM1 | 46 | NA | NA | NA | NA | NA | NA | 2.1943 | 1 | 833 | 120 | 165 | 141 | 6 | q16.3 |
| 94 | TG | 231 | 3.8 | 1 | 997 | 2.4 | 1 | 678 | NA | NA | NA | 136 | 149 | 144 | 8 | q24.22 |
| 95 | BFSP2 | 12 | NA | NA | NA | 3.5 | -1 | 931 | NA | NA | NA | 139 | 154 | 148 | 3 | q22.1 |
| 96 | MMP16 | 194 | NA | NA | NA | 4 | -1 | 939 | NA | NA | NA | 158 | 138 | 149 | 8 | q21.3 |
| 97 | RIMS2 | 210 | 2 | 1 | 692 | NA | NA | NA | NA | NA | NA | 161 | 141 | 150 | 8 | q22.3 |
| 98 | PDS5B | 245 | NA | NA | NA | 2.2 | -1 | 988 | 2.0408 | 1 | 661 | 145 | 159 | 151 | 13 | q13.2 |
| 99 | CDK7 | 31 | NA | NA | NA | 2.7 | 1 | NA | NA | NA | NA | 156 | 148 | 153 | 5 | q13.2 |
| 100 | CNTNAP4 | 275 | 3.2 | -1 | 825 | NA | NA | NA | NA | NA | NA | 196 | 126 | 156 | 16 | q23.1 |
| 101 | CFDP1 | 274 | 3 | -1 | 925 | NA | NA | NA | 1.7473 | -1 | 537 | 137 | 187 | 157 | 16 | q23.1 |
| 102 | FBXL4 | 45 | NA | NA | NA | NA | NA | NA | NA | NA | NA | 154 | 167 | 158 | 6 | q16.2 |

-continued

| | | | | | | | | | | | | | |
|---|---|---|---|---|---|---|---|---|---|---|---|---|---|
| 103 | RFX1 | 358 | NA | NA | NA | NA | NA | NA | 134 | 201 | 163 | 19 | p13.12 |
| 104 | NALCN | 256 | NA | NA | NA | NA | NA | NA | 182 | 152 | 165 | 13 | q33.1 |
| 105 | STX1A | 57 | NA | NA | NA | NA | NA | NA | 177 | 161 | 167 | 7 | q11.23 |
| 106 | CYP7B1 | 162 | NA | NA | NA | 2.1724 | 1 | 861 | 147 | 204 | 168 | 8 | q12.3 |
| 107 | ARHGEF10 | 92 | 2.7 | −1 | 875 | 2.1846 | −1 | 731 | 215 | 145 | 171 | 8 | p23.3 |
| 108 | ENTPD4 | 141 | NA | NA | NA | 2.1787 | −1 | 835 | 230 | 137 | 173 | 8 | p21.3 |
| 109 | ZNF704 | 188 | 2.5 | −1 | 937 | NA | NA | NA | 211 | 151 | 174 | 8 | q21.13 |
| 110 | C8orf79 | 105 | 2.9 | −1 | NA | NA | NA | NA | 163 | 197 | 176 | 8 | q21.13 |
| 111 | SLC9A9 | 13 | NA | NA | NA | NA | NA | NA | 170 | 189 | 177 | 3 | p22 |
| 112 | CHMP7 | 139 | 2.7 | 1 | 746 | NA | NA | NA | 185 | 176 | 178 | 8 | p21.3 |
| 113 | GPC5 | 255 | 2.4 | 1 | 925 | NA | NA | NA | 171 | 193 | 180 | 13 | q31.3 |
| 114 | MYC | 222 | 4.2 | 1 | 972 | 2.1374 | 1 | 610 | 218 | 157 | 184 | 8 | q24 |
| 115 | STIP1 | 239 | NA | NA | NA | 1.7766 | NA | NA | 164 | 209 | 185 | 11 | q24.21 |
| 116 | ZBTB20 | 9 | 1.8 | 1 | NA | NA | NA | 613 | 187 | 184 | 186 | 3 | q13.31 |
| 117 | MEN1 | 241 | NA | NA | NA | 2.0513 | 1 | NA | 176 | 203 | 188 | 11 | q13.1 |
| 118 | SLC26A7 | 195 | 2.2 | 1 | NA | NA | NA | 737 | 213 | 168 | 189 | 8 | q13.1 |
| 119 | ALCAM | 8 | NA | NA | NA | 2.4602 | NA | 586 | 194 | 186 | 191 | 3 | q13.11 |
| 120 | KIF13B | 160 | 2.7 | −1 | 854 | NA | NA | NA | 188 | 194 | 192 | 8 | p21.1 |
| 121 | MBTPS1 | 291 | 2.7 | 1 | 906 | 1.8055 | 1 | 580 | 193 | 192 | 193 | 16 | q24.1 |
| 122 | PPP2R5B | 243 | NA | NA | NA | 1.7860 | −1 | 550 | 189 | 202 | 196 | 11 | q13.1 |
| 123 | VPS13C | 260 | NA | NA | NA | 1.7635 | 1 | 549 | 201 | 190 | 197 | 15 | q22.2 |
| 124 | ASPSCR1 | 346 | NA | NA | NA | 1.9843 | 1 | 735 | 219 | 178 | 198 | 17 | q25.3 |
| 125 | EPO | 82 | NA | NA | NA | NA | NA | NA | 169 | 235 | 201 | 7 | q22.1 |
| 126 | HEY1 | 187 | 3 | 1 | 988 | NA | NA | NA | 206 | 195 | 203 | 8 | q21.13 |
| 127 | KALRN | 11 | NA | NA | NA | NA | NA | 674 | 197 | 205 | 204 | 3 | q21.1 |
| 128 | RGS22 | 203 | 2.7 | 1 | 956 | NA | NA | NA | 191 | 215 | 205 | 8 | q22.2 |
| 129 | WDR7 | 353 | NA | NA | NA | 1.9953 | −1 | NA | 200 | 217 | 210 | 18 | q21.31 |
| 130 | COL11A1 | 5 | NA | NA | NA | 1.8924 | 1 | 653 | 233 | 206 | 213 | 1 | p21.1 |
| 131 | GHDC | 344 | 3.6 | −1 | 943 | 1.7523 | −1 | 591 | 221 | 218 | 215 | 17 | q21.2 |
| 132 | ATP2C2 | 295 | 2.8 | 1 | 976 | NA | NA | 523 | 216 | 226 | 216 | 16 | q24.1 |
| 133 | CDH17 | 196 | NA | NA | NA | NA | NA | NA | 227 | 216 | 217 | 8 | q22.1 |
| 134 | DGKG | 17 | NA | NA | NA | 1.8988 | −1 | 568 | 192 | 258 | 219 | 3 | q27.3 |
| 135 | GRK5 | 236 | 2.4 | 1 | NA | NA | NA | 831 | 210 | 237 | 220 | 10 | q26.11 |
| 136 | GRM1 | 52 | NA | NA | NA | NA | NA | NA | 179 | 283 | 223 | 6 | q24.3 |
| 137 | IMPA1 | 190 | 1.9 | NA | 813 | NA | NA | 647 | 243 | 210 | 224 | 8 | q21.13 |
| 138 | RPL7 | 176 | 2.3 | 1 | NA | 1.8391 | −1 | NA | 261 | 211 | 229 | 8 | q21.11 |
| 139 | COL21A1 | 38 | NA | NA | NA | 1.8241 | −1 | 596 | 235 | 246 | 232 | 6 | p12.1 |
| 140 | COL12A1 | 40 | NA | NA | NA | NA | NA | 597 | 241 | 240 | 233 | 6 | q14.1 |
| 141 | MLYCD | 289 | 2.4 | −1 | 819 | NA | NA | NA | 234 | 221 | 234 | 16 | q23.3 |
| 142 | AR | 366 | 2.3 | −1 | 690 | 1.9352 | −1 | 806 | 266 | 248 | 235 | 23 | q12 |
| 143 | PLCB1 | 359 | NA | NA | NA | NA | NA | NA | 181 | 330 | 240 | 20 | p12.3 |
| 144 | ACTL8 | 3 | NA | NA | NA | NA | NA | 582 | 264 | 229 | 242 | 1 | p36.13 |
| 145 | TFDP1 | 257 | NA | NA | NA | 1.8487 | −1 | 729 | 205 | 304 | 248 | 13 | q34 |
| 146 | IQCE | 55 | NA | NA | NA | NA | NA | NA | 250 | 260 | 255 | 7 | p22.2 |
| 147 | SMARCB1 | 360 | 1.8 | −1 | 523 | NA | NA | 580 | 239 | 276 | 256 | 22 | q11.23 |
| 148 | MTDH | 199 | 1.9 | NA | 584 | NA | NA | NA | 225 | 301 | 259 | 8 | q22.1 |
| 149 | NECAB2 | 290 | 2 | NA | 688 | NA | NA | NA | 255 | 271 | 262 | 16 | q23.3 |
| 150 | DEF8 | 334 | 2.3 | −1 | 678 | 2.0578 | −1 | 774 | 214 | 335 | 266 | 16 | q24.3 |
| 151 | RNF40 | 262 | NA | NA | NA | 1.8257 | 1 | 589 | 320 | 227 | 270 | 16 | p11.2 |
| 152 | TICAM2 | 37 | NA | NA | NA | NA | NA | NA | 303 | 241 | 271 | 5 | q22.3 |
| 153 | GLG1 | 271 | 2.1 | −1 | 647 | NA | NA | 587 | 327 | 225 | 273 | 16 | q22.3 |
| 154 | MECOM | 16 | NA | NA | NA | NA | NA | NA | 279 | 268 | 277 | 3 | q26.2 |
| 155 | TCEB1 | 178 | 1.8 | 1 | 590 | NA | NA | NA | 275 | 277 | 279 | 8 | q21.11 |

| | | | | | | | | | | | | | | |
|---|---|---|---|---|---|---|---|---|---|---|---|---|---|---|
| 156 | CTNNA2 | 7 | NA | NA | NA | NA | NA | NA | NA | 538 | 331 | 231 | 280 | 2 | p12 |
| 157 | NIPAL2 | 200 | 1.9 | 1 | 654 | NA | NA | NA | NA | NA | 289 | 265 | 282 | 8 | q22.2 |
| 158 | CDCA2 | 146 | 2 | −1 | 686 | NA | NA | NA | NA | NA | 301 | 255 | 283 | 8 | p21.2 |
| 159 | WWP2 | 267 | 1.8 | −1 | 527 | NA | NA | NA | NA | NA | 251 | 315 | 284 | 16 | q22.1 |
| 160 | DDX19A | 268 | 2.3 | −1 | 756 | NA | NA | NA | NA | NA | 220 | 363 | 285 | 16 | q22.2 |
| 161 | STK3 | 201 | 1.8 | −1 | 614 | NA | NA | NA | NA | NA | 265 | 309 | 287 | 8 | q22.2 |
| 162 | DNAH2 | 337 | 2.3 | −1 | 541 | NA | NA | NA | NA | NA | 247 | 332 | 288 | 17 | p13.1 |
| 163 | NFAT5 | 266 | 1.8 | −1 | 760 | NA | NA | NA | NA | NA | 326 | 254 | 291 | 16 | q22.1 |
| 164 | CNGB1 | 263 | 1.8 | −1 | 524 | NA | NA | NA | NA | NA | 297 | 280 | 292 | 16 | q13 |
| 165 | UBE2CBP | 41 | 2.8 | −1 | 891 | NA | NA | NA | NA | NA | 256 | 326 | 293 | 6 | q14.1 |
| 166 | C8orf16 | 99 | 2.2 | −1 | 725 | NA | NA | NA | NA | NA | 285 | 293 | 294 | 8 | p23.1 |
| 167 | KIAA0196 | 220 | 2.6 | 1 | 819 | NA | NA | NA | NA | NA | 253 | 334 | 296 | 8 | q24.13 |
| 168 | CLCNKB | 1 | NA | NA | NA | NA | NA | 2.0014 | NA | 746 | 276 | 307 | 297 | 1 | p36.13 |
| 169 | C16orf80 | 264 | 2.2 | −1 | 677 | NA | NA | NA | NA | NA | 281 | 302 | 298 | 16 | q21 |
| 170 | ZFHX3 | 270 | 2.2 | −1 | 656 | NA | NA | NA | NA | NA | 313 | 273 | 299 | 16 | q22.3 |
| 171 | PPM1L | 15 | NA | NA | NA | 2 | 1 | NA | 628 | NA | 270 | 329 | 303 | 3 | q26.1 |
| 172 | NKIRAS2 | 338 | 1.8 | 1 | 550 | NA | NA | 1.9634 | NA | 679 | 298 | 299 | 304 | 17 | q21.2 |
| 173 | RSPO2 | 215 | 2.3 | −1 | 735 | NA | NA | NA | NA | NA | 306 | 292 | 305 | 8 | q23.1 |
| 174 | XPO7 | 119 | 2.5 | −1 | 728 | NA | NA | NA | NA | NA | 329 | 272 | 306 | 8 | p21.3 |
| 175 | ME1 | 42 | NA | NA | NA | NA | NA | NA | NA | NA | 282 | 321 | 307 | 6 | q14.2 |
| 176 | NLGN4Y | 368 | 2 | −1 | 645 | NA | NA | 2.4188 | NA | 734 | 339 | 275 | 312 | 24 | q11.221 |
| 177 | LZTS1 | 118 | NA | NA | NA | NA | NA | NA | NA | NA | 300 | 316 | 316 | 8 | p21.3 |
| 178 | FBXL18 | 56 | NA | NA | NA | NA | NA | 1.8646 | NA | 652 | 323 | 294 | 317 | 7 | p22.1 |
| 179 | TBC1D10B | 261 | NA | NA | NA | NA | NA | 1.8243 | NA | 573 | 278 | 321 | 321 | 16 | p11.2 |
| 180 | WDR59 | 272 | 2.1 | −1 | 653 | NA | NA | NA | NA | NA | 304 | 320 | 322 | 16 | q23.1 |
| 181 | BLK | 101 | 2.1 | 1 | 671 | NA | NA | NA | NA | NA | 315 | 314 | 325 | 8 | p23.1 |
| 182 | MEPCE | 71 | NA | NA | NA | 2.2 | −1 | 2.1134 | 682 | 782 | 350 | 285 | 327 | 7 | q22.1 |
| 183 | DLGAP2 | 91 | NA | NA | NA | NA | NA | NA | NA | NA | 356 | 286 | 330 | 8 | p23.3 |
| 184 | ZFAT | 234 | 2.5 | 1 | 796 | NA | NA | NA | NA | NA | 325 | 317 | 331 | 8 | q24.22 |
| 185 | FASN | 348 | NA | NA | NA | NA | NA | 3.0027 | NA | 963 | 296 | 350 | 332 | 17 | q25.3 |
| 186 | GIGYF1 | 81 | NA | NA | NA | NA | NA | 2.7127 | NA | 957 | 335 | 311 | 335 | 7 | q22.1 |
| 187 | ANXA13 | 219 | 2.1 | 1 | 682 | NA | NA | NA | NA | NA | 310 | 345 | 336 | 8 | q24.13 |
| 188 | CDYL2 | 280 | 2.5 | −1 | 699 | NA | NA | NA | NA | NA | 316 | 351 | 339 | 16 | q23.2 |
| 189 | TOX | 161 | NA | NA | NA | 4.6 | 1 | NA | 999 | 974 | 338 | 342 | 349 | 8 | q12.1 |
| 190 | NKX2-6 | 143 | 2.4 | 1 | 870 | 2.1 | 1 | NA | 591 | 955 | 340 | 366 | 357 | 8 | p21.2 |
| 191 | RAI1YL | 191 | 2.8 | −1 | 985 | 5.8 | 1 | NA | 996 | NA | 345 | 362 | 359 | 8 | q21.2 |
| 192 | TBC1D22A | 361 | NA | NA | NA | 3.4 | 1 | NA | 994 | NA | 367 | 346 | 363 | 22 | q13.31 |
| 193 | TFE3 | 363 | 1 | −1 | 1000 | NA | NA | NA | NA | NA | 362 | 353 | 364 | 23 | p11.23 |
| 194 | KCNAB1 | 14 | NA | NA | NA | NA | NA | 3.5399 | NA | 998 | 363 | 367 | 367 | 3 | q25.31 |
| 195 | SULF1 | 166 | 5.2 | 1 | NA | NA | NA | 8.9116 | NA | 952 | 6 | 4 | 3 | 8 | q13.2 |
| 196 | RAB5C | 342 | NA | NA | NA | NA | NA | NA | NA | NA | 14 | 3 | 5 | 17 | q21.2 |
| 197 | DHX58 | 339 | NA | NA | NA | 3.6 | 1 | NA | 974 | NA | 21 | 16 | 16 | 17 | q21.2 |
| 198 | ASAP1 | 224 | 2.6 | −1 | 832 | 3.8 | 1 | 2.7921 | 955 | 976 | 23 | 20 | 20 | 8 | q24.21 |
| 199 | CA5A | 313 | NA | NA | NA | 2.4 | 1 | NA | NA | NA | 28 | 26 | 26 | 16 | q24.2 |
| 200 | C6orf18 | 53 | NA | NA | NA | 2 | 1 | NA | 997 | 806 | 36 | 36 | 36 | 6 | q27 |
| 201 | NCOA2 | 169 | 3.2 | 1 | 999 | 3.3 | 1 | NA | 999 | 715 | 35 | 40 | 37 | 8 | q13.3 |
| 202 | PKD1L2 | 283 | 4.9 | −1 | 901 | 3.1 | −1 | NA | 901 | 957 | 41 | 45 | 42 | 16 | q23.3 |
| 203 | BANP | 314 | 2.6 | −1 | 925 | NA | NA | NA | NA | 989 | 42 | 49 | 46 | 16 | q24.2 |
| 204 | KIAA1967 | 133 | 2.8 | −1 | NA | 2.8 | −1 | 3.1195 | NA | 936 | 50 | 57 | 52 | 8 | p21.3 |
| 205 | COPG2 | 89 | NA | NA | NA | NA | NA | NA | NA | NA | 56 | 52 | 53 | 7 | q32.2 |
| 206 | ZNF706 | 205 | 2.7 | −1 | 869 | 2.4 | −1 | NA | 889 | NA | 53 | 56 | 54 | 8 | q22.3 |
| 207 | GAN | 285 | NA | NA | NA | 2.8 | 1 | NA | 902 | NA | 49 | 61 | 55 | 16 | q23.2 |
| 208 | PLCG2 | 286 | 2.9 | −1 | 833 | 2.7 | −1 | NA | 913 | NA | 61 | 50 | 56 | 16 | q23.2 |

| | | | | | | | | | | | | | | |
|---|---|---|---|---|---|---|---|---|---|---|---|---|---|---|
| 209 | C19orf57 | 356 | NA | NA | NA | NA | NA | NA | 58 | 58 | 59 | 19 | p13.12 |
| 210 | PDGFRL | 111 | 4.8 | -1 | 998 | NA | NA | NA | 62 | 55 | 60 | 8 | p22 |
| 211 | ESD | 249 | NA | NA | NA | NA | NA | NA | 65 | 59 | 62 | 13 | q14.2 |
| 212 | CPA5 | 85 | 1.7 | -1 | 507 | 2.8 | -1 | 992 | 70 | 63 | 67 | 7 | q32.2 |
| 213 | BIN3 | 134 | 4.3 | 1 | 1000 | NA | NA | NA | 71 | 73 | 70 | 8 | p21.3 |
| 214 | ZFHX4 | 184 | 3.8 | 1 | 1000 | NA | NA | NA | 74 | 76 | 73 | 8 | q21.11 |
| 215 | CPA6 | 163 | 3.4 | -1 | 997 | NA | NA | NA | 77 | 81 | 75 | 8 | q13.2 |
| 216 | EYA1 | 172 | 3.5 | 1 | 999 | NA | NA | NA | 73 | 89 | 77 | 8 | q13.3 |
| 217 | CHRNA2 | 153 | 4 | -1 | 1000 | NA | NA | NA | 76 | 87 | 79 | 8 | p21.2 |
| 218 | TNKS | 97 | 4.1 | 1 | 1000 | NA | NA | NA | 87 | 84 | 84 | 8 | p23.1 |
| 219 | HNF4G | 183 | NA | NA | NA | NA | NA | NA | 103 | 72 | 87 | 8 | q21.11 |
| 220 | LRCH1 | 248 | 3.9 | -1 | 991 | NA | NA | 801 | 79 | 94 | 88 | 13 | q14.13 |
| 221 | ADRA1A | 149 | 3.3 | -1 | 997 | NA | NA | NA | 96 | 79 | 89 | 8 | p21.2 |
| 222 | EPHX2 | 154 | NA | NA | NA | NA | NA | NA | 89 | 88 | 90 | 8 | p21.1 |
| 223 | SORBS3 | 130 | NA | NA | NA | NA | NA | NA | 83 | 95 | 91 | 8 | p21.3 |
| 224 | GRIA1 | 27 | 3 | 1 | NA | 3 | -1 | 957 | 88 | 96 | 93 | 5 | q32.1 |
| 225 | PDLIM2 | 131 | 3.7 | -1 | 971 | NA | NA | NA | 94 | 91 | 94 | 8 | p21.3 |
| 226 | MTMR7 | 109 | NA | NA | NA | 2.9 | -1 | 993 | 86 | 106 | 96 | 8 | p22 |
| 227 | FBXO24 | 76 | 4.9 | 1 | 1000 | NA | NA | NA | 118 | 85 | 99 | 7 | q22.1 |
| 228 | CRISPLD1 | 182 | 3.2 | -1 | 976 | NA | NA | 817 | 95 | 124 | 107 | 8 | q21.11 |
| 229 | DPYS | 211 | NA | NA | NA | NA | NA | NA | 92 | 129 | 109 | 8 | q22.3 |
| 230 | DTNA | 351 | NA | NA | NA | 2.5 | -1 | 987 | 102 | 125 | 112 | 18 | q12.1 |
| 231 | KLHDC4 | 311 | NA | NA | NA | 2.9 | -1 | 941 | 116 | 111 | 113 | 16 | q24.2 |
| 232 | CYBA | 319 | NA | NA | NA | 2.4 | -1 | 908 | 117 | 121 | 118 | 16 | q24.3 |
| 233 | JPH3 | 310 | 2.4 | -1 | 766 | NA | NA | NA | 101 | 142 | 120 | 16 | q24.2 |
| 234 | TMEM120A | 64 | NA | NA | NA | 1.7093 | 1 | 511 | 128 | 115 | 121 | 7 | q11.23 |
| 235 | MTUS1 | 112 | 3.6 | -1 | 976 | NA | NA | NA | 143 | 116 | 127 | 8 | p22 |
| 236 | C8orf34 | 165 | 6 | 1 | 1000 | NA | NA | NA | 126 | 132 | 128 | 8 | q13.2 |
| 237 | GRHL2 | 206 | NA | NA | NA | 2.4 | 1 | 790 | 125 | 140 | 132 | 8 | q22.3 |
| 238 | CPA2 | 83 | 3.3 | 1 | 993 | NA | NA | NA | 153 | 117 | 133 | 7 | q32.2 |
| 239 | NAT2 | 115 | 3.3 | -1 | 967 | NA | NA | NA | 140 | 134 | 134 | 8 | p22 |
| 240 | DPYSL2 | 148 | NA | NA | NA | 2.5 | -1 | 839 | 155 | 122 | 135.5 | 8 | p21.2 |
| 241 | ZDHHC7 | 300 | NA | NA | NA | NA | NA | NA | 159 | 123 | 138 | 16 | q24.1 |
| 242 | ELP3 | 158 | 3.4 | -1 | 939 | 1.7 | -1 | 501 | 166 | 118 | 139 | 8 | p21.1 |
| 243 | RHOBTB2 | 136 | 2.7 | -1 | 921 | NA | NA | NA | 133 | 150 | 142 | 8 | p21.3 |
| 244 | NEIL2 | 103 | 2.7 | 1 | 929 | NA | NA | 896 | 150 | 135 | 143 | 8 | p23.1 |
| 245 | HR | 122 | 2.4 | -1 | 766 | 2.7 | -1 | NA | 186 | 112 | 145 | 8 | p21.3 |
| 246 | EFR3A | 226 | 3.1 | 1 | 985 | NA | NA | 988 | 144 | 146 | 146 | 8 | q24.22 |
| 247 | STMN4 | 150 | 3.3 | 1 | 994 | NA | NA | NA | 162 | 131 | 147 | 8 | p21.2 |
| 248 | PRDM14 | 168 | 4.7 | -1 | 996 | 3 | 1 | 791 | 135 | 171 | 152 | 8 | q13.3 |
| 249 | MARVELD2 | 35 | 1.8 | -1 | NA | 2.2 | -1 | NA | 142 | 164 | 154 | 5 | q13.2 |
| 250 | SLC39A14 | 128 | 3.1 | 1 | 560 | 2.5 | -1 | 938 | 152 | 160 | 155 | 8 | p21.3 |
| 251 | ACTL6B | 80 | 3.1 | -1 | 945 | 1.7362 | 1 | 538 | 168 | 158 | 159 | 7 | q22.1 |
| 252 | TUSC3 | 108 | NA | NA | NA | 2.2 | -1 | NA | 157 | 170 | 160 | 8 | p22 |
| 253 | COX4NB | 305 | NA | NA | NA | 2.5 | -1 | NA | 148 | 181 | 161 | 16 | q24.1 |
| 254 | XKR9 | 171 | 2.7 | 1 | 929 | 2.6 | -1 | NA | 165 | 163 | 162 | 8 | q13.3 |
| 255 | C16orf46 | 281 | NA | NA | NA | NA | NA | 768 | 151 | 183 | 164 | 16 | q23.2 |
| 256 | TAF9 | 33 | NA | NA | NA | 2.6 | -1 | 963 | 175 | 162 | 166 | 5 | q13.2 |
| 257 | KCNQ3 | 228 | 6 | 1 | 1000 | NA | NA | NA | 167 | 180 | 169 | 8 | q24.22 |
| 258 | UTRN | 50 | NA | NA | NA | 2.3296 | -1 | 766 | 174 | 172 | 170 | 6 | q13.2 |
| 259 | RAD17 | 34 | NA | NA | NA | NA | NA | 969 | 182 | 174 | 172 | 5 | q13.2 |
| 260 | ZFPM1 | 315 | NA | NA | NA | 2.6 | -1 | 924 | 146 | 219 | 175 | 16 | q24.2 |
| 261 | PTDSS1 | 197 | 2.5 | 1 | 874 | NA | NA | NA | 184 | 177 | 179 | 8 | q22.1 |

| | | | | | | | | | | | |
|---|---|---|---|---|---|---|---|---|---|---|---|
| 262 | IRF8 | 307 | NA | NA | 2.5 | -1 | 976 | NA | NA | 199 | 169 | 181 | 16 | q24.1 |
| 263 | YWHAZ | 204 | NA | NA | 2.2 | 1 | 722 | NA | NA | 204 | 166 | 182 | 8 | q22.3 |
| 264 | MRPS36 | 30 | NA | NA | 2.6 | -1 | 962 | NA | NA | 195 | 175 | 183 | 5 | q13.2 |
| 265 | LACTB2 | 170 | 932 | 1 | NA | -1 | 914 | NA | NA | 160 | 223 | 187 | 8 | q13.3 |
| 266 | SNAI3 | 321 | NA | NA | 2.4 | NA | NA | NA | NA | 231 | 156 | 190 | 16 | q24.3 |
| 267 | TMEM71 | 229 | 993 | 1 | 2.9 | NA | NA | NA | NA | 180 | 207 | 194 | 8 | q24.22 |
| 268 | PREX2 | 164 | NA | NA | 7.5 | 1 | NA | NA | NA | 190 | 199 | 195 | 8 | q13.2 |
| 269 | CPA1 | 86 | 1000 | 1 | NA | NA | NA | NA | NA | 228 | 173 | 199 | 7 | q32.2 |
| 270 | PHF20L1 | 230 | NA | NA | 2.8 | -1 | NA | 2.0683 | 716 | 198 | 200 | 200 | 8 | q24.22 |
| 271 | KIAA0513 | 301 | 901 | 1 | NA | 1 | 816 | NA | NA | 212 | 188 | 202 | 16 | q24.1 |
| 272 | PI15 | 181 | NA | NA | 3 | -1 | NA | NA | NA | 238 | 179 | 206 | 8 | q21.11 |
| 273 | PCM1 | 113 | 991 | -1 | 1.7 | NA | NA | NA | NA | 183 | 234 | 207 | 8 | p22 |
| 274 | SH2D4A | 117 | 529 | -1 | 2.9 | NA | 939 | NA | NA | 249 | 172 | 208 | 8 | p21.3 |
| 275 | C16orf74 | 304 | 908 | NA | NA | NA | 822 | NA | NA | 202 | 214 | 209 | 16 | q24.1 |
| 276 | TP63 | 18 | NA | NA | 3 | -1 | NA | 1.8675 | 570 | 203 | 228 | 211 | 3 | q28 |
| 277 | DACH1 | 254 | NA | NA | 2.2 | -1 | 774 | NA | NA | 252 | 185 | 212 | 13 | q21.33 |
| 278 | TNFRSF10A | 138 | NA | NA | 2.2 | -1 | NA | 1.9653 | NA | 245 | 196 | 214 | 8 | p21.3 |
| 279 | MDH2 | 66 | NA | NA | NA | 1 | 728 | NA | NA | 236 | 208 | 218 | 7 | q11.23 |
| 280 | PAG1 | 189 | NA | NA | 2 | NA | 776 | NA | NA | 173 | 290 | 221 | 8 | q21.13 |
| 281 | SLC25A37 | 142 | 845 | -1 | 2.6 | NA | NA | NA | NA | 226 | 222 | 222 | 8 | p21.2 |
| 282 | BCAR1 | 273 | 846 | -1 | 2.5 | NA | NA | NA | NA | 240 | 213 | 225 | 16 | q23.1 |
| 283 | COX4I1 | 306 | NA | NA | NA | -1 | 911 | NA | NA | 178 | 289 | 226 | 16 | q24.1 |
| 284 | EIF4H | 59 | NA | NA | 2.6 | -1 | NA | 2.0065 | NA | 224 | 236 | 227 | 7 | q11.23 |
| 285 | ZC3H18 | 317 | NA | NA | 2.1 | -1 | 878 | NA | 775 | 217 | 244 | 228 | 16 | q24.2 |
| 286 | STMN2 | 186 | 962 | 1 | NA | NA | NA | NA | NA | 284 | 198 | 230 | 8 | q21.13 |
| 287 | AFG3L1 | 335 | NA | NA | 2.3 | -1 | 947 | NA | NA | 254 | 224 | 231 | 16 | q24.3 |
| 288 | HSD17B2 | 287 | 791 | -1 | 2.6 | -1 | NA | NA | NA | 229 | 259 | 236 | 16 | q23.3 |
| 289 | MVD | 320 | NA | NA | NA | -1 | 901 | NA | NA | 223 | 266 | 237 | 16 | q24.3 |
| 290 | DLC1 | 106 | 1000 | -1 | 2.3 | NA | NA | NA | NA | 207 | 288 | 238 | 8 | p22 |
| 291 | EPHA7 | 44 | NA | NA | 6.5 | NA | NA | 1.7755 | 529 | 237 | 252 | 239 | 6 | q16.1 |
| 292 | TRIM35 | 151 | NA | NA | NA | -1 | NA | NA | NA | 209 | 287 | 241 | 8 | p21.2 |
| 293 | LRRC50 | 293 | 926 | -1 | 2.6 | NA | NA | NA | NA | 232 | 262 | 243 | 16 | q24.1 |
| 294 | CNGB3 | 192 | 830 | -1 | 2.4 | NA | NA | NA | NA | 319 | 191 | 244 | 8 | q21.3 |
| 295 | ASCC3 | 47 | 534 | 1 | 1.8 | NA | NA | 1.7954 | 535 | 246 | 249 | 245 | 6 | q16.3 |
| 296 | RFC2 | 61 | NA | NA | NA | 1 | NA | 1.8399 | 625 | 208 | 295 | 246 | 7 | q11.23 |
| 297 | CLEC3A | 278 | 781 | -1 | 2.3 | NA | 639 | NA | NA | 267 | 232 | 247 | 16 | q23.1 |
| 298 | IL17C | 318 | NA | NA | NA | -1 | 819 | NA | NA | 244 | 256 | 249 | 16 | q24.3 |
| 299 | BMP1 | 125 | NA | NA | 2.6 | -1 | NA | NA | NA | 259 | 242 | 250 | 8 | p21.3 |
| 300 | CPA4 | 84 | NA | NA | NA | -1 | NA | 1.9432 | 632 | 262 | 261 | 251 | 7 | q32.2 |
| 301 | OC90 | 227 | 640 | 1 | 1.9 | NA | NA | NA | NA | 292 | 243 | 253 | 8 | q24.22 |
| 302 | HEPH | 364 | 537 | 1 | 1.8 | NA | 635 | NA | NA | 277 | 220 | 254 | 23 | q12 |
| 303 | LRP12 | 212 | NA | NA | 2 | 1 | NA | NA | NA | 317 | 233 | 257 | 8 | q22.3 |
| 304 | AGFG2 | 74 | NA | NA | NA | NA | NA | 2.2839 | 749 | 257 | 212 | 258 | 7 | q22.1 |
| 305 | TRPA1 | 174 | 803 | 1 | 2.3 | -1 | NA | NA | NA | 268 | 263 | 260 | 8 | q13.3 |
| 306 | GINS2 | 303 | NA | NA | NA | -1 | 861 | NA | NA | 286 | 253 | 261 | 16 | q24.1 |
| 307 | CENPH | 29 | NA | NA | NA | NA | 693 | NA | NA | 222 | 238 | 263 | 5 | q13.2 |
| 308 | KLHL36 | 297 | NA | NA | 1.8 | -1 | 606 | NA | NA | 258 | 312 | 264 | 16 | q24.1 |
| 309 | ARHGEF10L | 2 | NA | NA | 2.1 | -1 | 730 | NA | NA | 302 | 269 | 265 | 1 | p36.13 |
| 310 | TRAPPC2L | 326 | NA | NA | 1.9 | -1 | 670 | NA | NA | 230 | 256 | 267 | 16 | q24.3 |
| 311 | TCF25 | 332 | 603 | -1 | 2.1 | -1 | 821 | NA | NA | 272 | 264 | 268 | 16 | q24.3 |
| 312 | TNFRSF10D | 137 | NA | NA | 1.9 | -1 | NA | NA | NA | 288 | 250 | 269 | 8 | p21.3 |
| 313 | MYOM2 | 93 | 705 | -1 | 2.1 | -1 | NA | NA | NA | 295 | 245 | 272 | 8 | p23.3 |
| 314 | GCSH | 282 | NA | NA | 1.9 | NA | 673 | NA | NA | 248 | 296 | 272 | 16 | q23.2 |

-continued

| | | | | | | | | | | | | | | | | | | | | |
|---|---|---|---|---|---|---|---|---|---|---|---|---|---|---|---|---|---|---|---|---|
| 315 | KIAA1609 | 296 | NA | NA | NA | NA | NA | -1 | 1.9 | NA | NA | NA | 641 | -1 | NA | NA | 260 | 284 | 274 | 16 | q24.1 |
| 316 | FANCA | 330 | NA | NA | NA | NA | NA | -1 | 1.9 | NA | NA | NA | 612 | -1 | NA | NA | 299 | 247 | 275 | 16 | q24.3 |
| 317 | ERI1 | 96 | 1.9 | -1 | 607 | NA | NA | NA | NA | NA | NA | NA | NA | NA | NA | NA | 312 | 239 | 276 | 8 | p23.1 |
| 318 | HSDL1 | 292 | NA | NA | NA | NA | NA | -1 | 2 | NA | NA | NA | 685 | -1 | NA | NA | 273 | 278 | 278 | 16 | q24.1 |
| 319 | KIAA0182 | 302 | NA | NA | NA | NA | NA | -1 | 2 | NA | NA | NA | 781 | -1 | NA | NA | 305 | 251 | 281 | 16 | q24.1 |
| 320 | CBFA2T3 | 327 | NA | NA | NA | NA | NA | -1 | 1.9 | NA | NA | NA | 698 | -1 | NA | NA | 274 | 297 | 286 | 16 | q24.3 |
| 321 | EGR3 | 135 | NA | NA | NA | NA | NA | -1 | 2 | NA | NA | NA | 751 | -1 | NA | NA | 308 | 267 | 289 | 8 | p21.3 |
| 322 | PCOLCE | 77 | NA | NA | NA | NA | NA | NA | NA | NA | 1.8050 | 1 | NA | NA | NA | NA | 294 | 281 | 290 | 7 | q22.1 |
| 323 | C16orf85 | 316 | NA | NA | NA | NA | NA | -1 | 2.1 | NA | NA | NA | 801 | -1 | NA | NA | 290 | 291 | 295 | 16 | q24.2 |
| 324 | HMBOX1 | 159 | 1.8 | -1 | 553 | NA | NA | NA | NA | NA | NA | NA | NA | NA | NA | NA | 287 | 306 | 300 | 8 | p21.1 |
| 325 | MTMR9 | 100 | 1.9 | -1 | 674 | NA | NA | NA | NA | NA | NA | NA | NA | NA | NA | NA | 343 | 257 | 301 | 8 | p23.1 |
| 326 | MSC | 173 | NA | NA | 675 | NA | 1 | NA | NA | NA | NA | NA | NA | NA | NA | NA | 291 | 305 | 302 | 8 | q13.3 |
| 327 | ST3GAL2 | 269 | 2 | -1 | 774 | NA | -1 | NA | NA | NA | NA | NA | NA | NA | NA | NA | 269 | 340 | 308 | 16 | q22.1 |
| 328 | FOXF1 | 308 | 2.4 | NA | NA | NA | NA | -1 | 2.2 | NA | NA | NA | 894 | -1 | NA | NA | 344 | 270 | 309 | 16 | q24.1 |
| 329 | C8orf58 | 132 | NA | NA | NA | NA | 1 | NA | NA | NA | NA | NA | NA | NA | NA | NA | 334 | 279 | 310 | 8 | p21.3 |
| 330 | KCTD9 | 145 | 2 | -1 | 663 | NA | NA | NA | 3 | NA | NA | NA | 999 | -1 | NA | NA | 271 | 344 | 311 | 8 | p21.2 |
| 331 | ANGPT1 | 214 | 2.4 | NA | 816 | NA | NA | NA | NA | NA | NA | NA | NA | NA | NA | NA | 333 | 282 | 313 | 8 | q23.1 |
| 332 | GDAP1 | 180 | 2 | 1 | 663 | NA | NA | NA | NA | NA | NA | NA | NA | NA | NA | NA | 283 | 333 | 314 | 8 | q21.11 |
| 333 | RNF166 | 322 | NA | NA | NA | NA | NA | -1 | 2.2 | NA | NA | NA | 877 | -1 | NA | NA | 360 | 360 | 315 | 16 | q24.3 |
| 334 | KLHL1 | 253 | NA | NA | NA | NA | NA | NA | NA | -1 | 1.8637 | 1 | NA | NA | NA | NA | 293 | 325 | 318 | 13 | q21.33 |
| 335 | LOXL2 | 140 | NA | NA | NA | NA | NA | NA | 1.9 | NA | NA | NA | 675 | -1 | NA | NA | 322 | 298 | 319 | 8 | p21.3 |
| 336 | WISP1 | 233 | 2.2 | 1 | 777 | NA | NA | NA | NA | NA | NA | NA | NA | NA | NA | NA | 280 | 343 | 320 | 8 | q24.22 |
| 337 | C8orf80 | 157 | 3.6 | -1 | 957 | NA | NA | NA | NA | NA | NA | NA | NA | NA | NA | NA | 357 | 274 | 323 | 8 | p21.1 |
| 338 | LAT2 | 60 | NA | NA | NA | NA | NA | NA | NA | -1 | 1.9646 | 1 | NA | NA | NA | NA | 328 | 300 | 324 | 7 | q11.23 |
| 339 | USP10 | 298 | 2.3 | -1 | 691 | NA | NA | NA | NA | NA | NA | NA | 673 | -1 | NA | NA | 321 | 310 | 326 | 16 | q24.1 |
| 340 | CDH15 | 328 | NA | NA | NA | NA | NA | -1 | 1.9 | NA | NA | NA | NA | NA | NA | NA | 330 | 303 | 328 | 16 | q24.3 |
| 341 | WFDC1 | 294 | 2.3 | -1 | 713 | NA | NA | NA | NA | NA | NA | NA | NA | NA | NA | NA | 311 | 327 | 329 | 16 | q24.1 |
| 342 | C7orf51 | 73 | NA | NA | NA | NA | NA | NA | NA | -1 | 2.1914 | 1 | NA | NA | NA | NA | 307 | 339 | 333 | 7 | q22.1 |
| 343 | EBF2 | 147 | 5.1 | -1 | 999 | NA | NA | NA | NA | NA | NA | NA | NA | NA | NA | NA | 309 | 337 | 334 | 8 | p21.2 |
| 344 | CCDC125 | 32 | 2 | NA | NA | NA | NA | NA | NA | NA | NA | NA | 721 | -1 | NA | NA | 336 | 319 | 337 | 5 | q13.2 |
| 345 | LGI3 | 124 | NA | NA | 629 | NA | 1 | NA | NA | NA | NA | NA | 678 | -1 | NA | NA | 332 | 323 | 338 | 8 | p21.3 |
| 346 | NUDT18 | 121 | 2.3 | 1 | NA | NA | NA | NA | 2 | NA | NA | NA | 786 | -1 | NA | NA | 314 | 354 | 340 | 8 | p21.3 |
| 347 | PHYHIP | 126 | 2.2 | -1 | NA | NA | NA | NA | 2.2 | NA | NA | NA | 860 | -1 | NA | NA | 361 | 308 | 341 | 8 | p21.3 |
| 348 | PILRA | 70 | NA | NA | NA | NA | NA | NA | NA | NA | 1.8998 | 1 | NA | NA | NA | NA | 353 | 318 | 342 | 7 | q22.1 |
| 349 | KAT2A | 340 | NA | NA | NA | NA | NA | 1 | 2.3 | NA | 3.1978 | 1 | NA | NA | NA | NA | 318 | 357 | 343 | 17 | q21.2 |
| 350 | CSMD3 | 216 | 4.9 | 1 | 998 | NA | NA | NA | NA | NA | NA | NA | 809 | -1 | NA | NA | 351 | 324 | 344 | 8 | q23.3 |
| 351 | REEP4 | 123 | NA | NA | NA | NA | NA | -1 | 2.5 | NA | NA | NA | 847 | -1 | NA | NA | 324 | 352 | 345 | 8 | p21.3 |
| 352 | TUBB3 | 333 | NA | NA | NA | NA | NA | -1 | 2.6 | NA | NA | NA | 843 | -1 | NA | NA | 348 | 328 | 346 | 16 | q24.3 |
| 353 | CDT1 | 324 | NA | NA | NA | NA | NA | -1 | 2 | NA | NA | NA | 745 | -1 | NA | NA | 365 | 313 | 347 | 16 | q24.3 |
| 354 | EDA2R | 365 | 2 | NA | NA | NA | NA | NA | NA | NA | NA | NA | NA | NA | NA | NA | 349 | 331 | 348 | 23 | q12 |
| 355 | DUS1L | 347 | NA | NA | NA | NA | NA | -1 | NA | NA | 2.2705 | 1 | NA | NA | NA | 904 | 364 | 322 | 350 | 17 | q25.3 |
| 356 | LRCH4 | 75 | NA | NA | NA | NA | NA | NA | NA | NA | 2.2304 | 1 | NA | NA | NA | 831 | 342 | 349 | 351 | 7 | q22.1 |
| 357 | TMEM75 | 223 | 3.5 | 1 | 992 | NA | NA | NA | 2.3 | NA | NA | NA | NA | NA | NA | NA | 337 | 356 | 352 | 8 | q24.21 |
| 358 | NUDT7 | 277 | 2.2 | -1 | 730 | NA | NA | NA | NA | NA | NA | NA | 809 | -1 | NA | 966 | 355 | 338 | 353 | 16 | q23.1 |
| 359 | TSGA14 | 87 | NA | NA | NA | NA | NA | NA | NA | NA | 9.3754 | 1 | NA | NA | NA | NA | 354 | 341 | 354 | 7 | q32.2 |
| 360 | CDC42BPG | 242 | NA | NA | NA | NA | NA | NA | NA | NA | 2.3279 | 1 | NA | NA | NA | 813 | 360 | 336 | 355 | 11 | q13.1 |
| 361 | TSC22D4 | 72 | NA | NA | NA | NA | NA | NA | NA | NA | 2.1304 | 1 | NA | NA | NA | 867 | 341 | 359 | 356 | 7 | q22.1 |
| 362 | NOTUM | 345 | NA | NA | NA | NA | NA | NA | NA | NA | 2.6756 | 1 | NA | NA | NA | 963 | 358 | 348 | 358 | 17 | q25.3 |
| 363 | HSPB9 | 341 | NA | NA | NA | NA | NA | NA | NA | NA | 2.9366 | 1 | NA | NA | NA | 987 | 346 | 361 | 360 | 17 | q21.2 |
| 364 | TFR2 | 79 | NA | NA | NA | NA | NA | NA | NA | NA | 2.6230 | 1 | NA | NA | NA | 950 | 352 | 355 | 361 | 7 | q22.1 |
| 365 | SLA | 232 | 2.2 | 1 | 786 | NA | NA | NA | NA | NA | NA | NA | NA | NA | NA | NA | 347 | 365 | 362 | 8 | q24.22 |

-continued

| Final-RANK | gene | gene-start | gene-end | genesBtwn | contig | clump-index | dist-prev | dist-next | min-dist-to-RGL | Index0-Proxy1 | NYU-Zadjust | MSKs1-Zadjust | MSKs2-Zadjust |
|---|---|---|---|---|---|---|---|---|---|---|---|---|---|
| 366 | WWOX | 279 | -1 | 1000 | | | | NA | NA | 364 | 365 | 16 | q23.1 |
| 367 | POU5F1B | 221 | 1 | 989 | | | | NA | NA | 358 | 366 | 8 | q24.21 |
| 368 | OPHN1 | 367 | 1 | 999 | | | | NA | NA | 368 | 368 | 23 | q12 |
| 1 | PPP3CC | 22354541 | 22454580 | 0 | 1 | 26 | 10616 | −7079 | −7079 | 1 | 0.52 | 0.29 | NA |
| 2 | SLCO5A1 | 70447129 | 70909762 | 0 | 1 | 33 | 216812 | −11428 | −11428 | 1 | 1.63 | 1.16 | NA |
| 3 | SLC7A5 | 86421131 | 86460615 | 0 | 1 | 58 | 18511 | −64075 | 18511 | 1 | 0.00 | 0.47 | NA |
| 4 | SLC7A2 | 17398975 | 17472357 | 0 | 1 | 21 | 6086 | −83768 | 6086 | 1 | 1.10 | 0.42 | NA |
| 5 | CRISPLD2 | 83411113 | 83500614 | 0 | 1 | 56 | 64959 | −40087 | −40087 | 1 | 0.25 | 0.42 | NA |
| 6 | CDH13 | 81439761 | 82387705 | 1 | 0 | NA | 102526 | −750123 | 102526 | 1 | 3.67 | NA | NA |
| 7 | CDH8 | 60244866 | 60628240 | 82 | 0 | NA | 7528258 | −3524069 | −3524069 | 1 | NA | NA | 0.87 |
| 8 | CDH2 | 23784934 | 24011189 | 19 | 0 | NA | 5673873 | NA | 5673873 | 1 | NA | NA | 0.70 |
| 9 | ASAH1 | 17958214 | 17986787 | 1 | 1 | 22 | 306248 | −22652 | −22652 | 1 | 3.10 | NA | NA |
| 10 | KCNB2 | 73642524 | 74012880 | 1 | 1 | 34 | 352193 | −492151 | 352193 | 1 | 2.91 | NA | 0.88 |
| 11 | KCNH4 | 37562439 | 37586822 | 3 | 0 | 64 | 7810 | −1891 | −1891 | 1 | NA | NA | 0.38 |
| 12 | KCTD8 | 43870683 | 44145581 | 0 | 1 | NA | 1800760 | −3032257 | 1800760 | 1 | NA | NA | NA |
| 13 | JPH1 | 75309493 | 75396117 | 1 | 1 | 35 | 29056 | −262534 | 29056 | 1 | 2.37 | NA | 0.58 |
| 14 | MEST | 129913282 | 129933363 | 0 | 1 | 13 | 41 | −45149 | 41 | 1 | NA | NA | NA |
| 15 | NCALD | 102767947 | 103206311 | 0 | 1 | 40 | 128437 | −16952 | −16952 | 1 | 2.03 | 0.42 | 0.70 |
| 16 | COL19A1 | 70633169 | 70978878 | 1 | 1 | NA | 4871884 | NA | 4871884 | 1 | NA | NA | NA |
| 17 | MAP3K7 | 91282074 | 91353628 | 20 | 0 | 5 | 2654236 | −7084576 | 2654236 | 1 | NA | NA | 0.56 |
| 18 | YWHAG | 75794053 | 75826252 | 0 | 1 | NA | 23787222 | −260189 | −260189 | 1 | NA | NA | 0.34 |
| 19 | NOL4 | 29685062 | 30057513 | 126 | 0 | 67 | 269766 | −5673873 | 269766 | 1 | NA | NA | 0.98 |
| 20 | ENOX1 | 42685704 | 43259044 | 0 | 1 | 14 | 2766260 | −4175452 | 2766260 | 1 | NA | NA | 2.12 |
| 21 | CSMD1 | 2780282 | 3258996 | 18 | 0 | 20 | 5420413 | −699503 | −699503 | 1 | NA | NA | 1.44 |
| 22 | SGCZ | 13991744 | 15140219 | 46 | 0 | 8 | 301882 | −574978 | 301882 | 1 | 1.49 | NA | 0.74 |
| 23 | PDE10A | 165995578 | 166660766 | 0 | 1 | 49 | NA | −17665 | −17665 | 1 | NA | NA | 1.49 |
| 24 | PCDH9 | 65774970 | 66702578 | 0 | 1 | 48 | 2470149 | −6138850 | 2470149 | 1 | NA | NA | 1.38 |
| 25 | HTR2A | 46305514 | 46368176 | 44 | 0 | 53 | 12769542 | −36146 | −36146 | 1 | NA | NA | 0.62 |
| 26 | HIP1 | 75001345 | 75206215 | 5 | 0 | NA | 248023 | −1543149 | 248023 | 1 | NA | NA | 1.32 |
| 27 | CD226 | 65681175 | 65775140 | NA | 0 | NA | NA | −12833135 | −12833135 | 1 | NA | NA | 0.63 |
| 28 | DCC | 48121156 | 49311780 | 10 | 0 | 68 | 3157834 | −17395350 | 3157834 | 1 | NA | NA | 2.79 |
| 29 | CC2D1A | 13878014 | 13902691 | 1 | 0 | 30 | 30662 | −105 | −105 | 1 | NA | NA | 1.02 |
| 30 | PTK2B | 27224916 | 27372820 | 0 | 1 | NA | 376 | −165 | −165 | 1 | NA | NA | NA |
| 31 | BCMO1 | 79829797 | 79882248 | 0 | 1 | NA | 23828 | −18320 | −18320 | 1 | 3.04 | NA | NA |
| 32 | MACROD1 | 63522607 | 63690109 | 1 | 0 | 11 | 19764 | −81715 | 19764 | 1 | 0.42 | 0.80 | 0.41 |
| 33 | GRID2 | 93444831 | 94914730 | 186 | 0 | NA | 60460408 | −30824069 | −30824069 | 1 | NA | 0.05 | 1.77 |
| 34 | DIAPH3 | 59137718 | 59636120 | 2 | 0 | NA | 6138850 | −12769542 | 6138850 | 1 | NA | NA | 0.60 |
| 35 | PILRB | 99771673 | 99803388 | 0 | 1 | NA | 5616 | −111895 | 5616 | 1 | NA | NA | 0.44 |
| 36 | MEIS2 | 34970519 | 35189740 | 193 | 0 | NA | 24742144 | NA | 24742144 | 1 | 1.76 | NA | 1.00 |
| 37 | MSRA | 9449189 | 10323803 | 4 | 1 | 16 | 697587 | −271923 | −271923 | 1 | NA | NA | NA |
| 38 | DPYD | 97315890 | 98159203 | 19 | 0 | NA | 4955408 | −7289745 | 4955408 | 1 | NA | NA | 0.41 |
| 39 | ANKRD11 | 87861536 | 88084470 | 11 | 0 | 61 | 246990 | −72136 | −72136 | 1 | 0.47 | 0.85 | NA |
| 40 | NRXN1 | 49999148 | 51113178 | 155 | 0 | NA | 28619013 | NA | 28619013 | 1 | NA | NA | 0.59 |
| 41 | ADCY8 | 131861736 | 132123854 | 0 | 1 | 45 | 861663 | −378337 | −378337 | 1 | 0.52 | 1.97 | NA |
| 42 | TRDN | 123579182 | 123999937 | 96 | 0 | NA | 20654629 | −5440605 | −5440605 | 1 | NA | NA | 0.48 |
| 43 | STAU2 | 74495160 | 74821629 | 1 | 0 | NA | 199555 | −119303 | −119303 | 1 | 1.43 | NA | NA |
| 44 | SF1 | 64288654 | 64302817 | 1 | 1 | 9 | 24747 | −560058 | 24747 | 1 | NA | NA | 0.23 |
| 45 | CLIP2 | 73341739 | 73458196 | 15 | 1 | NA | 1543149 | −35065 | −35065 | 1 | NA | NA | 0.52 |
| 46 | CLDN3 | 72821263 | 72822536 | 5 | 0 | NA | 404089 | −49338 | −49338 | 1 | NA | NA | 0.29 |

| | | | | | | | | | | |
|---|---|---|---|---|---|---|---|---|---|---|
| 47 | ZSWIM4 | 13767274 | 13804044 | 1 | 1 | NA | NA | 50124 | NA | NA | 0.38 |
| 48 | GLRB | 158216788 | 158312299 | 0 | 1 | 3 | 48887 | 48887 | NA | NA | 0.31 |
| 49 | DCHS2 | 155375138 | 155632318 | 14 | 0 | NA | 2584470 | 2584470 | NA | NA | 0.37 |
| 50 | TRPS1 | 116489900 | 116750429 | 20 | 1 | 43 | -60460408 | -60460408 | NA | NA | NA |
| 51 | MDGA2 | 46379045 | 47213703 | NA | NA | NA | -1971482 | -1971482 | 0.42 | 0.33 | 0.39 |
| 52 | CNBD1 | 87947840 | 88435220 | 1 | 1 | 38 | NA | NA | NA | NA | NA |
| 53 | STAG3 | 99613474 | 99659778 | 2 | 0 | NA | 683360 | -122823 | 0.91 | 0.91 | NA |
| 54 | GATA4 | 11599162 | 11654918 | 0 | 1 | 18 | -23787222 | 111895 | NA | NA | 0.21 |
| 55 | VPS13B | 100094670 | 100958983 | 1 | 0 | NA | 9709 | 9709 | NA | NA | NA |
| 56 | DOCK5 | 25098204 | 25326536 | 2 | 0 | NA | 83469 | 83469 | 0.57 | NA | NA |
| 57 | ZHX2 | 123863082 | 124055936 | 9 | 0 | NA | -187596 | 14747 | 0.98 | NA | NA |
| 58 | ARHGEF5 | 143683366 | 143708657 | NA | 0 | NA | -1478148 | 706280 | 1.97 | 0.29 | NA |
| 59 | SDC2 | 97575058 | 97693213 | 1 | 1 | 39 | -7112653 | -13747479 | NA | NA | 0.35 |
| 60 | MYLK | 124811586 | 125085868 | 2 | 0 | NA | NA | -159108 | 0.68 | NA | NA |
| 61 | LPHN3 | 62045434 | 62207622 | 157 | 0 | NA | 1032370 | 210407 | NA | 0.38 | 0.24 |
| 62 | MOSPD3 | 100047661 | 100050932 | 0 | 1 | 12 | 210407 | 30824069 | NA | NA | 0.17 |
| 63 | GYS2 | 21580390 | 21649048 | NA | NA | NA | 30824069 | -3929 | NA | NA | 0.36 |
| 64 | GAS8 | 88616509 | 88638880 | NA | NA | NA | 5043 | NA | NA | NA | NA |
| 65 | RAB9A | 13617262 | 13637681 | 191 | 0 | NA | NA | -21813 | 0.42 | NA | NA |
| 66 | POLR3D | 22158564 | 22164624 | 1 | 1 | 25 | -21813 | 35134932 | 0.85 | NA | NA |
| 67 | PSD3 | 18429093 | 18915476 | 0 | 0 | 23 | 35134932 | -12768 | 0.33 | NA | NA |
| 68 | ZFPM2 | 106400323 | 106885939 | 2 | 1 | 41 | -12768 | -126090 | NA | NA | 0.35 |
| 69 | ATP6V1C1 | 104102424 | 104154461 | 5 | 0 | NA | 300007 | -729979 | 2.58 | NA | NA |
| 70 | MEF2C | 88051922 | 88214780 | 63 | 0 | NA | 1444960 | 427830 | 1.16 | 0.21 | 0.24 |
| 71 | PKIA | 79590891 | 79678040 | 2 | 1 | 31 | -608753 | -19278276 | NA | NA | 0.15 |
| 72 | ADAMTS18 | 75873527 | 76026512 | 0 | 0 | NA | -19278276 | 1007876 | NA | NA | NA |
| 73 | STYXL1 | 75463592 | 75515257 | 0 | 1 | 52 | -1648815 | 287400 | 0.63 | 0.42 | NA |
| 74 | EPM2A | 145988141 | 146098684 | 7 | 0 | NA | -722891 | 72 | 0.74 | 0.85 | 0.17 |
| 75 | LEPREL1 | 191157213 | 191321407 | 2 | 1 | 2 | -1679 | 291927 | NA | NA | 0.20 |
| 76 | GABRA2 | 45946341 | 46086561 | NA | 0 | NA | -772282 | -49278 | NA | NA | NA |
| 77 | RCOR2 | 63435303 | 63440892 | NA | 0 | NA | -49278 | -1800760 | 0.29 | NA | 0.16 |
| 78 | MFHAS1 | 8679409 | 8788541 | 3 | 1 | 15 | -1800760 | 81715 | NA | NA | 0.00 |
| 79 | SCARA5 | 27783672 | 27906117 | 0 | 0 | NA | -5420413 | 109315 | 0.63 | NA | NA |
| 80 | CCDC25 | 27646756 | 27686089 | 0 | 0 | 31 | NA | 29490 | 0.63 | NA | 0.14 |
| 81 | FAM38A | 87302916 | 87330317 | 2 | 1 | NA | -97583 | 97583 | 1.29 | NA | 0.19 |
| 82 | CTSB | 11737442 | 11763055 | 7 | 0 | 59 | -188353 | -2604 | NA | 0.02 | NA |
| 83 | PTK2 | 141737683 | 142080514 | NA | 1 | NA | -2604 | -55179 | NA | NA | 0.14 |
| 84 | SPIRE2 | 88422408 | 88465228 | 0 | 0 | 57 | -55179 | -5943220 | 0.38 | 0.33 | NA |
| 85 | C13orf23 | 38482003 | 38510252 | 21 | 1 | 62 | 1084499 | 2292 | NA | 0.17 | NA |
| 86 | BOD1L | 13179464 | 13238426 | 76 | 0 | NA | NA | 4175452 | NA | 0.00 | NA |
| 87 | FAM160B2 | 22002660 | 22017835 | 0 | 1 | NA | -11842 | 30632257 | NA | NA | 0.15 |
| 88 | NUS1 | 118103310 | 118138577 | 15 | 1 | 24 | 4175452 | 2493 | 0.25 | 0.29 | NA |
| 89 | MTHFSD | 85121284 | 85157509 | 5 | 1 | NA | 30632257 | 5440605 | NA | NA | 0.14 |
| 90 | UBR5 | 103334748 | 103493671 | 3 | 0 | 57 | 2493 | -15714 | NA | 0.21 | 0.19 |
| 91 | GALNS | 87407644 | 87450885 | 0 | 1 | 60 | 5440605 | -128437 | NA | 0.14 | NA |
| 92 | FSTL5 | 162524501 | 163304636 | NA | 0 | NA | 1036491 | -4478 | NA | 0.17 | 0.14 |
| 93 | SIM1 | 100939606 | 101019494 | 0 | 1 | 6 | 608753 | -4017824 | NA | NA | NA |
| 94 | TG | 133948387 | 134216325 | 0 | 0 | 46 | 122 | 43297 | NA | NA | 0.15 |
| 95 | BFSP2 | 134601480 | 134676746 | 58 | 0 | NA | -4017824 | -18153 | 0.91 | 0.21 | 0.13 |
| 96 | MMP16 | 89118580 | 89408833 | 9 | 1 | NA | -1437036 | -8678754 | NA | NA | NA |
| 97 | RIMS2 | 104582291 | 105333263 | 1 | 0 | NA | -18153 | -683360 | NA | 0.74 | NA |
| 98 | PDS5B | 32058564 | 32250157 | 21 | 0 | NA | -8678754 | 127566 | 0.07 | 1.04 | NA |
| 99 | CDK7 | 68566471 | 68609004 | 0 | 1 | 4 | 9790009 | 6231846 | NA | NA | 0.08 |
| | | | | | | | 2921859 | 3274 | NA | 0.33 | NA |
| | | | | | | | 127566 | | | | |
| | | | | | | | 6231846 | | | | |
| | | | | | | | NA | | | | |
| | | | | | | | 11239 | | | | |

| | | | | | | | | | | |
|---|---|---|---|---|---|---|---|---|---|---|
| 100 | CNTNAP4 | 74868677 | 75150636 | 1 | 0 | NA | 722891 | -843789 | 722891 | 0.57 | NA | NA |
| 101 | CFDP1 | 73885109 | 74024888 | 7 | 1 | 51 | 843789 | -25657 | -25657 | 0.47 | NA | NA |
| 102 | FBXL4 | 99428055 | 99502570 | 7 | 0 | NA | 1437036 | -5242062 | 1437036 | NA | NA | 0.01 |
| 103 | RFX1 | 13933353 | 13978097 | NA | 0 | NA | NA | -30662 | -30662 | NA | NA | 0.13 |
| 104 | NALCN | 100504131 | 100866814 | 42 | 0 | NA | 12242043 | -8187438 | -8187438 | NA | NA | 0.13 |
| 105 | STX1A | 72751472 | 72771925 | 1 | 0 | NA | 49338 | NA | 49338 | NA | NA | 0.13 |
| 106 | CYP7B1 | 65671246 | 65873902 | 21 | 0 | NA | 2623061 | -5476925 | 2623061 | NA | NA | NA |
| 107 | ARHGEF10 | 1759549 | 1894206 | 1 | 1 | NA | NA | -115501 | 86359 | NA | NA | NA |
| 108 | ENTPD4 | 23299386 | 23371081 | 0 | 1 | 28 | 71227 | 18281 | 18281 | 0.33 | 0.00 | 0.09 |
| 109 | ZNF704 | 81713324 | 81949571 | 0 | 0 | 37 | 93034 | -870671 | 93034 | NA | 0.42 | NA |
| 110 | C8orf79 | 12847554 | 12931653 | 0 | 1 | 19 | 53590 | -1084499 | 53590 | 0.42 | 0.25 | NA |
| 111 | SLC9A9 | 144466755 | 145049979 | 50 | 0 | NA | 12271116 | -9790009 | -9790009 | NA | 0.33 | 0.23 |
| 112 | CHMP7 | 23157095 | 23175450 | 1 | 1 | 27 | 34647 | -18511 | -18511 | NA | 0.21 | NA |
| 113 | GPC5 | 90848919 | 92316693 | 29 | 0 | NA | 8187438 | -19509588 | 8187438 | 1.16 | NA | 0.11 |
| 114 | MYC | 128816862 | 128822853 | 0 | 0 | 44 | 206193 | -318241 | 206193 | NA | NA | NA |
| 115 | STIP1 | 63709873 | 63728596 | 20 | 0 | NA | 560058 | -19764 | -19764 | NA | NA | 0.01 |
| 116 | ZBTB20 | 115540230 | 116348817 | 51 | 0 | NA | 8462769 | -8761797 | 8462769 | NA | 0.02 | NA |
| 117 | MEN1 | 64327564 | 64335342 | 0 | 1 | 47 | 12898 | -24747 | 12898 | NA | NA | 0.09 |
| 118 | SLC26A7 | 92330692 | 92479554 | 5 | 0 | NA | 2729012 | -2921859 | 2729012 | NA | 0.14 | NA |
| 119 | ALCAM | 106568403 | 106778433 | 49 | 0 | NA | 8761797 | NA | 8761797 | NA | NA | NA |
| 120 | KIF13B | 28980715 | 29176529 | NA | 1 | 32 | NA | -14009 | -14009 | 0.33 | 0.21 | 0.23 |
| 121 | MBTPS1 | 82644872 | 82708018 | 0 | 1 | 54 | 5371 | -50994 | 5371 | 0.33 | NA | NA |
| 122 | PPP2R5B | 64448756 | 64458523 | NA | 0 | NA | NA | -80139 | -80139 | NA | NA | 0.02 |
| 123 | VPS13C | 59931884 | 60139939 | NA | 0 | NA | NA | -2474214 | -2474214 | NA | NA | 0.02 |
| 124 | ASPSCR1 | 77528715 | 77568569 | 6 | 0 | 65 | 40474 | -16362 | -16362 | 0.80 | 0.05 | 0.01 |
| 125 | EPO | 100156359 | 100159257 | 146 | 1 | NA | 29534682 | -31553 | -31553 | 0.38 | 0.21 | 0.07 |
| 126 | HEY1 | 80838801 | 80842653 | 3 | 0 | 36 | 870671 | -97933 | -97933 | NA | NA | NA |
| 127 | KALRN | 125296275 | 125922726 | 76 | 1 | NA | 8678754 | -210407 | -210407 | 0.47 | NA | 0.04 |
| 128 | RGS22 | 101042452 | 101187520 | 7 | 0 | NA | 812460 | -83469 | -83469 | NA | 0.21 | NA |
| 129 | WDR7 | 52469614 | 52848040 | 45 | 0 | NA | 12833135 | -3157834 | -3157834 | 0.33 | NA | 0.03 |
| 130 | COL11A1 | 103114611 | 103346640 | NA | 0 | NA | NA | -4955408 | -4955408 | NA | NA | 0.03 |
| 131 | GHDC | 37594632 | 37599722 | 482 | 0 | NA | 39903967 | -7810 | -7810 | NA | NA | NA |
| 132 | ATP2C2 | 82959634 | 83055293 | 0 | 1 | 55 | 13315 | -38746 | 13315 | NA | 0.29 | 0.07 |
| 133 | CDH17 | 95208566 | 95289986 | 14 | 0 | NA | 2053354 | -2729012 | 2053354 | NA | NA | 0.04 |
| 134 | DGKG | 187347686 | 187562717 | 23 | 0 | NA | 3269193 | -17000632 | 3269193 | NA | NA | 0.01 |
| 135 | GRK5 | 120957091 | 121205118 | NA | NA | NA | NA | NA | NA | NA | 0.05 | NA |
| 136 | GRM1 | 146390611 | 146800427 | 83 | 0 | NA | 18812721 | -291927 | -291927 | NA | 0.21 | NA |
| 137 | IMPA1 | 82732751 | 82761115 | 4 | 0 | NA | 2842997 | -545893 | -545893 | NA | 0.05 | 0.04 |
| 138 | RPL7 | 74365073 | 74375857 | 1 | 0 | NA | 119303 | -352193 | 119303 | 0.17 | NA | NA |
| 139 | COL21A1 | 56029347 | 56366851 | NA | NA | NA | NA | NA | NA | NA | NA | 0.03 |
| 140 | COL12A1 | 75850762 | 75972343 | 18 | 0 | NA | 7686493 | -4871884 | -4871884 | 0.21 | 0.21 | 0.03 |
| 141 | MLYCD | 82490231 | 82507286 | 1 | 1 | NA | 52452 | -102526 | 52452 | NA | NA | NA |
| 142 | AR | 66680599 | 66860844 | 0 | 1 | 69 | 318596 | -904991 | 318596 | 0.17 | 0.29 | 0.05 |
| 143 | PLCB1 | 8061296 | 8813547 | NA | NA | NA | NA | NA | NA | NA | NA | NA |
| 144 | ACTL8 | 17954395 | 18026145 | 662 | 1 | 1 | 79289745 | -57439 | -57439 | NA | 0.05 | 0.05 |
| 145 | TFDP1 | 113287057 | 113343500 | NA | NA | NA | NA | -12420243 | -12420243 | NA | 0.17 | NA |
| 146 | IQCE | 2565158 | 2620893 | 13 | 0 | NA | 2861062 | NA | 2861062 | NA | NA | 0.03 |
| 147 | SMARCB1 | 22459150 | 22506703 | 290 | 0 | NA | 23030490 | NA | 23030490 | NA | 0.02 | NA |
| 148 | MTDH | 98725583 | 98807711 | 7 | 0 | NA | 465852 | -1032370 | 465852 | NA | 0.05 | NA |
| 149 | NECAB2 | 82559738 | 82593878 | 1 | 1 | NA | 50994 | -52452 | 50994 | NA | 0.05 | NA |
| 150 | DEF8 | 88542684 | 88561968 | 0 | 1 | 63 | 4521 | -12678 | 4521 | 0.17 | 0.07 | NA |
| 151 | RNF40 | 30681100 | 30695129 | NA | 0 | NA | NA | -392513 | -392513 | NA | 0.05 | 0.09 |
| 152 | TICAM2 | 114942247 | 114989610 | NA | 0 | NA | NA | -26727467 | -26727467 | NA | NA | 0.03 |

-continued

| | | | | | | | | | | |
|---|---|---|---|---|---|---|---|---|---|---|
| 153 | GLG1 | 73043357 | 73198518 | 3 | 0 | NA | 266457 | 266457 | 1 | 0.10 | NA | NA |
| 154 | MECOM | 170283981 | 170347054 | 89 | 0 | NA | 17000632 | -1403582 | -8012470 | 1 | NA | 0.07 | NA |
| 155 | TCEB1 | 75021184 | 75046959 | 2 | 0 | NA | 262534 | -199555 | -199555 | 1 | 0.02 | NA | NA |
| 156 | CTNNA2 | 79732191 | 80729415 | NA | 0 | NA | NA | -28619013 | -28619013 | 1 | 0.02 | NA | 0.03 |
| 157 | NIPAL2 | 99273563 | 99375797 | 1 | 0 | NA | 160240 | -465852 | 160240 | 1 | 0.05 | NA | NA |
| 158 | CDCA2 | 25372428 | 25421353 | 0 | 1 | 29 | 336689 | -591 | -591 | 1 | 0.07 | NA | NA |
| 159 | WWP2 | 68353710 | 68533145 | 5 | 0 | NA | 405177 | -57656 | -57656 | 1 | 0.02 | NA | NA |
| 160 | DDX19A | 68938322 | 68964780 | 0 | 1 | 50 | 6059 | 405177 | 6059 | 1 | 0.17 | NA | NA |
| 161 | STK3 | 99536037 | 99907074 | 1 | 0 | NA | 187596 | -160240 | -160240 | 1 | 0.02 | NA | NA |
| 162 | DNAH2 | 7562746 | 7677783 | NA | NA | NA | NA | NA | NA | 1 | 0.02 | NA | NA |
| 163 | NFAT5 | 68156498 | 68296054 | 2 | 0 | NA | 57656 | -7528258 | 57656 | 1 | 0.17 | NA | NA |
| 164 | CNGB1 | 56475004 | 56562513 | 3 | 0 | NA | 142487 | NA | 142487 | 1 | 0.02 | NA | NA |
| 165 | UBE2CBP | 83658836 | 83832269 | 3 | 0 | NA | 144558 | -7686493 | 144558 | 1 | 0.38 | NA | NA |
| 166 | C8orf16 | 11021390 | 11025155 | 0 | 1 | 17 | 154255 | -697587 | 154255 | 1 | 0.14 | NA | NA |
| 167 | KIAA0196 | 126105691 | 126173191 | 3 | 0 | NA | 2323848 | -1286863 | -1286863 | 1 | 0.29 | NA | 0.21 |
| 168 | CLCNKB | 16242834 | 16256390 | 29 | 0 | NA | 1482527 | 1482527 | 1482527 | 1 | NA | NA | 0.04 |
| 169 | C16orf80 | 56705000 | 56720797 | 10 | 0 | NA | 3524069 | -142487 | -142487 | 1 | 0.14 | NA | 0.03 |
| 170 | ZFHX3 | 71374285 | 71639775 | 2 | 0 | NA | 1403582 | -2343793 | 1403582 | 1 | 0.14 | NA | NA |
| 171 | PPM1L | 161956791 | 162271511 | 13 | 0 | NA | 8012470 | -4217170 | -4217170 | 1 | NA | NA | 0.11 |
| 172 | NKIRAS2 | 37422564 | 37431180 | 1 | 0 | NA | 75799 | NA | 75799 | 1 | 0.02 | NA | 0.06 |
| 173 | RSPO2 | 108980721 | 109165052 | 9 | 0 | NA | 4139285 | -401262 | -401262 | 1 | 0.17 | NA | NA |
| 174 | XPO7 | 21833126 | 21920041 | 3 | 1 | 42 | 82619 | -1627372 | 82619 | 1 | 0.25 | NA | 0.47 |
| 175 | ME1 | 83976827 | 84197498 | 41 | 0 | NA | 7084576 | -144558 | -144558 | 1 | NA | NA | 0.33 |
| 176 | NLGN4Y | 15144026 | 15466924 | NA | NA | NA | NA | NA | NA | 1 | 0.07 | NA | NA |
| 177 | LZTS1 | 20147956 | 20205754 | 2 | 0 | NA | 1627372 | -850362 | -850362 | 1 | NA | NA | NA |
| 178 | FBXL18 | 5481955 | 5523646 | NA | 0 | NA | NA | -2861062 | -2861062 | 1 | 0.07 | NA | NA |
| 179 | TBC1D10B | 30275925 | 30288587 | 14 | 0 | NA | 392513 | 392513 | 392513 | 1 | NA | NA | NA |
| 180 | WDR59 | 73464975 | 73576518 | 5 | 0 | NA | 243911 | NA | 243911 | 1 | 0.10 | NA | NA |
| 181 | BLK | 11388930 | 11459516 | 1 | 0 | NA | 139646 | -165868 | 139646 | 1 | 0.10 | NA | NA |
| 182 | MEPCE | 99865190 | 99869676 | 2 | 0 | NA | 32404 | -29540 | -29540 | 1 | NA | NA | NA |
| 183 | DLGAP2 | 1436939 | 1644048 | 1 | 0 | NA | 115501 | 115501 | 115501 | 1 | NA | NA | NA |
| 184 | ZFAT | 135594215 | 135794463 | 8 | 0 | NA | 5943220 | NA | -1248464 | 1 | 0.25 | 0.14 | NA |
| 185 | FASN | 77629504 | 77649395 | NA | 1 | 66 | NA | -1248464 | -262 | 1 | NA | NA | 0.47 |
| 186 | GIGYF1 | 100115066 | 100124806 | 1 | 0 | NA | 31553 | -262 | -23059 | 1 | NA | NA | 0.33 |
| 187 | ANXA13 | 124762216 | 124818828 | 11 | 0 | NA | 1286863 | -23059 | -706280 | 0 | 0.10 | NA | NA |
| 188 | CDYL2 | 79195176 | 79395680 | 3 | 0 | NA | 248923 | -706280 | 248923 | 0 | 0.25 | NA | NA |
| 189 | TOX | 59880531 | 60194321 | 10 | 0 | NA | 5476925 | -1391644 | 5476925 | 0 | 1.23 | NA | NA |
| 190 | NKX2-6 | 23615909 | 23620056 | 6 | 0 | NA | 1478148 | NA | -129901 | 0 | 0.21 | 0.80 | NA |
| 191 | RAIYL | 85604112 | 85963979 | 12 | 0 | NA | 1691298 | -129901 | 1691298 | 0 | 0.38 | 0.91 | 0.76 |
| 192 | TBC1D22A | 45537193 | 45948399 | NA | 0 | NA | NA | -2842997 | -23030490 | 1 | NA | 1.43 | 4.22 |
| 193 | TFE3 | 48772613 | 48787722 | NA | 0 | NA | NA | -23030490 | -35134932 | 1 | NA | 0.10 | NA |
| 194 | KCNAB1 | 157321095 | 157739621 | 22 | 1 | 66 | 4217170 | -35134932 | 4217170 | 1 | 2.24 | 0.10 | 0.37 |
| 195 | SULF1 | 70541427 | 70735701 | 0 | 1 | 33 | 11428 | -12271116 | 11428 | 0 | 1.83 | 2.24 | NA |
| 196 | RAB5C | 37530524 | 37560548 | 0 | 1 | 64 | 1891 | -647617 | -1627 | 0 | NA | 0.68 | NA |
| 197 | DHX58 | 37506979 | 37518277 | 0 | 1 | 64 | 380 | -1627 | -1627 | 0 | NA | NA | NA |
| 198 | ASAP1 | 131133535 | 131483399 | 0 | 1 | 45 | 378337 | -75799 | 378337 | 1 | NA | 0.80 | NA |
| 199 | CA5A | 86479126 | 86527613 | 6 | 1 | 58 | 14926 | -2104073 | 14926 | 1 | 0.29 | 0.91 | NA |
| 200 | C6orf118 | 165613448 | 165643101 | 12 | 0 | NA | 17665 | -18511 | -18511 | 0 | NA | NA | 0.53 |
| 201 | NCOA2 | 71178380 | 71478574 | NA | 1 | 33 | 233471 | -18811272 | 17665 | 0 | NA | 0.21 | NA |
| 202 | PKD1L2 | 79691985 | 79811477 | NA | 1 | 53 | 18320 | -32264 | -32264 | 0 | 0.57 | 0.21 | NA |
| 203 | BANP | 86542539 | 86668425 | 0 | 1 | 58 | 378801 | -4504 | -4504 | 0 | 1.63 | 0.07 | NA |
| 204 | KIAA1967 | 22518202 | 22533920 | 0 | 1 | 26 | -14 | -597 | -14926 | 0 | 0.29 | 0.63 | NA |
| 205 | COPG2 | 129933404 | 129935887 | 106 | 1 | 13 | 13747479 | -41 | -41 | 0 | 0.38 | 0.52 | NA |

-continued

| | | | | | | | | | | | | |
|---|---|---|---|---|---|---|---|---|---|---|---|---|
| 206 | ZNF706 | 102278444 | 102278136 | 0 | 1 | 40 | 287026 | −243699 | 0 | NA | NA | NA |
| 207 | GAN | 79906076 | 79971441 | 0 | 1 | 53 | 398967 | −23828 | 0 | 0.33 | 0.21 | NA |
| 208 | PLCG2 | 80370408 | 80549399 | 0 | 1 | 53 | 76965 | −398967 | 0 | 0.42 | 0.33 | NA |
| 209 | C19orf57 | 13854168 | 13877909 | 0 | 1 | 68 | 105 | 76965 | 0 | 0.68 | 0.33 | 0.37 |
| 210 | PDGFRL | 17478443 | 17545655 | 0 | 1 | 21 | −71 | −50124 | 0 | NA | NA | NA |
| 211 | ESD | 46243393 | 46269368 | 0 | 1 | 48 | 36146 | −6086 | 0 | 1.56 | NA | 0.28 |
| 212 | CPA5 | 129771892 | 129795807 | 0 | 1 | 13 | 11661 | −20607 | 0 | NA | NA | 0.36 |
| 213 | BIN3 | 22533906 | 22582553 | 1 | 1 | 26 | 18566 | −20643 | 0 | 0.00 | 0.38 | NA |
| 214 | ZFHX4 | 77756078 | 77942076 | 0 | 1 | 35 | 1648815 | 14 | 0 | 1.23 | NA | NA |
| 215 | CPA6 | 68496963 | 68821134 | 0 | 1 | 33 | 205773 | −1114478 | 0 | 0.91 | NA | NA |
| 216 | EYA1 | 72272222 | 72437021 | 0 | 1 | 34 | 479311 | −2623061 | 0 | 0.68 | NA | NA |
| 217 | CHRNA2 | 27373196 | 27392730 | 0 | 1 | 30 | 11832 | −463009 | 0 | 0.74 | NA | NA |
| 218 | TNKS | 9450855 | 9677266 | 0 | 1 | 16 | 271923 | −376 | 0 | 1.04 | NA | NA |
| 219 | HNF4G | 76482732 | 76641600 | 0 | 1 | 35 | 1114478 | −522716 | 0 | 1.10 | NA | 0.20 |
| 220 | LRCH1 | 46025304 | 46222786 | 0 | 1 | 48 | 20607 | −373386 | 0 | NA | NA | NA |
| 221 | ADRA1A | 26661584 | 26778839 | 0 | 1 | 30 | 370899 | −2766260 | 0 | 0.98 | NA | NA |
| 222 | EPHX2 | 27404562 | 27458403 | 2 | 1 | 30 | 188353 | −89977 | 0 | 0.63 | NA | NA |
| 223 | SORBS3 | 22465196 | 22488952 | 0 | 1 | 26 | 3247 | −11832 | 0 | NA | 0.47 | 0.17 |
| 224 | GRIA2 | 158361186 | 158506677 | 9 | 1 | 3 | 4017824 | −10616 | 0 | NA | NA | NA |
| 225 | PDLIM2 | 22492199 | 22511483 | 0 | 1 | 26 | 1584 | −3247 | 0 | NA | 0.42 | NA |
| 226 | MTMR7 | 17199923 | 17315207 | 0 | 1 | 21 | 83768 | −48887 | 0 | 0.85 | NA | NA |
| 227 | FBXO24 | 100021892 | 100036674 | 0 | 1 | 12 | 1144 | −3247 | 0 | NA | NA | 0.24 |
| 228 | CRISPLD1 | 76059531 | 76109346 | 0 | 1 | 35 | 373386 | −1533557 | 0 | NA | NA | NA |
| 229 | DPYS | 105460829 | 105548453 | 0 | 1 | 41 | 22190 | −180 | 0 | 1.63 | 0.21 | NA |
| 230 | DTNA | 30327279 | 30725806 | 62 | 1 | 67 | 17395350 | −129712 | 0 | 0.57 | NA | 0.15 |
| 231 | KLHDC4 | 86298920 | 86357056 | 0 | 1 | 58 | 64075 | −127566 | 0 | NA | NA | NA |
| 232 | CYBA | 87237199 | 87244958 | 0 | 1 | 58 | 891 | −269766 | 0 | NA | 0.25 | NA |
| 233 | JPH3 | 86194000 | 86289263 | 0 | 1 | 58 | 9657 | −9657 | 0 | 0.21 | 0.42 | NA |
| 234 | TMEM120A | 75454238 | 75461913 | 1 | 1 | 10 | 1679 | −2814 | 0 | NA | 0.21 | 0.00 |
| 235 | MTUS1 | 17545584 | 17702666 | 0 | 1 | 21 | 121980 | −1036491 | 0 | 0.80 | NA | NA |
| 236 | C8orf34 | 69405511 | 69893810 | 0 | 1 | 33 | 647617 | −248023 | 0 | 2.37 | NA | 0.11 |
| 237 | GRHL2 | 102541162 | 102750995 | 0 | 1 | 40 | 16952 | 71 | 0 | NA | 0.21 | NA |
| 238 | CPA2 | 129693939 | 129716870 | 0 | 1 | 13 | 3360 | −99060 | 0 | NA | NA | NA |
| 239 | NAT2 | 18293035 | 18303003 | 0 | 1 | 23 | 126090 | −287026 | 0 | 0.63 | NA | NA |
| 240 | DPYSL2 | 26491327 | 26571607 | 0 | 1 | 30 | 89977 | 3360 | 0 | 0.63 | NA | NA |
| 241 | ZDHHC7 | 83565573 | 83602642 | 0 | 1 | 56 | 16269 | 126090 | 0 | NA | 0.25 | NA |
| 242 | ELP3 | 27999759 | 28104584 | 6 | 1 | 31 | 699246 | −306248 | 0 | 0.68 | NA | NA |
| 243 | RHOBTB2 | 22913059 | 22933655 | 2 | 1 | 26 | 115396 | −533035 | 0 | NA | NA | NA |
| 244 | NEIL2 | 11664627 | 11682263 | 1 | 1 | 18 | 55179 | −64959 | 0 | 0.33 | 0.00 | NA |
| 245 | HR | 22027877 | 22045326 | 0 | 1 | 24 | 6152 | −2452 | 0 | NA | 0.33 | NA |
| 246 | EFR3A | 132985517 | 133095071 | 0 | 1 | 45 | 10596 | −306299 | 0 | 0.52 | NA | NA |
| 247 | STMN4 | 27149738 | 27171843 | 0 | 1 | 30 | 26478 | −9709 | 0 | 0.63 | 0.33 | NA |
| 248 | PRDM14 | 71126574 | 71146116 | 0 | 1 | 33 | 32264 | −4474 | 0 | 1.49 | NA | NA |
| 249 | MARVELD2 | 68746699 | 68773646 | 82 | 1 | 4 | 19278276 | −861663 | 0 | NA | 0.47 | NA |
| 250 | SLC39A14 | 22280737 | 22347462 | 0 | 1 | 26 | 7079 | −370899 | 0 | 0.02 | 0.14 | NA |
| 251 | ACTL6B | 100078678 | 100092007 | 1 | 1 | 12 | 23059 | −216812 | 0 | NA | NA | 0.01 |
| 252 | TUSC3 | 15442101 | 15666366 | 6 | 1 | 20 | 1533557 | −315 | 0 | 0.52 | NA | NA |
| 253 | COX4NB | 84369737 | 84390601 | 0 | 1 | 57 | 96 | −116113 | 0 | NA | 0.33 | NA |
| 254 | XKR9 | 71755848 | 71809213 | 0 | 1 | 34 | 463009 | −1569 | 0 | 0.33 | 0.25 | NA |
| 255 | C16orf46 | 79644603 | 79668373 | 0 | 1 | 53 | 5057 | −301882 | 0 | NA | 0.14 | 0.14 |
| 256 | TAF9 | 68696327 | 68701596 | 1 | 1 | 4 | −716 | −27547 | 0 | 1.49 | NA | NA |
| 257 | KCNQ3 | 133210438 | 133561961 | 1 | 1 | 45 | 217672 | −43354 | 0 | 2.37 | 0.29 | NA |
| 258 | UTRN | 144654566 | 145215859 | 0 | 1 | 7 | 772282 | −20654629 | 0 | NA | NA | 0.18 |

-continued

| # | Gene | | | | | | | | |
|---|---|---|---|---|---|---|---|---|---|
| 259 | RAD17 | 68700880 | 68746384 | 0 | 1 | 4 | 315 | 716 | 315 | 0 | NA | NA | NA |
| 260 | ZFPM1 | 87047226 | 87128890 | 0 | 1 | 58 | 18723 | -378801 | 18723 | 0 | NA | 0.25 | NA |
| 261 | PTDSS1 | 97343340 | 97415950 | 0 | 1 | 39 | 159108 | -2053354 | 159108 | 0 | 0.25 | 0.25 | NA |
| 262 | IRF8 | 84490275 | 84513710 | 0 | 1 | 57 | 587924 | -92166 | -92166 | 0 | NA | NA | NA |
| 263 | YWHAZ | 101999980 | 102034745 | 0 | 1 | 40 | 243699 | -812460 | 243699 | 0 | 0.29 | 0.14 | NA |
| 264 | MRPS36 | 68549329 | 68577710 | 0 | 1 | 4 | -11239 | -7390 | -7390 | 0 | 0.29 | 0.29 | NA |
| 265 | LACTB2 | 71712045 | 71743946 | 0 | 1 | 34 | 11902 | -233471 | 11902 | 0 | NA | NA | NA |
| 266 | SNAI3 | 87271591 | 87280383 | 0 | 1 | 58 | 10028 | -14572 | 10028 | 0 | 0.21 | NA | NA |
| 267 | TMEM71 | 133779633 | 133842010 | 0 | 1 | 46 | 14776 | -217672 | 14776 | 0 | 0.42 | NA | NA |
| 268 | PREX2 | 69026907 | 69306451 | 0 | 1 | 33 | 99060 | -205773 | 99060 | 0 | 3.36 | 0.21 | NA |
| 269 | CPA1 | 129807468 | 129815165 | 0 | 1 | 13 | 8446 | -11661 | 8446 | 0 | NA | NA | 0.09 |
| 270 | PHF20L1 | 133856786 | 133930234 | 0 | 1 | 46 | 18153 | -14776 | 14776 | 0 | 0.38 | 0.10 | NA |
| 271 | KIAA0513 | 83618911 | 83685327 | 0 | 1 | 56 | 517197 | -16269 | -16269 | 0 | NA | NA | NA |
| 272 | PI15 | 75899327 | 75929819 | 0 | 1 | 35 | 129712 | -457439 | 129712 | 0 | 0.47 | 0.07 | 0.06 |
| 273 | PCM1 | 17824646 | 17935562 | 2 | 1 | 22 | 22652 | -121980 | 22652 | 0 | 0.00 | NA | NA |
| 274 | SH2D4A | 19215483 | 19297594 | 0 | 1 | 23 | 850362 | -300007 | -300007 | 0 | 0.42 | NA | NA |
| 275 | C16orf74 | 84298624 | 84342190 | 5 | 1 | 57 | 27547 | -18535 | -18535 | 0 | 0.25 | 0.17 | NA |
| 276 | TP63 | 190831910 | 191107935 | 0 | 1 | 2 | 49278 | -3269193 | 49278 | 0 | NA | 0.47 | 0.04 |
| 277 | DACH1 | 70910099 | 71339331 | 28 | 1 | 49 | 19509588 | -1329507 | -1329507 | 0 | NA | NA | NA |
| 278 | TNFRSF10A | 23104916 | 23138584 | 0 | 1 | 27 | 18511 | -27431 | 18511 | 0 | NA | 0.14 | NA |
| 279 | MDH2 | 75515329 | 75533864 | 2 | 1 | 10 | 260189 | -72 | -72 | 0 | 0.38 | NA | 0.06 |
| 280 | PAG1 | 82042605 | 82186858 | 8 | 1 | 37 | 545893 | -93034 | -93034 | 0 | NA | 0.07 | NA |
| 281 | SLC25A37 | 23442308 | 23486008 | 1 | 1 | 28 | 129901 | -71227 | -71227 | 0 | 0.29 | NA | NA |
| 282 | BCAR1 | 73820429 | 73859452 | 0 | 1 | 51 | 25657 | -243911 | 25657 | 0 | 0.25 | NA | NA |
| 283 | COX4I1 | 84390697 | 84398109 | 0 | 1 | 57 | 92166 | -96 | -96 | 0 | NA | 0.29 | NA |
| 284 | EIF4H | 73226625 | 73249358 | 0 | 1 | 9 | 12304 | -404089 | 12304 | 0 | NA | NA | 0.07 |
| 285 | ZC3H18 | 87164343 | 87225756 | 0 | 1 | 58 | 6746 | -294 | -294 | 0 | 0.17 | 0.10 | NA |
| 286 | STMN2 | 80685916 | 80740868 | 0 | 1 | 36 | 97933 | -1007876 | 97933 | 0 | 0.38 | NA | NA |
| 287 | AFG3L1 | 88566489 | 88594696 | 1 | 1 | 63 | 21813 | -4521 | -4521 | 0 | NA | 0.17 | NA |
| 288 | HSD17B2 | 80626364 | 80689638 | 1 | 1 | 53 | 750123 | -76965 | -76965 | 0 | 0.29 | NA | NA |
| 289 | MVD | 87245849 | 87257019 | 0 | 1 | 58 | 14572 | -891 | -891 | 0 | NA | 0.17 | NA |
| 290 | DLC1 | 12985243 | 13416766 | 1 | 1 | 19 | 574978 | -53590 | -53590 | 0 | 2.71 | NA | 0.01 |
| 291 | EPHA7 | 94007864 | 94185993 | 9 | 1 | 5 | 5242062 | -2654236 | -2654236 | 0 | NA | NA | NA |
| 292 | TRIM35 | 27198321 | 27224751 | 0 | 1 | 30 | 165 | -26478 | 165 | 0 | 0.29 | NA | NA |
| 293 | LRRC50 | 82736366 | 82769024 | 3 | 1 | 54 | 116798 | -101 | -101 | 0 | 0.21 | 0.02 | NA |
| 294 | CNGB3 | 87655277 | 87825017 | 0 | 1 | 38 | 122823 | -1691298 | 122823 | 0 | 0.02 | NA | NA |
| 295 | ASCC3 | 101062791 | 101435961 | 79 | 1 | 6 | 16667349 | -43297 | -43297 | 0 | NA | NA | 0.02 |
| 296 | RFC2 | 73283770 | 73306674 | 0 | 1 | 9 | 35065 | -1671 | -1671 | 0 | NA | NA | NA |
| 297 | CLEC3A | 76613944 | 76623495 | 0 | 1 | 52 | 67557 | -280292 | 67557 | 0 | 0.17 | 0.10 | 0.03 |
| 298 | IL17C | 87232502 | 87234385 | 0 | 1 | 58 | 2814 | -6746 | 2814 | 0 | NA | 0.02 | NA |
| 299 | BMP1 | 22078645 | 22125782 | 0 | 1 | 25 | 7380 | -8355 | 7380 | 0 | 0.14 | 0.14 | NA |
| 300 | CPA4 | 129720230 | 129751249 | 0 | 1 | 13 | 20643 | -3360 | -3360 | 0 | NA | NA | NA |
| 301 | OC90 | 133105667 | 133167084 | 0 | 1 | 45 | 43354 | -10596 | -10596 | 0 | 0.05 | NA | 0.06 |
| 302 | HEPH | 65299388 | 65403956 | 0 | 1 | 69 | 328248 | NA | 328248 | 0 | 0.02 | NA | NA |
| 303 | LRP12 | 105570643 | 105670344 | 0 | 1 | 41 | 729979 | -22190 | -22190 | 0 | NA | 0.07 | NA |
| 304 | AGFG2 | 99974770 | 100003778 | 0 | 1 | 12 | 5792 | -44412 | 5792 | 0 | NA | NA | 0.16 |
| 305 | TRPA1 | 73096040 | 73150373 | 0 | 1 | 34 | 492151 | -176755 | -176755 | 0 | 0.17 | NA | NA |
| 306 | GINS2 | 84268782 | 84280089 | 0 | 1 | 57 | 18535 | -1471 | -1471 | 0 | NA | 0.10 | NA |
| 307 | CENPH | 68521131 | 68541939 | 0 | 1 | 4 | 7390 | NA | 7390 | 0 | NA | 0.05 | NA |
| 308 | KLHL36 | 83239632 | 83253416 | 0 | 1 | 56 | 37634 | -143838 | 37634 | 0 | 0.02 | 0.02 | NA |
| 309 | ARHGEF10L | 17738917 | 17896956 | 0 | 1 | 1 | 57439 | -1482527 | 57439 | 0 | NA | 0.10 | NA |
| 310 | TRAPPC2L | 87451007 | 87455020 | 0 | 1 | 60 | 13748 | -122 | -122 | 0 | NA | 0.05 | NA |
| 311 | TCF25 | 88467520 | 88505287 | 0 | 1 | 62 | 7881 | -2292 | -2292 | 0 | NA | 0.10 | NA |

| | | | | | | | | | | |
|---|---|---|---|---|---|---|---|---|---|---|
| 312 | TNFRSF10D | 23049051 | 23077485 | 0 | 27 | 1 | 27431 | -115396 | 27431 | 0 | 0.05 | NA | NA |
| 313 | MYOM2 | 1980565 | 2080779 | 0 | 14 | 1 | 699503 | -86359 | -86359 | 0 | 0.10 | NA | NA |
| 314 | GCSH | 79673430 | 79687481 | 0 | 53 | 1 | 4504 | -5057 | 4504 | 0 | NA | 0.05 | NA |
| 315 | KIAA1609 | 83068608 | 83095794 | 1 | 55 | 1 | 143838 | -13315 | -13315 | 0 | NA | 0.05 | NA |
| 316 | FANCA | 88331460 | 88410566 | 0 | 62 | 1 | 11842 | -246990 | 11842 | 0 | 0.05 | NA | NA |
| 317 | ERI1 | 8897856 | 8928139 | 1 | 15 | 1 | 522716 | -109315 | -109315 | 0 | NA | NA | NA |
| 318 | HSDL1 | 82713389 | 82736265 | 0 | 54 | 1 | 101 | -5371 | 101 | 0 | NA | 0.07 | NA |
| 319 | KIAA0182 | 84202524 | 84267311 | 0 | 57 | 1 | 1471 | -517197 | 1471 | 0 | NA | 0.07 | NA |
| 320 | CBFA2T3 | 87468768 | 87570902 | 2 | 60 | 1 | 194762 | -13748 | -13748 | 0 | NA | 0.05 | NA |
| 321 | EGR3 | 22601119 | 22606760 | 0 | 26 | 1 | 306299 | -18566 | -18566 | 0 | NA | 0.07 | NA |
| 322 | PCOLCE | 100037818 | 100043732 | 0 | 12 | 1 | 3929 | -1144 | -1144 | 0 | NA | NA | NA |
| 323 | C16orf85 | 87147613 | 87164049 | 0 | 58 | 1 | 294 | -18723 | 294 | 0 | NA | 0.10 | 0.02 |
| 324 | HMBOX1 | 28803830 | 28966706 | 0 | 32 | 1 | 14009 | -699246 | 14009 | 0 | 0.02 | NA | NA |
| 325 | MTMR9 | 11179410 | 11223062 | 6 | 17 | 1 | 165868 | -154255 | -154255 | 0 | 0.05 | NA | NA |
| 326 | MSC | 72916332 | 72919285 | 0 | 34 | 1 | 176755 | -479311 | 176755 | 0 | 0.07 | NA | NA |
| 327 | ST3GAL2 | 68970839 | 69030492 | 28 | 50 | 1 | 2343793 | -6059 | -6059 | 0 | 0.21 | 0.14 | NA |
| 328 | FOXF1 | 85101634 | 85105570 | 0 | 57 | 1 | 15714 | -587924 | 15714 | 0 | NA | 0.47 | NA |
| 329 | C8orf58 | 22513067 | 22517605 | 0 | 26 | 1 | 597 | -1584 | 597 | 0 | 0.07 | NA | NA |
| 330 | KCTD9 | 25341283 | 25371837 | 0 | 29 | 1 | 591 | -14747 | 591 | 0 | NA | NA | NA |
| 331 | ANGPT1 | 108330899 | 108579459 | 0 | 42 | 1 | 401262 | -1444960 | 401262 | 0 | 0.21 | NA | NA |
| 332 | GDAP1 | 75425173 | 75441888 | 0 | 35 | 1 | 457439 | -29056 | -29056 | 0 | 0.07 | 0.14 | NA |
| 333 | RNF166 | 87290411 | 87300312 | 1 | 58 | 1 | 2604 | -10028 | 2604 | 0 | NA | NA | 0.04 |
| 334 | KLHL1 | 69172727 | 69580592 | 0 | 49 | 1 | 1329507 | -2470149 | 1329507 | 0 | 0.17 | 0.05 | NA |
| 335 | LOXL2 | 23210097 | 23317667 | 0 | 28 | 1 | -18281 | -34647 | -18281 | 0 | NA | NA | NA |
| 336 | WISP1 | 134272494 | 134310751 | 2 | 46 | 1 | 1248464 | -88015 | -88015 | 0 | 0.14 | NA | 0.06 |
| 337 | C8orf80 | 27935607 | 27997307 | 0 | 31 | 1 | 2452 | -29490 | 2452 | 0 | 0.80 | NA | NA |
| 338 | LAT2 | 73261662 | 73282099 | 0 | 9 | 1 | 1671 | -12304 | 1671 | 0 | NA | 0.05 | NA |
| 339 | USP10 | 83291050 | 83371026 | 0 | 56 | 1 | 40087 | -37634 | -37634 | 0 | 0.17 | 0.17 | NA |
| 340 | CDH15 | 87765664 | 87789400 | 0 | 61 | 1 | 72136 | -194762 | 72136 | 0 | NA | 0.14 | NA |
| 341 | WFDC1 | 82885822 | 82920888 | 0 | 55 | 1 | 38746 | -116798 | 38746 | 0 | 0.17 | 0.05 | 0.13 |
| 342 | C7orf51 | 99919486 | 99930358 | 1 | 12 | 1 | 44412 | -4648 | -4648 | 0 | NA | NA | NA |
| 343 | EBF2 | 25758042 | 25958292 | 2 | 29 | 1 | 533035 | -336689 | -336689 | 0 | 1.76 | 0.07 | 0.05 |
| 344 | CCDC125 | 68612278 | 68664392 | 0 | 4 | 1 | 31935 | -3274 | -3274 | 0 | NA | NA | 0.57 |
| 345 | LGI3 | 22060290 | 22070290 | 1 | 24 | 1 | 8355 | -4897 | -4897 | 0 | NA | 0.07 | NA |
| 346 | NUDT18 | 22020328 | 22023403 | 0 | 24 | 1 | 4474 | -2493 | -2493 | 0 | NA | 0.17 | NA |
| 347 | PHYHIP | 22133162 | 22145796 | 0 | 25 | 1 | 12768 | -7380 | -7380 | 0 | 1.63 | 0.14 | NA |
| 348 | PILRA | 99809004 | 99835650 | 1 | 11 | 1 | 29540 | -5616 | -5616 | 0 | NA | NA | 0.05 |
| 349 | KAT2A | 37518657 | 37526872 | 0 | 64 | 1 | 1489 | -380 | -380 | 0 | 1.63 | 1.16 | 0.57 |
| 350 | CSMD3 | 113304337 | 114518418 | 0 | 43 | 1 | 1971482 | -4139285 | 1971482 | 0 | NA | 0.25 | NA |
| 351 | REEP4 | 22051478 | 22055393 | 0 | 24 | 1 | 4897 | -6152 | 4897 | 0 | NA | 0.29 | NA |
| 352 | TUBB3 | 88513168 | 88530006 | 1 | 62 | 1 | 12678 | -7881 | -7881 | 0 | NA | 0.07 | NA |
| 353 | CDT1 | 87397687 | 87403166 | 1 | 59 | 1 | 4478 | -67370 | 4478 | 0 | NA | NA | NA |
| 354 | EDA2R | 65732204 | 65775608 | 0 | 69 | 1 | 904991 | -328248 | -328248 | 0 | 0.07 | NA | NA |

| 355 | DUS1L | 77609043 | 77629242 | 0 | 1 | 66 | 262 | -40474 | 262 | 0 | NA | NA | 0.16 |
| 356 | LRCH4 | 100009570 | 100021712 | 0 | 1 | 12 | 180 | -5792 | 180 | 0 | NA | NA | 0.14 |
| 357 | TMEM75 | 129029046 | 129029462 | 2 | 1 | 44 | 2104073 | -206193 | -206193 | 0 | 0.74 | NA | NA |
| 358 | NUDT7 | 76313912 | 76333652 | 0 | 1 | 52 | 280292 | -287400 | 280292 | 0 | 0.14 | NA | NA |
| 359 | TSGA14 | 129823611 | 129868133 | 2 | 1 | 13 | 45149 | -8446 | -8446 | 0 | NA | NA | 4.49 |
| 360 | CDC42BPG | 64348240 | 64368617 | 0 | 1 | 47 | 80139 | -12898 | -12898 | 0 | NA | NA | 0.18 |
| 361 | TSC22D4 | 99902080 | 99914838 | 2 | 1 | 12 | 4648 | -32404 | 4648 | 0 | NA | NA | 0.11 |
| 362 | NOTUM | 77503689 | 77512353 | 0 | 1 | 65 | 16362 | -3903967 | 16362 | 0 | NA | NA | 0.32 |
| 363 | HSPB9 | 37528361 | 37528897 | 0 | 1 | 64 | 1627 | -1489 | -1489 | 0 | NA | NA | 0.44 |
| 364 | TFR2 | 100055975 | 100077109 | 0 | 1 | 12 | 1569 | -5043 | 1569 | 0 | NA | NA | 0.29 |
| 365 | SLA | 134118155 | 134184479 | 0 | 1 | 46 | 88015 | 98170 | 88015 | 0 | 0.14 | NA | NA |
| 366 | WWOX | 76691052 | 77803532 | 2 | 1 | 52 | 1391644 | -67557 | -67557 | 0 | 4.45 | NA | NA |
| 367 | POU5F1B | 128497039 | 128498621 | 0 | 1 | 44 | 318241 | -2323848 | 318241 | 0 | 0.42 | NA | NA |
| 368 | OPHN1 | 67179440 | 67570372 | NA | 1 | 69 | NA | -318596 | -318596 | 0 | 2.24 | NA | NA |

TABLE 7

| Final Rank | Gene Name | OncoScan V2 Probes | OncoScan V2 kbs/probe | SNP 6.0 Probes | SNP 6.0 kbs/probe |
|---|---|---|---|---|---|
| 1 | PPP3CC | 30 | 4 | 62 | 2 |
| 2 | SLCO5A1 | 22 | 8 | 114 | 2 |
| 3 | SLC7A5 | 6 | 17 | 50 | 2 |
| 4 | SLC7A2 | 20 | 5 | 100 | 1 |
| 5 | CRISPLD2 | 13 | 8 | 67 | 2 |
| 6 | CDH13 | 180 | 3 | 661 | 1 |
| 7 | CDH8 | 30 | 13 | 247 | 2 |
| 8 | CDH2 | 57 | 4 | 129 | 2 |
| 9 | ASAH1 | 27 | 4 | 112 | 1 |
| 10 | KCNB2 | 44 | 10 | 337 | 1 |
| 11 | KCNH4 | 13 | 8 | 38 | 3 |
| 12 | KCTD8 | 18 | 16 | 130 | 2 |
| 13 | JPH1 | 15 | 7 | 87 | 1 |
| 14 | MEST | 17 | 6 | 39 | 3 |
| 15 | NCALD | 19 | 7 | 73 | 2 |
| 16 | COL19A1 | 58 | 6 | 257 | 1 |
| 17 | MAP3K7 | 26 | 4 | 54 | 2 |
| 18 | YWHAG | 11 | 9 | 47 | 2 |
| 19 | NOL4 | 23 | 9 | 93 | 2 |
| 20 | ENOX1 | 80 | 7 | 480 | 1 |
| 21 | CSMD1 | 547 | 4 | 2909 | 1 |
| 22 | SGCZ | 190 | 6 | 1060 | 1 |
| 23 | PDE10A | 60 | 6 | 266 | 1 |
| 24 | PCDH9 | 90 | 11 | 677 | 1 |
| 25 | HTR2A | 74 | 1 | 106 | 1 |
| 26 | HIP1 | 21 | 11 | 109 | 2 |
| 27 | CD226 | 36 | 3 | 72 | 2 |
| 28 | DCC | 187 | 7 | 836 | 1 |
| 29 | CC2D1A | 5 | 20 | 33 | 3 |
| 30 | PTK2B | 60 | 3 | 117 | 1 |
| 31 | BCMO1 | 16 | 6 | 73 | 1 |
| 32 | MACROD1 | 5 | 38 | 70 | 3 |
| 33 | GRID2 | 176 | 8 | 758 | 2 |
| 34 | DIAPH3 | 39 | 13 | 264 | 2 |
| 35 | PILRB | 6 | 17 | 16 | 6 |
| 36 | MEIS2 | 28 | 8 | 138 | 2 |
| 37 | MSRA | 102 | 4 | 374 | 1 |
| 38 | DPYD | 328 | 3 | 472 | 2 |
| 39 | ANKRD11 | 22 | 11 | 129 | 2 |
| 40 | NRXN1 | 110 | 4 | 350 | 1 |
| 41 | ADCY8 | 68 | 4 | 251 | 1 |
| 42 | TRDN | 40 | 11 | 257 | 2 |
| 43 | STAU2 | 46 | 8 | 191 | 2 |
| 44 | SF1 | 12 | 8 | 33 | 3 |
| 45 | CLIP2 | 4 | 34 | 40 | 3 |
| 46 | CLDN3 | 7 | 14 | 32 | 3 |
| 47 | ZSWIM4 | 4 | 25 | 30 | 3 |
| 48 | GLRB | 16 | 7 | 53 | 2 |
| 49 | DCHS2 | 25 | 7 | 96 | 2 |
| 50 | TRPS1 | 19 | 15 | 156 | 2 |
| 51 | MDGA2 | 44 | 12 | 301 | 2 |
| 52 | CNBD1 | 31 | 17 | 252 | 2 |
| 53 | STAG3 | 13 | 8 | 30 | 3 |
| 54 | GATA4 | 16 | 6 | 71 | 1 |
| 55 | VPS13B | 5 | 26 | 53 | 2 |
| 56 | DOCK5 | 45 | 6 | 160 | 2 |
| 57 | ZHX2 | 32 | 7 | 144 | 1 |
| 58 | ARHGEF5 | 3 | 33 | 28 | 4 |
| 59 | SDC2 | 31 | 4 | 97 | 1 |
| 60 | MYLK | 19 | 5 | 65 | 2 |
| 61 | LPHN3 | 68 | 9 | 291 | 2 |
| 62 | MOSPD3 | 4 | 25 | 19 | 5 |
| 63 | GYS2 | 16 | 6 | 76 | 1 |
| 64 | GAS8 | 20 | 5 | 80 | 1 |
| 65 | RAB9A | 16 | 6 | 61 | 2 |
| 66 | POLR3D | 11 | 9 | 38 | 3 |
| 67 | PSD3 | 77 | 4 | 255 | 1 |
| 68 | ZFPM2 | 80 | 6 | 290 | 2 |
| 69 | ATP6V1C1 | 18 | 6 | 69 | 1 |
| 70 | MEF2C | 34 | 4 | 58 | 2 |
| 71 | PKIA | 10 | 11 | 49 | 2 |
| 72 | ADAMTS18 | 41 | 4 | 191 | 1 |
| 73 | STYXL1 | 35 | 3 | 58 | 2 |
| 74 | EPM2A | 9 | 15 | 50 | 3 |
| 75 | LEPREL1 | 23 | 8 | 143 | 1 |
| 76 | GABRA2 | 23 | 7 | 80 | 2 |
| 77 | RCOR2 | 11 | 9 | 35 | 3 |
| 78 | MFHAS1 | 20 | 6 | 120 | 1 |
| 79 | SCARA5 | 31 | 5 | 108 | 1 |
| 80 | CCDC25 | 16 | 6 | 71 | 1 |
| 81 | PIEZO1 | 0 | #DIV/0! | 27 | 4 |
| 82 | CTSB | 21 | 5 | 85 | 1 |
| 83 | PTK2 | 40 | 9 | 197 | 2 |
| 84 | SPIRE2 | 8 | 13 | 50 | 2 |
| 85 | PROSER1 | 7 | 14 | 49 | 2 |
| 86 | BOD1L | 8 | 13 | 52 | 2 |
| 87 | FAM160B2 | 0 | #DIV/0! | 31 | 3 |
| 88 | NUS1 | 13 | 8 | 43 | 2 |
| 89 | MTHFSD | 14 | 7 | 93 | 1 |
| 90 | UBR5 | 15 | 12 | 54 | 3 |
| 91 | GALNS | 2 | 50 | 24 | 4 |
| 92 | FSTL5 | 80 | 10 | 477 | 2 |
| 93 | SIM1 | 19 | 5 | 72 | 1 |
| 94 | TG | 65 | 4 | 281 | 1 |
| 95 | BFSP2 | 14 | 7 | 51 | 2 |
| 96 | MMP16 | 85 | 4 | 160 | 2 |
| 97 | RIMS2 | 38 | 20 | 387 | 2 |
| 98 | PDS5B | 12 | 18 | 67 | 3 |
| 99 | CDK7 | 2 | 50 | 40 | 3 |
| 100 | CNTNAP4 | 54 | 6 | 266 | 1 |
| 101 | CFDP1 | 10 | 16 | 70 | 2 |
| 102 | FBXL4 | 4 | 25 | 58 | 2 |
| 103 | RFX1 | 5 | 20 | 34 | 3 |
| 104 | NALCN | 69 | 6 | 306 | 1 |
| 105 | STX1A | 8 | 13 | 22 | 5 |
| 106 | CYP7B1 | 16 | 14 | 92 | 2 |
| 107 | ARHGEF10 | 28 | 6 | 104 | 1 |
| 108 | ENTPD4 | 16 | 6 | 59 | 2 |
| 109 | ZNF704 | 12 | 22 | 113 | 2 |
| 110 | KIAA1456 | 28 | 4 | 127 | 1 |
| 111 | SLC9A9 | 105 | 6 | 449 | 1 |
| 112 | CHMP7 | 20 | 5 | 43 | 2 |
| 113 | GPC5 | 137 | 11 | 973 | 2 |
| 114 | MYC | 23 | 4 | 66 | 2 |
| 115 | STIP1 | 4 | 25 | 36 | 3 |
| 116 | ZBTB20 | 8 | 13 | 75 | 1 |
| 117 | MEN1 | 11 | 9 | 29 | 3 |
| 118 | SLC26A7 | 7 | 24 | 77 | 2 |
| 119 | ALCAM | 24 | 7 | 94 | 2 |
| 120 | KIF13B | 20 | 11 | 102 | 2 |
| 121 | MBTPS1 | 26 | 4 | 67 | 1 |
| 122 | PPP2R5B | 6 | 17 | 30 | 3 |
| 123 | VPS13C | 24 | 10 | 81 | 3 |
| 124 | ASPSCR1 | 4 | 25 | 13 | 8 |
| 125 | EPO | 12 | 8 | 31 | 3 |
| 126 | HEY1 | 13 | 8 | 59 | 2 |
| 127 | KALRN | 21 | 5 | 49 | 2 |
| 128 | RGS22 | 118 | 1 | 80 | 2 |
| 129 | WDR7 | 28 | 14 | 221 | 2 |
| 130 | COL11A1 | 53 | 5 | 158 | 2 |
| 131 | GHDC | 8 | 13 | 40 | 3 |
| 132 | ATP2C2 | 36 | 3 | 98 | 1 |
| 133 | CDH17 | 14 | 7 | 81 | 1 |
| 134 | DGKG | 31 | 8 | 178 | 1 |
| 135 | GRK5 | 53 | 5 | 161 | 2 |
| 136 | GRM1 | 84 | 5 | 251 | 2 |
| 137 | IMPA1 | 8 | 13 | 44 | 2 |
| 138 | RPL7 | 10 | 10 | 63 | 2 |
| 139 | COL21A1 | 24 | 9 | 111 | 2 |
| 140 | COL12A1 | 22 | 6 | 79 | 2 |
| 141 | MLYCD | 12 | 8 | 76 | 1 |
| 142 | AR | 35 | 6 | 83 | 2 |
| 143 | PLCB1 | 554 | 1 | 647 | 1 |
| 144 | ACTL8 | 15 | 7 | 71 | 1 |
| 145 | TFDP1 | 9 | 11 | 57 | 2 |
| 146 | IQCE | 4 | 25 | 47 | 2 |
| 147 | SMARCB1 | 20 | 5 | 43 | 2 |
| 148 | MTDH | 3 | 35 | 45 | 2 |
| 149 | NECAB2 | 24 | 4 | 78 | 1 |
| 150 | DEF8 | 12 | 8 | 34 | 3 |
| 151 | RNF40 | 10 | 10 | 35 | 3 |
| 152 | TICAM2 | 22 | 5 | 56 | 2 |

TABLE 7-continued

| Final Rank | Gene Name | OncoScan V2 | | SNP 6.0 | |
|---|---|---|---|---|---|
| | | Probes | kbs/probe | Probes | kbs/probe |
| 153 | GLG1 | 12 | 15 | 83 | 2 |
| 154 | MECOM | 15 | 7 | 72 | 1 |
| 155 | TCEB1 | 19 | 5 | 54 | 2 |
| 156 | CTNNA2 | 865 | 1 | 924 | 1 |
| 157 | NIPAL2 | 9 | 14 | 62 | 2 |
| 158 | CDCA2 | 8 | 13 | 69 | 1 |
| 159 | WWP2 | 5 | 34 | 99 | 2 |
| 160 | DDX19A | 11 | 9 | 38 | 3 |
| 161 | STK3 | 25 | 16 | 136 | 3 |
| 162 | DNAH2 | 15 | 9 | 54 | 2 |
| 163 | NFAT5 | 7 | 21 | 52 | 3 |
| 164 | CNGB1 | 21 | 5 | 87 | 1 |
| 165 | UBE2CBP | 16 | 12 | 100 | 2 |
| 167 | KIAA0196 | 13 | 8 | 74 | 1 |
| 168 | CLCNKB | 8 | 13 | 30 | 3 |
| 169 | C16orf80 | 11 | 9 | 45 | 2 |
| 170 | ZFHX3 | 75 | 4 | 166 | 2 |
| 171 | PPM1L | 26 | 13 | 189 | 2 |
| 172 | NKIRAS2 | 22 | 5 | 53 | 2 |
| 173 | RSPO2 | 16 | 13 | 117 | 2 |
| 174 | XPO7 | 11 | 10 | 72 | 1 |
| 175 | ME1 | 22 | 11 | 107 | 2 |
| 176 | NLGN4Y | 1 | 341 | 182 | 2 |
| 177 | LZTS1 | 17 | 6 | 70 | 1 |
| 178 | FBXL18 | 6 | 17 | 36 | 3 |
| 179 | TBC1D10B | 4 | 25 | 32 | 3 |
| 180 | WDR59 | 16 | 8 | 85 | 2 |
| 181 | BLK | 17 | 6 | 76 | 1 |
| 182 | MEPCE | 7 | 14 | 26 | 4 |
| 183 | DLGAP2 | 26 | 9 | 167 | 1 |
| 184 | ZFAT | 38 | 6 | 205 | 1 |
| 185 | FASN | 2 | 50 | 39 | 3 |
| 186 | GIGYF1 | 9 | 11 | 32 | 3 |
| 187 | ANXA13 | 12 | 8 | 85 | 1 |
| 188 | CDYL2 | 30 | 7 | 178 | 1 |
| 189 | TOX | 56 | 6 | 234 | 1 |
| 190 | NKX2-6 | 18 | 6 | 76 | 1 |
| 191 | RALYL | 54 | 14 | 437 | 2 |
| 192 | TBC1D22A | 45 | 10 | 357 | 1 |
| 193 | TFE3 | 6 | 17 | 20 | 5 |
| 194 | KCNAB1 | 55 | 8 | 292 | 2 |
| 195 | SULF1 | 33 | 6 | 153 | 1 |
| 196 | RAB5C | 19 | 5 | 38 | 3 |
| 197 | DHX58 | 22 | 5 | 40 | 3 |
| 198 | ASAP1 | 29 | 14 | 243 | 2 |
| 199 | CA5A | 9 | 11 | 43 | 2 |
| 200 | C6orf118 | 16 | 6 | 68 | 1 |
| 201 | NCOA2 | 44 | 7 | 138 | 2 |
| 202 | PKD1L2 | 36 | 4 | 129 | 1 |
| 203 | BANP | 4 | 36 | 74 | 2 |
| 204 | KIAA1967 | 1 | 100 | 51 | 2 |
| 205 | COPG2 | 8 | 28 | 29 | 8 |
| 206 | ZNF706 | 7 | 14 | 67 | 1 |
| 207 | GAN | 17 | 6 | 102 | 1 |
| 208 | PLCG2 | 20 | 10 | 199 | 1 |
| 209 | C19orf57 | 5 | 20 | 31 | 3 |
| 210 | PDGFRL | 20 | 5 | 97 | 1 |
| 211 | ESD | 50 | 2 | 76 | 1 |
| 212 | CPA5 | 28 | 4 | 67 | 1 |
| 213 | BIN3 | 4 | 25 | 54 | 2 |
| 214 | ZFHX4 | 13 | 16 | 101 | 2 |
| 215 | CPA6 | 39 | 9 | 262 | 1 |
| 216 | EYA1 | 25 | 7 | 124 | 1 |
| 217 | CHRNA2 | 45 | 2 | 73 | 1 |
| 218 | TNKS | 9 | 27 | 121 | 2 |
| 219 | HNF4G | 23 | 4 | 57 | 2 |
| 220 | LRCH1 | 43 | 5 | 148 | 1 |
| 221 | ADRA1A | 44 | 3 | 98 | 1 |
| 222 | EPHX2 | 26 | 4 | 79 | 1 |
| 223 | SORBS3 | 13 | 8 | 47 | 2 |
| 224 | GRIA2 | 24 | 7 | 56 | 3 |
| 225 | PDLIM2 | 7 | 14 | 50 | 2 |
| 226 | MTMR7 | 25 | 5 | 136 | 1 |
| 227 | FBXO24 | 3 | 33 | 21 | 5 |
| 228 | CRISPLD1 | 3 | 33 | 54 | 2 |
| 229 | DPYS | 17 | 6 | 64 | 2 |
| 230 | DTNA | 34 | 10 | 195 | 2 |
| 231 | KLHDC4 | 17 | 6 | 67 | 1 |
| 232 | CYBA | 4 | 25 | 42 | 2 |
| 233 | JPH3 | 7 | 16 | 60 | 2 |
| 234 | TMEM120A | 7 | 14 | 46 | 2 |
| 235 | MTUS1 | 21 | 5 | 121 | 1 |
| 236 | C8orf34 | 15 | 15 | 105 | 2 |
| 237 | GRHL2 | 39 | 5 | 164 | 1 |
| 238 | CPA2 | 27 | 4 | 53 | 2 |
| 239 | NAT2 | 44 | 2 | 91 | 1 |
| 240 | DPYSL2 | 11 | 15 | 114 | 1 |
| 241 | ZDHHC7 | 12 | 8 | 80 | 1 |
| 242 | ELP3 | 13 | 9 | 67 | 2 |
| 243 | RHOBTB2 | 11 | 9 | 56 | 2 |
| 244 | NEIL2 | 22 | 5 | 69 | 1 |
| 245 | HR | 2 | 50 | 32 | 3 |
| 246 | EFR3A | 18 | 7 | 67 | 2 |
| 247 | STMN4 | 8 | 13 | 64 | 2 |
| 248 | PRDM14 | 11 | 9 | 93 | 1 |
| 249 | MARVELD2 | 2 | 50 | 41 | 2 |
| 250 | SLC39A14 | 16 | 6 | 58 | 2 |
| 251 | ACTL6B | 2 | 50 | 23 | 4 |
| 252 | TUSC3 | 78 | 3 | 170 | 1 |
| 253 | COX4NB | 18 | 6 | 60 | 2 |
| 254 | XKR9 | 10 | 10 | 37 | 3 |
| 255 | C16orf46 | 14 | 7 | 76 | 1 |
| 256 | TAF9 | 2 | 50 | 33 | 3 |
| 257 | KCNQ3 | 56 | 6 | 279 | 1 |
| 258 | UTRN | 57 | 10 | 358 | 1 |
| 259 | RAD17 | 1 | 100 | 43 | 2 |
| 260 | ZFPM1 | 0 | #DIV/0! | 22 | 5 |
| 261 | PTDSS1 | 13 | 8 | 67 | 1 |
| 262 | IRF8 | 44 | 2 | 109 | 1 |
| 263 | YWHAZ | 23 | 4 | 53 | 2 |
| 264 | MRPS36 | 9 | 11 | 36 | 3 |
| 265 | LACTB2 | 8 | 13 | 38 | 3 |
| 266 | SNAI3 | 1 | 100 | 32 | 3 |
| 267 | TMEM71 | 14 | 7 | 68 | 1 |
| 268 | PREX2 | 79 | 2 | 123 | 1 |
| 269 | CPA1 | 23 | 4 | 53 | 2 |
| 270 | PHF20L1 | 13 | 8 | 63 | 2 |
| 271 | KIAA0513 | 16 | 6 | 80 | 1 |
| 272 | PI15 | 6 | 17 | 53 | 2 |
| 273 | PCM1 | 32 | 4 | 67 | 2 |
| 274 | SH2D4A | 17 | 6 | 77 | 1 |
| 275 | C16orf74 | 5 | 20 | 54 | 2 |
| 276 | TP63 | 62 | 4 | 186 | 1 |
| 277 | DACH1 | 33 | 14 | 230 | 2 |
| 278 | TNFRSF10A | 24 | 4 | 35 | 3 |
| 279 | MDH2 | 37 | 3 | 53 | 2 |
| 280 | PAG1 | 45 | 4 | 119 | 1 |
| 282 | BCAR1 | 13 | 8 | 55 | 2 |
| 283 | COX4I1 | 22 | 5 | 62 | 2 |
| 284 | EIF4H | 7 | 14 | 48 | 2 |
| 285 | ZC3H18 | 6 | 17 | 49 | 2 |
| 286 | STMN2 | 15 | 7 | 71 | 1 |
| 287 | AFG3L1P | 14 | 7 | 51 | 2 |
| 288 | HSD17B2 | 19 | 5 | 117 | 1 |
| 289 | MVD | 3 | 33 | 34 | 3 |
| 290 | DLC1 | 12 | 8 | 90 | 1 |
| 291 | EPHA7 | 30 | 7 | 119 | 2 |
| 292 | TRIM35 | 20 | 5 | 61 | 2 |
| 293 | DNAAF1 | 16 | 6 | 60 | 2 |
| 294 | CNGB3 | 38 | 5 | 119 | 2 |
| 295 | ASCC3 | 33 | 12 | 182 | 2 |
| 296 | RFC2 | 8 | 13 | 36 | 3 |
| 297 | CLEC3A | 20 | 5 | 90 | 1 |
| 298 | IL17C | 4 | 25 | 43 | 2 |
| 299 | BMP1 | 8 | 13 | 38 | 3 |
| 300 | CPA4 | 31 | 3 | 65 | 2 |
| 301 | OC90 | 24 | 4 | 73 | 1 |
| 302 | HEPH | 16 | 8 | 69 | 2 |
| 303 | LRP12 | 5 | 24 | 40 | 3 |
| 304 | AGFG2 | 4 | 25 | 26 | 4 |
| 305 | TRPA1 | 35 | 3 | 90 | 1 |
| 306 | GINS2 | 10 | 10 | 66 | 2 |

TABLE 7-continued

| | | OncoScan V2 | | SNP 6.0 | |
|---|---|---|---|---|---|
| Final Rank | Gene Name | Probes | kbs/probe | Probes | kbs/probe |
| 307 | CENPH | 14 | 7 | 33 | 3 |
| 308 | KLHL36 | 10 | 10 | 124 | 1 |
| 309 | ARHGEF10L | 10 | 18 | 77 | 2 |
| 310 | TRAPPC2L | 2 | 50 | 31 | 3 |
| 311 | TCF25 | 7 | 14 | 38 | 3 |
| 312 | TNFRSF10D | 25 | 4 | 37 | 3 |
| 313 | MYOM2 | 33 | 4 | 128 | 1 |
| 314 | GCSH | 19 | 5 | 95 | 1 |
| 315 | KIAA1609 | 35 | 3 | 88 | 1 |
| 316 | FANCA | 38 | 3 | 48 | 2 |
| 317 | ERI1 | 11 | 9 | 79 | 1 |
| 318 | HSDL1 | 20 | 5 | 57 | 2 |
| 319 | KIAA0182 | 8 | 13 | 42 | 2 |
| 320 | CBFA2T3 | 3 | 33 | 20 | 5 |
| 321 | EGR3 | 7 | 14 | 54 | 2 |
| 322 | PCOLCE | 3 | 33 | 19 | 5 |
| 323 | C16orf85 | 4 | 25 | 45 | 2 |
| 324 | HMBOX1 | 15 | 12 | 79 | 2 |
| 325 | MTMR9 | 18 | 6 | 62 | 2 |
| 326 | MSC | 11 | 9 | 85 | 1 |
| 327 | ST3GAL2 | 9 | 11 | 35 | 3 |
| 328 | FOXF1 | 16 | 6 | 117 | 1 |
| 329 | C8orf58 | 1 | 100 | 51 | 2 |
| 330 | KCTD9 | 13 | 8 | 79 | 1 |
| 331 | ANGPT1 | 44 | 6 | 183 | 1 |
| 332 | GDAP1 | 12 | 8 | 58 | 2 |
| 333 | RNF166 | 1 | 100 | 32 | 3 |
| 334 | KLHL1 | 56 | 8 | 264 | 2 |
| 335 | LOXL2 | 41 | 3 | 88 | 1 |
| 336 | WISP1 | 30 | 3 | 117 | 1 |
| 337 | C8orf80 | 17 | 6 | 83 | 1 |
| 338 | LAT2 | 8 | 13 | 44 | 2 |
| 339 | USP10 | 26 | 4 | 92 | 1 |
| 340 | CDH15 | 3 | 33 | 48 | 2 |
| 341 | WFDC1 | 18 | 6 | 107 | 1 |
| 342 | NYAP1 | 2 | 50 | 23 | 4 |
| 343 | EBF2 | 30 | 7 | 166 | 1 |
| 344 | CCDC125 | 1 | 100 | 39 | 3 |
| 345 | LGI3 | 5 | 20 | 32 | 3 |
| 346 | NUDT18 | 1 | 100 | 28 | 4 |
| 347 | PHYHIP | 12 | 8 | 39 | 3 |
| 348 | PILRA | 9 | 11 | 27 | 4 |
| 349 | KAT2A | 19 | 5 | 37 | 3 |
| 350 | CSMD3 | 114 | 10 | 606 | 2 |
| 351 | REEP4 | 4 | 25 | 34 | 3 |
| 352 | TUBB3 | 7 | 14 | 40 | 3 |
| 353 | CDT1 | 1 | 100 | 24 | 4 |
| 354 | EDA2R | 9 | 11 | 47 | 2 |
| 355 | DUS1L | 1 | 100 | 23 | 4 |
| 356 | LRCH4 | 3 | 33 | 20 | 5 |
| 357 | TMEM75 | 9 | 11 | 73 | 1 |
| 358 | NUDT7 | 22 | 5 | 101 | 1 |
| 359 | CEP41 | 17 | 6 | 46 | 2 |
| 360 | CDC42BPG | 11 | 9 | 29 | 3 |
| 361 | TSC22D4 | 0 | #DIV/0! | 18 | 6 |
| 362 | NOTUM | 3 | 33 | 5 | 20 |
| 363 | HSPB9 | 19 | 5 | 39 | 3 |
| 364 | TFR2 | 3 | 33 | 23 | 4 |
| 365 | SLA | 26 | 4 | 115 | 1 |
| 366 | WWOX | 14 | 7 | 78 | 1 |
| 367 | POU5F1B | 10 | 10 | 78 | 1 |
| 368 | OPHN1 | 26 | 16 | 207 | 2 |

What is claimed is:

1. A method of diagnosing and treating a subject, said method comprising
   (a) obtaining a prostate sample from the subject,
   (b) detecting the number of copies of at least 12 members of a metastatic gene signature set per cell of said sample, wherein the metastatic gene signature set consists of the following members: the PPP3CC genomic region, the SLCO5A1 genomic region, the SLC7A5 genomic region, the SLC7A2 genomic region, the CRISPLD2 genomic region, the CDH13 gene, the CDH8 gene, the CDH2 gene, the ASAH1 genomic, the KCNB2 genomic region, the KCNH4 genomic region, the CTD8 gene, the JPH1 genomic region, the MEST genomic region, the NCALD genomic region, the COL19A1 gene, the MAP3K7 genomic region, the YWHAG gene, the NOL4 genomic region, and the ENOX1 gene; wherein said detecting comprises performing nucleic acid hybridization, and wherein
   the PPP3CC genomic region consists of the genes PPP3CC, KIAA1967, BIN3, SORBS3, PDLIM2, RHOBTB2, SLC39A14, EGR3, and C8orf58,
   the SLCO5A1 genomic region consists of the genes SLCO5A1, SULF1, NCOA2, CPA6, C8orf34, PRDM14, and PREX2,
   the SLC7A5 genomic region consists of the genes SLC7A5, CA5A, BANP, KLHDC4, CYBA, JPH3, ZFPM1, SNAI3, ZC3H18, MVD, IL17C, C16orf85, and RNF166,
   the SLC7A2 genomic region consists of the genes SLC7A2, MTMR7 and MTUS1,
   the CRISPLD2 genomic region consists of the genes CRISPLD2, ZDHHC7, KIAA0513, KLHL36, and USP10,
   the ASAH1 genomic region consists of the genes ASAH1 and PCM1,
   the KCNB2 genomic region consists of the genes KCNB2, EYA1, XKR9, and TRPA1,
   the KCNH4 genomic region consists of the genes KCNH4, RAB5C, DHX58, KAT2A, and HSPB9,
   the JPH1 genomic region consists of the genes JPH1, HNF4G, CRISPLD1, PI115, and GDAP1,
   the MEST genomic region consists of the genes MEST, COPG2, CPAS, CPA2, CPA1, CPA4, and TSGA14,
   the NCALD genomic region consists of the genes NCALD, ZNF706, GRHL2, and YWHAZ,
   the MAP3K7 genomic region consists of the genes MAP3K7 and EPHA7, and
   the NOL4 genomic region consists of the genes NOL4 and DTNA, and
   (c) determining an aggregate score for the at least 12 members as compared to a number of copies per cell in non-cancer cells,
   (d) based on the determination in step (c) diagnosing that the subject has a risk of metastasis, and
   (e) treating the subject with at least one therapy selected from the group consisting of prostatectomy and radiation therapy.

2. The method of claim 1, wherein the at least 12 members include the PPP3CC genomic region, the SLCO5A1 genomic region, the SLC7A5 genomic region, the SLC7A2 genomic region, the CRISPLD2 genomic region, the CDH13 gene, the CDH8 gene, the CD/42 gene, the ASAH1 genomic region, the KCNB2 genomic region, the KCNH4 genomic region, and the CTD8 gene.

3. The method of claim 1, wherein the at least 12 members include all of the members in said metastatic gene signature set.

4. The method of claim 3, further comprising determining the number of copies per cell of at least one additional gene or genomic region selected from the group consisting of CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, NRXN1, ADCY8, TRDN, STAU2, SF1, CLIP2, CLDN3, ZSWIM4, GLRB, DCHS2, TRPS1, MDGA2, CNBD1, STAG3, GATA4, VPS13B, DOCKS, ZHX2, ARHGEF5, SDC2, MYLK, LPHN3, MOSPD3, GYS2, GASB, RAB9A, POLR3D, PSD3, ZFPM2, ATP6V1C1, MEF2C, PKIA, ADAMT518, STYXL1, EPM2A, LEPREL1, GABRA2, RCOR2, MFHAS1, SCARA5, CCDC25, FAM38A, CTSB, PTK2, SPIRE2, C13orf23, BOD1L, FAM160B2, NUS1, MTHFSD, UBR5, GALNS, FSTL5, SIM1, TG, BFSP2, MMP16, RIMS2, PDS5B, CDK7, CNTNAP4, CFDP1, FBXL4, RFX1, NALCN, STX1A, CYP7B1, ARHGEF10, ENTPD4, ZNF704, C8orf79, SLC9A9, CHMP7, GPC5, MYC, STIP1, ZBTB20, MEN1, SLC26A7, ALCAM, KIF13B, MBTPS1, PPP2R5B, VPS13C, ASPRSCR1, EPO, HEY1, KALRN, RGS22, WDR7, COL11A1, GHDC, ATP2C2, CDH17, DGKG, GRK5, GRM1, IMPA1, RPL7, COL21A1, COL12A1, MLYCD, AR, PLCB1, ACTL8, TFDP1, IQCE, SMARCB1, MTDH, NECAB2, DEF8, RNF40, TICAM2, GLG1, MECOM, TCEB1, CTNNA2, NIPAL2, CDCA2, WWP2, DDX19A, STK3, DNAH2, NFAT5, CNGB1, UBE2CBP, C8orf16, KIAA0196, CLC-NKB, C016orf80, ZFHX3, PPM1L, NKIRAS2, RSPO2, XPO7, ME1, NLGN4Y, LZTS1, FBXL18, TBC1D10B, WDR59, BLK, MEPCE, DLGAP2, ZFAT, FASN, GIGYF1, ANXA13, CDYL2, TOX, NKX2-6, RALYL, TBC1D22A, TFE3, KCNAB1, ASAP1, C6orf118, PKD1L2, GAN, PLCG2, C19orf57, PDGFRL, ESD, ZFHX4, CHRNA2, INKS, LRCH1, ADRA1A, EPHX2, GRIA2, FBXO24, DPYS, TMEM120A, NAT2, DPYSL2, ELP3, NEIL2, HR, EFR3A, STMN4, MARVELD2, ACTL6B, TUSC3, COX4NB, C16orf46, TAF9, KCNQ3, UTRN, RAD17, PTDSS1, IRF8, MRPS36, LACTB2, TMEM71, PHF20L1, SH2D4A, C16orf74, TP63, DACH1, TNFRSF10A, MDH2, PAG1, SLC25A37, BCAR1, COX411, EIF4H, STMN2, AFG3L1, HSD17B2, DLC1, TRIM35, LRRC50, CNGB3, ASCC3, RFC2, CLEC3A, BMP1, OC90, HEPH, LRP12, AGFG2, GINS2, CENPH, ARHGEF1OL, TRAPPC2L, TCF25, TNFRSF10D, MYOM2, GOSH, KIAA1609, FANCA, ERI1, HSDL1, KIAA0182, CBFA2T3, PCOLCE, HMBOX1, MTMR9, MSC, ST3GAL2, FOXF1, KCTD9, ANGPT1, KLHL1, LOXL2, WISP1, C8orf80, LAT2, CDH15, WFDC1, C7orf51, EBF2, CCDC125, LGI3, NUDT18, PHYHIP, PILRA, CSMD3, REEP4, TUBB3, CDT1, EDA2R, DUS1 L, LRCH4, TMEM75, NUDT7, CDC42BPG, TSC22D4, NOTUM, TFR2, SLA, WWOX, POU5F1B, and OPHN1.

5. The method of claim 4, wherein said at least one additional gene or genomic region comprises 20 genes and/or genomic regions selected from the group consisting of CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, NRXN1, ADCY8, TRDN, STAU2, SF1, CLIP2, CLDN3, ZSWIM4, GLRB, DCHS2, TRPS1, MDGA2, CNBD1, STAG3, GATA4, VPS13B, DOCKS, ZHX2, ARHGEF5, SDC2, MYLK, LPHN3, MOSPD3, GYS2, GASB, RAB9A, POLR3D, PSD3, ZFPM2, ATP6V1C1, MEF2C, PKIA, ADAMTS18, STYXL1, EPM2A, LEPREL1, GABRA2, RCOR2, MFHAS1, SCARA5, CCDC25, FAM38A, CTSB, PTK2, SPIRE2, C13orf23, BOD1L, FAM160B2, NUS1, MTHFSD, UBR5, GALNS, FSTL5, SIM1, TG, BFSP2, MMP16, RIMS2, PDS5B, CDK7, CNTNAP4, CFDP1, FBXL4, RFX1, NALCN, STX1A, CYP7B1, ARHGEF10, ENTPD4, ZNF704, C8orf79, SLC9A9, CHMP7, GPC5, MYC, STIP1, ZBTB20, MEN1, SLC26A7, ALCAM, KIF13B, MBTPS1, PPP2R5B, VPS13C, ASPRSCR1, EPO, HEY1, KALRN, RGS22, WDR7, COL11A1, GHDC, ATP2C2, CDH17, DGKG, GRK5, GRM1, IMPA1, RPL7, COL21A1, COL12A1, MLYCD, AR, PLCB1, ACTL8, TFDP1, IQCE, SMARCB1, MTDH, NECAB2, DEF8, RNF40, TICAM2, GLG1, MECOM, TCEB1, CTNNA2, NIPAL2, CDCA2, WWP2, DDX19A, STK3, DNAH2, NFAT5, CNGB1, UBE2CBP, C8orf16, KIAA0196, CLCNKB, C16orf80, ZFHX3, PPM1L, NKIRAS2, RSPO2, XPO7, ME1, NLGN4Y, LZTS1, FBXL18, TBC1D10B, WDR59, BLK, MEPCE, DLGAP2, ZFAT, FASN, GIGYF1, ANXA13, CDYL2, TOX, NKX2-6, RALYL, TBC1D22A, TFE3, KCNAB1, ASAP1, C6orf118, PKD1L2, GAN, PLCG2, C19orf57, PDGFRL, ESD, ZFHX4, CHRNA2, INKS, LRCH1, ADRA1A, EPHX2, GRIA2, FBXO24, DPYS, TMEM120A, NAT2, DPYSL2, ELP3, NEIL2, HR, EFR3A, STMN4, MARVELD2, ACTL6B, TUSC3, COX4NB, C16orf46, TAF9, KCNQ3, UTRN, RAD17, PTDSS1, IRF8, MRPS36, LACTB2, TMEM71, PHF20L1, SH2D4A, C16orf74, TP63, DACH1, TNFRSF10A, MDH2, PAG1, SLC25A37, BCAR1, COX411, EIF4H, STMN2, AFG3L1, HSD17B2, DLC1, TRIM35, LRRC50, CNGB3, ASCC3, RFC2, CLEC3A, BMP1, OC90, HEPH, LRP12, AGFG2, GINS2, CENPH, ARHGEF1OL, TRAPPC2L, TCF25, TNFRSF10D, MYOM2, GOSH, KIAA1609, FANCA, ERI1, HSDL1, KIAA0182, CBFA2T3, PCOLCE, HMBOX1, MTMR9, MSC, ST3GAL2, FOXF1, KCTD9, ANGPT1, KLHL1, LOXL2, WISP1, C8orf80, LAT2, CDH15, WFDC1, C7orf51, EBF2, CCDC125, LGI3, NUDT18, PHYHIP, PILRA, CSMD3, REEP4, TUBB3, CDT1, EDA2R, DUS1L, LRCH4, TMEM75, NUDT7, CDC42BPG, TSC22D4, NOTUM, TFR2, SLA, WWOX, POU5F1B, and OPHN1.

6. The method of claim 5, wherein said 20 genes and/or genomic regions consist of CSMD1, SGCZ, PDE10A, PCDH9, HTR2A, HIP1, CD226, DCC, CC2D1A, PTK2B, BCMO1, MACRDO1, GRID2, DIAPH3, PILRB, MEIS2, MSRA, DPYD, ANKRD11, and NRXN1.

* * * * *